United States Patent
Li et al.

(10) Patent No.: US 12,387,816 B2
(45) Date of Patent: Aug. 12, 2025

(54) PROCESSES FOR GENETIC AND CLINICAL DATA EVALUATION AND CLASSIFICATION OF COMPLEX HUMAN TRAITS

(71) Applicants: The Board of Trustees of the Leland Stanford Junior University, Stanford, CA (US); The United States Government as represented by the Department of Veterans Affairs, Washington, DC (US)

(72) Inventors: Jingjing Li, Stanford, CA (US); Sai Zhang, Palo Alto, CA (US); Michael P. Snyder, Stanford, CA (US); Cuiping Pan, Palo Alto, CA (US); Philip S. Tsao, Palo Alto, CA (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 833 days.

(21) Appl. No.: 16/961,120

(22) PCT Filed: Jan. 9, 2019

(86) PCT No.: PCT/US2019/012848
§ 371 (c)(1),
(2) Date: Jul. 9, 2020

(87) PCT Pub. No.: WO2019/139950
PCT Pub. Date: Jul. 18, 2019

(65) Prior Publication Data
US 2021/0158894 A1    May 27, 2021

Related U.S. Application Data

(60) Provisional application No. 62/727,260, filed on Sep. 5, 2018, provisional application No. 62/615,304, filed on Jan. 9, 2018.

(51) Int. Cl.
*G16B 20/20* (2019.01)
*G06F 17/18* (2006.01)
*G16B 40/20* (2019.01)

(52) U.S. Cl.
CPC ............ *G16B 20/20* (2019.02); *G06F 17/18* (2013.01); *G16B 40/20* (2019.02)

(58) Field of Classification Search
CPC ........ G16B 20/20; G16B 40/20; G16B 20/00; G06F 17/18
See application file for complete search history.

(56) References Cited

U.S. PATENT DOCUMENTS

| | | |
|---|---|---|
| 2013/0006342 A1 | 1/2013 | Wang et al. |
| 2013/0184161 A1 | 7/2013 | Kingsmore et al. |
| 2013/0224739 A1 | 8/2013 | Thorleifsson et al. |
| 2016/0357903 A1 | 12/2016 | Shendure et al. |

FOREIGN PATENT DOCUMENTS

WO    2019139950 A1    7/2019

OTHER PUBLICATIONS

Okser S. BioData Mining 6:5, pp. 1-16. (Year: 2013).*
Bhardwaj A. Expert Systems with Applications 42: 4611-4620. (Year: 2015).*
Swan Al. A machine learning heuristic to identify biologically relevant and minimal biomarker panels from omics data. BMC Genomics 16 (Supp 1): S2, pp. 1-12. (Year: 2015).*
Oxford Nanopore Technologies. "Precision Medicine and Digital Health." pp. 1-18. (Year: 2017).*
Kosmicki JA. Discovery of rare variants for complex phenotypes. Human Genetics 135: 625-634. (Year: 2016).*
Cawley GC. Sparse multinomial logistic regression via Bayesian L1 regularisation. IEEE Advances in Neural Information Processing Systems 19, Proceedings of the 2006 Conference, pp. 8. (Year: 2016).*
Smolander J. Deep learning classification methods for complex disorders. Master's Thesis, Tampere University of Technology, pp. 78. (Year: 2015).*
Wang Y. Diagnosis and treatment of congentical abdominal aortic aneurysm: a systematic review of reported cases. Orphanet Journal of Rare Diseases 10(4): 1-7. (Year: 2015).*
International Preliminary Report on Patentability for International Application No. PCT/US2019/012848, Report issued Jul. 14, 2020, Mailed Jul. 23, 2020, 17 Pgs.
International Search Report and Written Opinion for International Application No. PCT/US2019/012848, Search completed Mar. 19, 2019, Mailed Apr. 8, 2019, 23 Pgs.

(Continued)

*Primary Examiner* — Olivia M. Wise
*Assistant Examiner* — Robert J. Kallal
(74) *Attorney, Agent, or Firm* — KPPB LLP

(57) ABSTRACT

Processes to identify a subset of trait-related genes and classify individuals are described. Generally, systems generate classification models which are used to identify the subset of trait-related genes and classify individuals. The classification models are also used in various applications, including developing research tools, performing diagnostics, and treating individuals.

19 Claims, 33 Drawing Sheets
(23 of 33 Drawing Sheet(s) Filed in Color)

(56) References Cited

OTHER PUBLICATIONS

Aggarwal et al., "Abdominal aortic aneurysm: A comprehensive review," Experimental and Clinical Cardiology, vol. 16, No. 1, Spring 2011, pp. 11-15.

Aivatidi et al., "Oxidative stress during abdominal aortic aneurysm repair—Biomarkers and antioxidant's protective effect: a review," Eur Rev Med Pharmacal Sci., Mar. 2011, vol. 15, No. 3, pp. 245-252, p. 249, col. 2, para 3.

Auer et al., "Rare variant association studies: considerations, challenges and opportunities," Genome Medicine, vol. 7, No. 1, Feb. 23, 2015, 11 pgs.

Bentley et al., "Accurate whole human genome sequencing using reversible terminator chemistry," Nature, Articles, Nov. 6, 2008, vol. 456, pp. 53-59.

Biros et al., "Differential gene expression in human abdominal aortic aneurysm and aortic occlusive disease," Oncotarget, vol. 6, No. 15, May 30, 2015, pp. 12984-12996.

Bown, "Genomic insights into abdominal aortic aneurysms," Annals of the Royal College of Surgeons of England, vol. 96, No. 6, Sep. 2014, pp. 405-414.

Bradley et al., "Abdominal Aortic Aneurysm Genetic Associations: Mostly False? A Systematic Review and Meta-analysis," European Journal of Vascular and Endovascular Surgery, vol. 51, No. 1, Jan. 2016, pp. 64-75.

Carter et al., "Identifying Mendelian disease genes with the Variant Effect Scoring Tool," BMC Genomics, vol. 14, No. S3, May 28, 2013, 16 pgs.

Chatr-Aryamontri et al., "The BioGRID interaction database: 2017 update," Nucleic Acids Research, vol. 45, No. D1, Jan. 2017, pp. D369-D379.

Cho et al., "Compact Integration of Multi-Network Topology for Functional Analysis of Genes," Cell Systems, vol. 3, No. 6, Dec. 21, 2016, 28 pgs.

Cirulli et al., "Uncovering the roles of rare variants in common disease through whole-genome sequencing," Nature Reviews Genetics, vol. 11, No. 6, Jun. 2010, pp. 415-425.

Daugherty et al., "Angiotensin II promotes atherosclerotic lesions and aneurysms in apolipoprotein E-deficient mice," The Journal of Clinical Investigation, vol. 105, No. 11, Jun. 1, 2000, pp. 1605-1612.

Depristo et al., "A framework for variation discovery and genotyping using next-generation DNA sequencing data," Nature Genetics, vol. 43, Apr. 10, 2011, pp. 491-498.

Dong et al., "Comparison and integration of deleteriousness prediction methods for nonsynonymous SNVs in whole exome sequencing studies," Human Molecular Genetics, vol. 24, No. 8, Apr. 15, 2015, pp. 2125-2137.

Fontanarosa et al., "Using LASSO regression to detect predictive aggregate effects in genetic studies," BMC Proc. Nov. 29, 2011, vol. 5, Suppl9, article S69, pp. 1-5. Especially abstract, p. 2, col. 1, para 3 and 4, equation 2.

Gabel et al., "Molecular Fingerprint for Terminal Abdominal Aortic Aneurysm Disease," JAHA, Nov. 30, 2017, vol. 6, No. 12, Manuscript No. 006798 (pp. 1-18). Especially abstract.

Gaziano et al., "Million Veteran Program: A mega-biobank to study genetic influences on health and disease," Journal of Clinical Epidemiology, vol. 70, Feb. 1, 2016, pp. 214-223.

Golledge et al., "Genetics of abdominal aortic aneurysm," Current Opinion in Cardiology, vol. 28, No. 3, May 2013, pp. 290-296.

Golledge et al., "Obesity, Adipokines, and Abdominal Aortic Aneurysm," Circulation, vol. 116, No. 20, Nov. 13, 2007, pp. 2275-2279.

Hinterseher et al., "Genes and Abdominal Aortic Aneurysm," Annals of Vascular Surgery, vol. 25, No. 3, Apr. 2011, pp. 388-412.

Hobbs et al., "LDL Cholesterol is Associated with Small Abdominal Aortic Aneurysms," European Journal of Vascular and Endovascular Surgery, vol. 26, No. 6, Dec. 2003, pp. 618-622.

Jones et al., "Meta-Analysis of Genome-Wide Association Studies for Abdominal Aortic Aneurysm Identifies Four New Disease-Specific Risk Loci," Circulation Research, vol. 120, No. 2, Jan. 20, 2017, pp. 341-353.

Kuivaniemi et al., "Aortic Aneurysms: An Immune Disease With a Strong Genetic Component," Circulation, vol. 117, No. 2, Jan. 15, 2008, pp. 242-252.

Lee et al., "Rare-Variant Association Analysis: Study Designs and Statistical Tests," American Journal of Human Genetics, vol. 95, No. 1, Jul. 3, 2014, pp. 5-23.

Li et al., "Decoding the Genomics of Abdominal Aortic Aneurysm," Cell, Sep. 6, 2018, vol. 174, pp. 1361-1372, https://doi.org/10.1016/j.cell.2018.07.021.

Li et al., "Fast and accurate short read alignment with Burrows-Wheeler transform," Bioinformatics, May 18, 2009, vol. 25, No. 14, pp. 1754-1760.

Li et al., "Identification of Human Neuronal Protein Complexes Reveals Biochemical Activities and Convergent Mechanisms of Action in Autism Spectrum Disorders," Cell Systems, vol. 1, No. 5, Nov. 25, 2015, pp. 361-374.

Li et al., "Integrated systems analysis reveals a molecular network underlying autism spectrum disorders," Molecular Systems Biology, vol. 10, No. 12, Dec. 1, 2014, 17 pgs.

Maegdefessel et al., "Inhibition of microRNA-29b reduces murine abdominal aortic aneurysm development," The Journal of Clinical Investigation, vol. 122, No. 2, Feb. 1, 2012, pp. 497-506.

Maegdefessel et al., "miR-24 limits aortic vascular inflammation and murine abdominal aneurysm development," Nature Communications, vol. 5, No. 5214, Oct. 31, 2014, 14 pgs.

Manolio et al., "Finding the missing heritability of complex diseases," Nature, vol. 461, No. 7265, Oct. 8, 2009, pp. 747-753.

Maxim et al., "Screening tests: a review with examples," Inhalation Toxicology, vol. 26, No. 13, Sep. 29, 2014, pp. 811-828.

Mccarthy et al., "Genome-wide association studies for complex traits: consensus, uncertainty and challenges," Nature Reviews Genetics, vol. 9, May 2008, pp. 356-369.

Mccormick et al., "Role of Oxidative Stress in the Pathogenesis of Abdominal Aortic Aneurysms," Arteriosclerosis, Thrombosis, and Vascular Biology, vol. 27, No. 3, Mar. 2007, pp. 461-469.

Mckenna et al., "The Genome Analysis Toolkit: A MapReduce framework for analyzing next-generation DNA sequencing data," Genome Research, vol. 20, Jul. 12, 2010, pp. 1297-1303.

Menashi et al., "Collagen in abdominal aortic aneurysm: typing, content, and degradation," Journal of Vascular Surgery, vol. 6, No. 6, Dec. 1987, pp. 578-582.

Mills et al., "Natural genetic variation caused by small insertions and deletions in the human genome," Genome Research, vol. 21, No. 6, Jun. 2011, pp. 830-839.

Moxon et al., "Diagnosis and Monitoring of Abdominal Aortic Aneurysm: Current Status and Future Prospects," Current Problems in Cardiology, vol. 35, No. 10, Oct. 2010, pp. 512-548.

Myers et al., "Agreement between activity-monitoring devices during home rehabilitation: a substudy of the AAA Stop trial," Journal of Aging and Physical Activity, vol. 22, No. 1, Jan. 2014, pp. 87-95.

Nordon et al., "Pathophysiology and epidemiology of abdominal aortic aneurysms," Nature Reviews Cardiology, vol. 8, No. 2, Nov. 16, 2010, pp. 92-102.

Pan et al., "Cloud-based Interactive Analytics for Terabytes of Genomic Variants Data," Bioinformatics, vol. 33, No. 23, Dec. 1, 2017, pp. 3709-3715.

Pearce et al., "Atherosclerotic Peripheral Vascular Disease Symposium II: Controversies in Abdominal Aortic Aneurysm Repair," Circulation, vol. 118, 2008, pp. 2860-2863.

Pedregosa et al., "Scikit-learn: Machine Learning in Python," Journal of Machine Learning Research, Oct. 2011, vol. 12, pp. 2825-2830.

Purcell et al., "Plink: A Tool Set for Whole-Genome Association and Population-Based Linkage Analyses," The American Journal of Human Genetics, Sep. 2007, vol. 81, pp. 559-575, DOI: 10.1086/519795.

(56) References Cited

OTHER PUBLICATIONS

Sandford et al., "The Genetic Basis of Abdominal Aortic Aneurysms: A Review," European Journal of Vascular and Endovascular Surgery, vol. 33, No. 4, Apr. 1, 2007, pp. 381-390.

Sherry et al., "dbSNP: the NCBI database of genetic variation," Nucleic Acids Research, Jan. 1, 2001. 29(1): pp. 308-311. PMCID: 29783.

Spin et al., "Transcriptional profiling and network analysis of the murine angiotensin II-induced abdominal aortic aneurysm," Physiological Genomics, vol. 43, No. 17, Sep. 8, 2011, pp. 993-1003.

Stackelberg et al., "Lifestyle and Risk of Screening-Detected Abdominal Aortic Aneurysm in Men," Journal of the American Heart Association, vol. 6, No. 5, May 5, 2017, 11 pgs.

Thompson et al., "Pathophysiology of Abdominal Aortic Aneurysms: Insights from the Elastase-Induced Model in Mice with Different Genetic Backgrounds," Annals of the New York Academy of Sciences, vol. 1085, No. 1, The Abdominal Aortic Aneurysm: Genetics, Pathophysiology, and Molecular Biology, Nov. 2006, pp. 59-73.

Tibshirani, "Regression shrinkage and selection via the lasso: a retrospective," Journal of the Royal Statistical Society: Statistical Methodology, Series B, vol. 73, No. 3, Jun. 2011, pp. 273-282.

Torsney et al., "Elevation of Plasma High-Density Lipoproteins Inhibits Development of Experimental Abdominal Aortic Aneurysms," Arteriosclerosis, Thrombosis, and Vascular Biology, vol. 32, No. 11, Nov. 2012, pp. 2678-2686.

Tsamis et al., "Elastin and collagen fibre microstructure of the human aorta in ageing and disease: a review," Journal of the Royal Society Interface, vol. 10, No. 83, Mar. 27, 2013, 22 pgs.

Visscher et al., "Five Years of GWAS Discovery," The American Journal of Human Genetics, vol. 90, No. 1, Jan. 13, 2012, pp. 7-24.

Wahlgren et al., "Genetic and environmental contributions to abdominal aortic aneurysm development in a twin population," Journal of Vascular Surgery, vol. 51, No. 1, Jan. 2010, pp. 3-7.

Zook et al., "Integrating human sequence data sets provides a resource of benchmark SNP and indel genotype calls," Nature Biotechnology, vol. 32, No. 3, Feb. 16, 2014, pp. 246-251.

\* cited by examiner

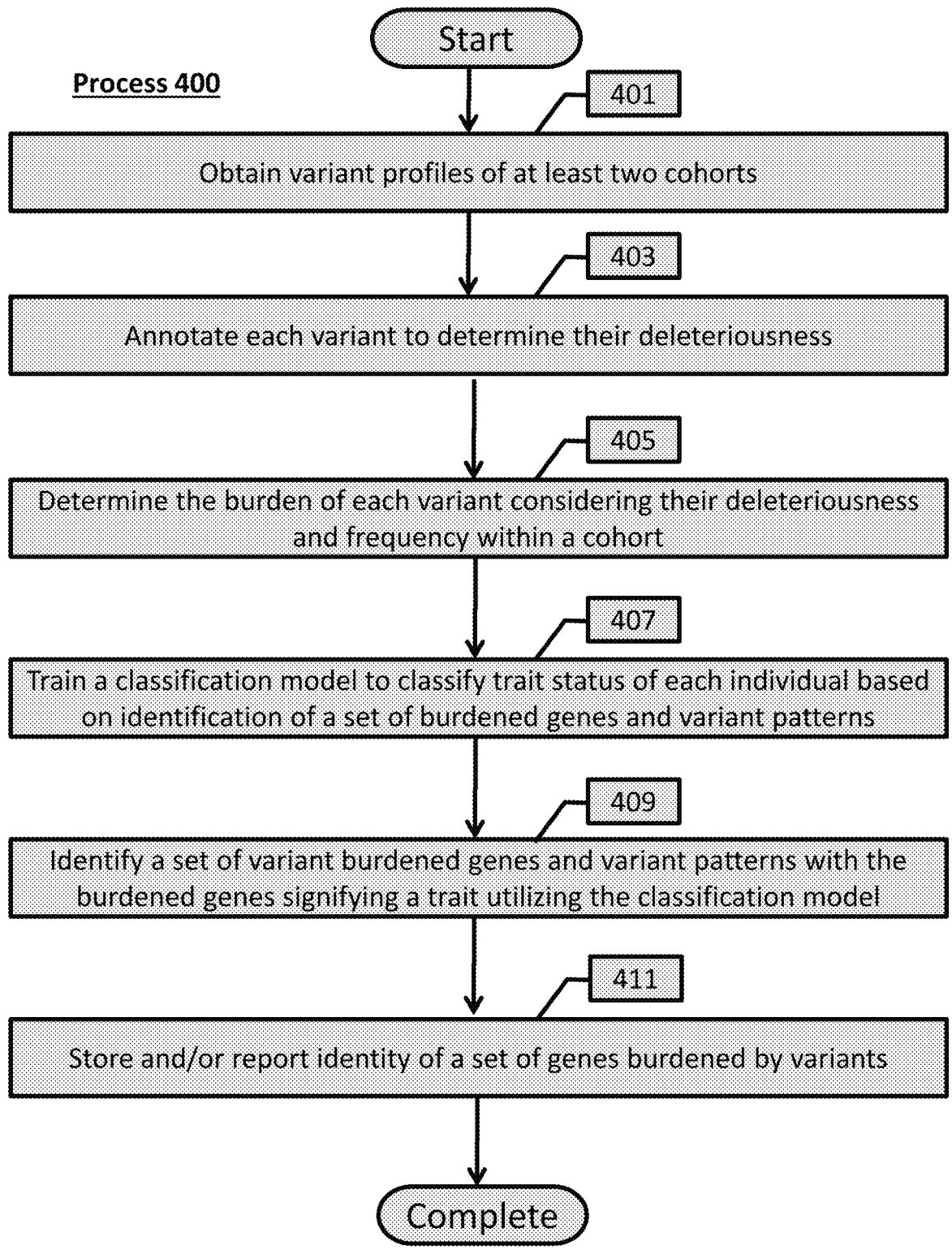

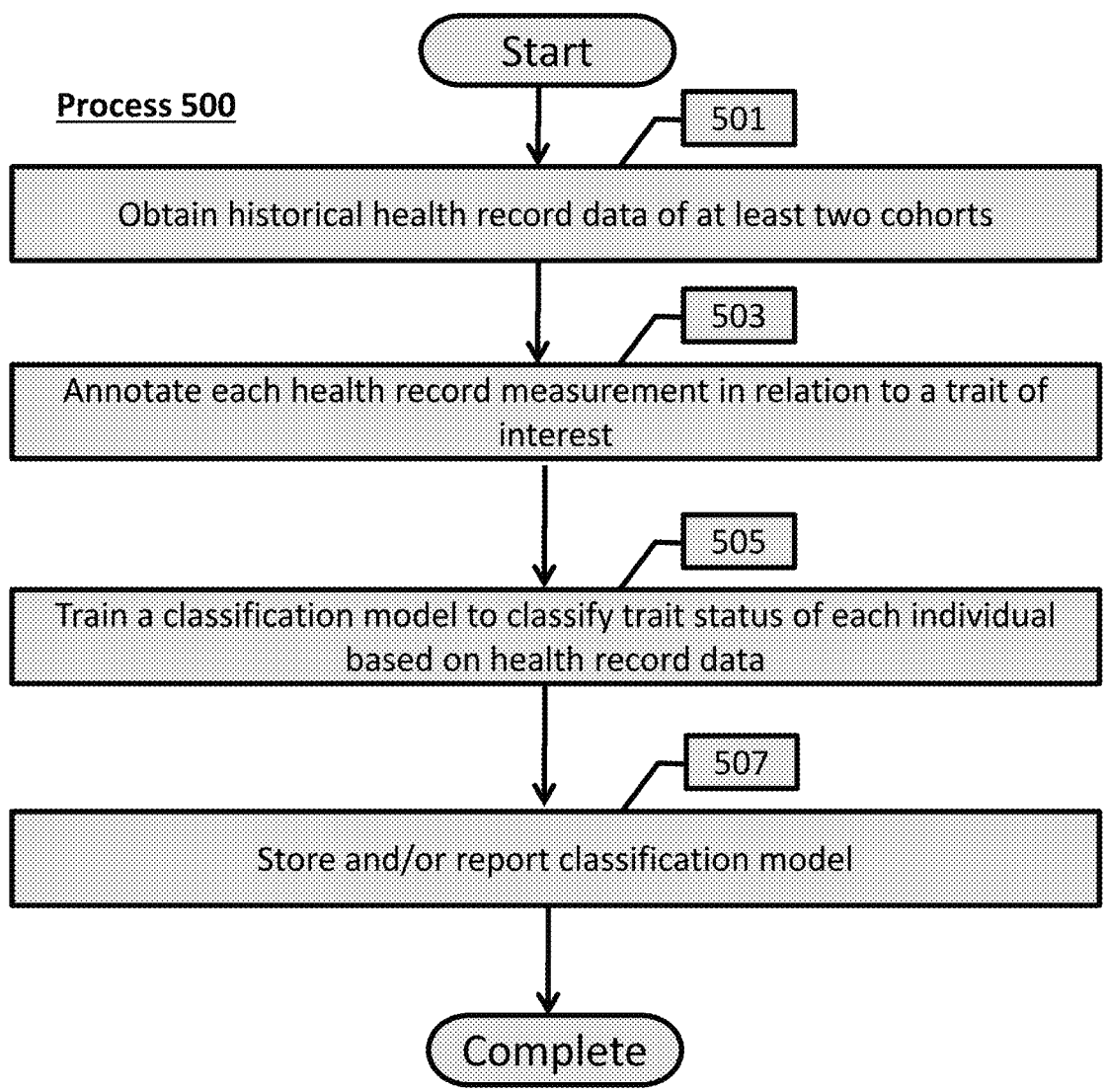

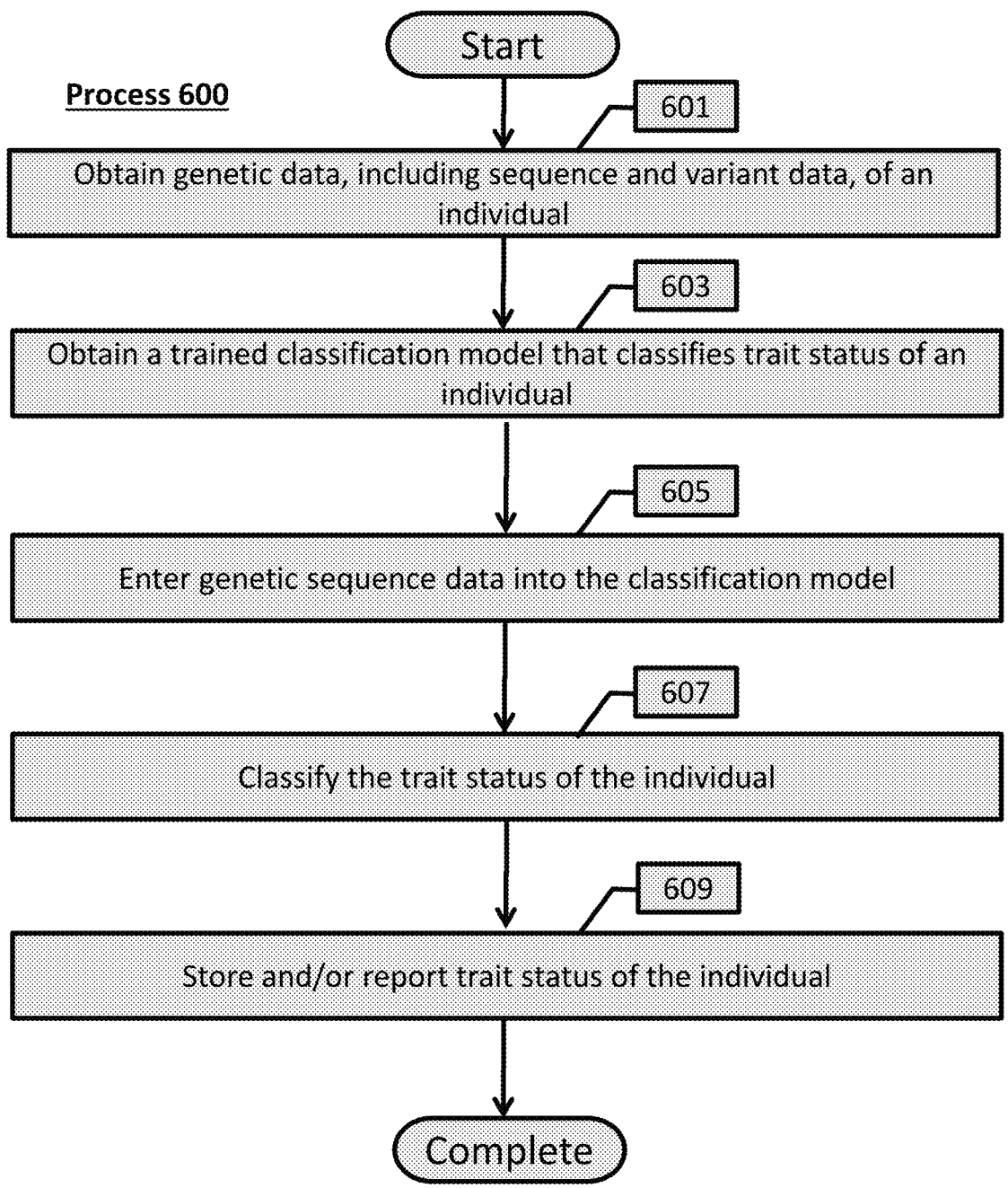

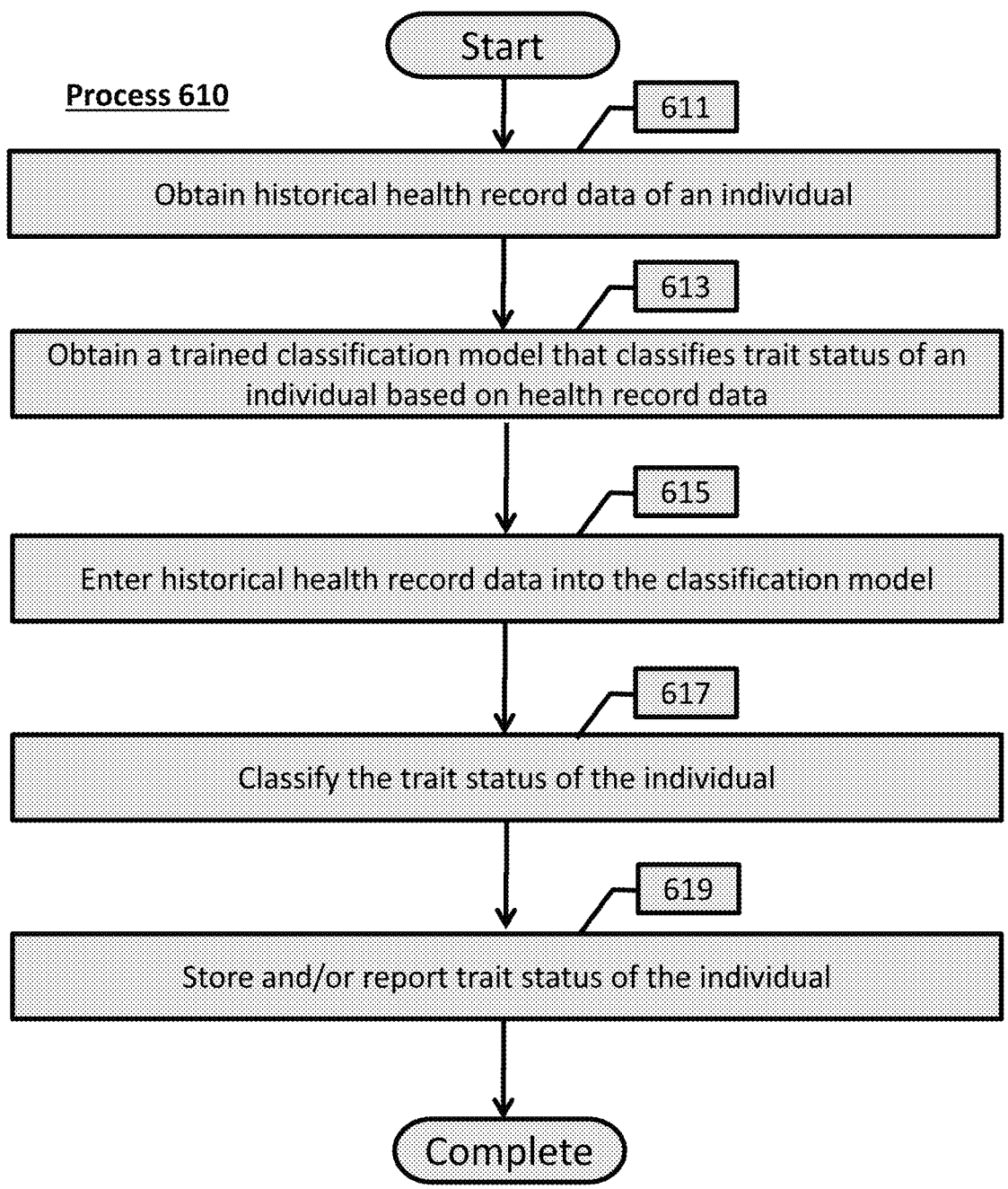

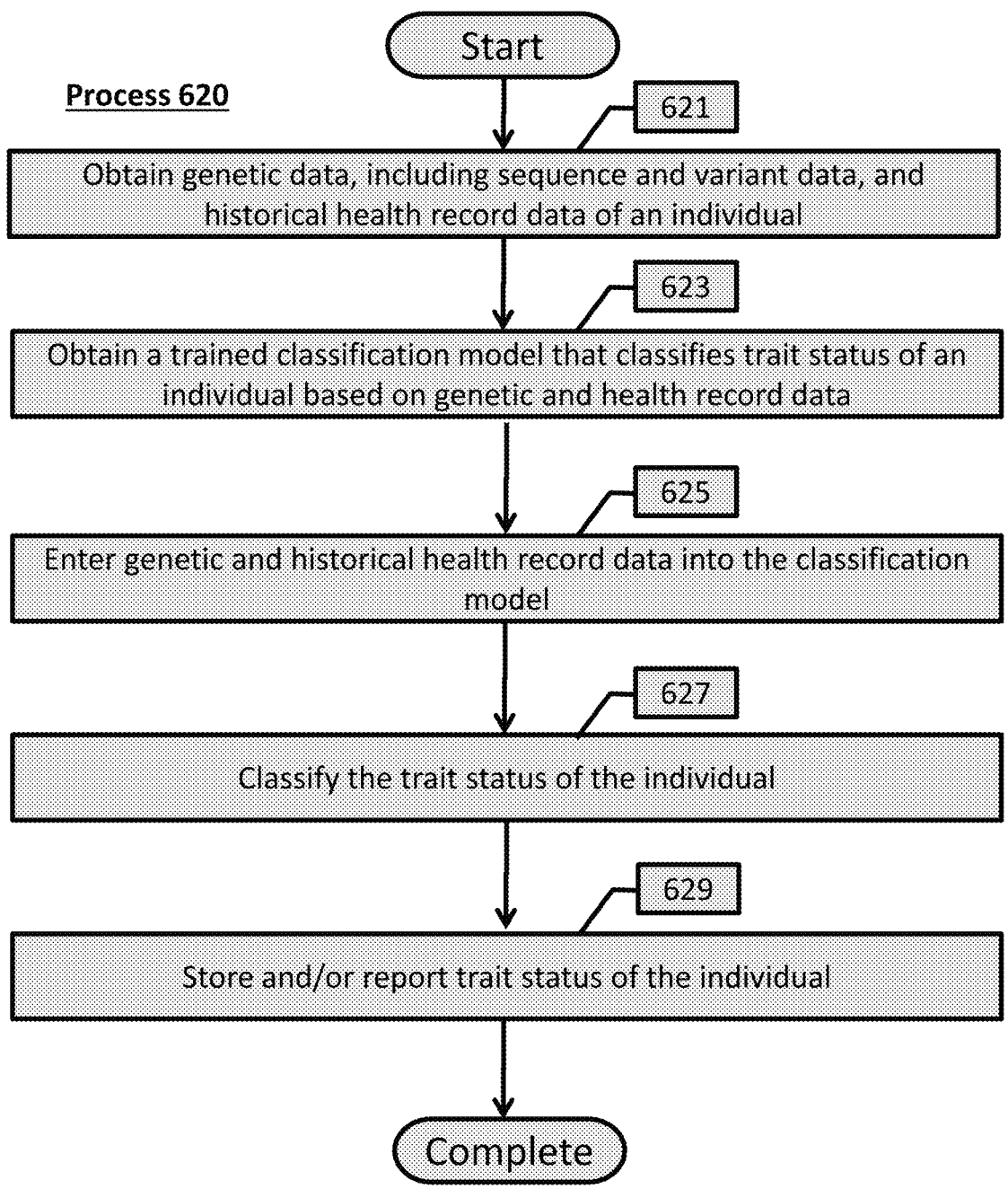

HEAL: Hierarchical Estimate from Agnostic Learning

Fig. 17
Patient: VA00524
Aneurysm size: 20.1 mm
Prediction score: 0.16
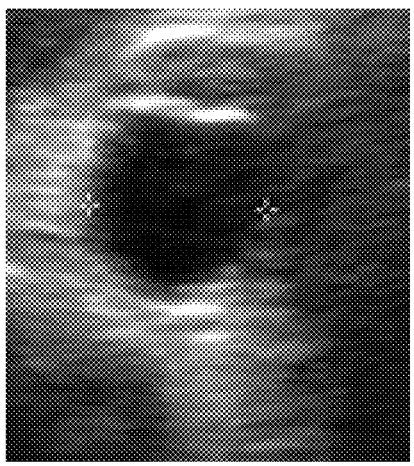
Patient: VA00543
Aneurysm size: 31.2 mm
Prediction score: 0.55
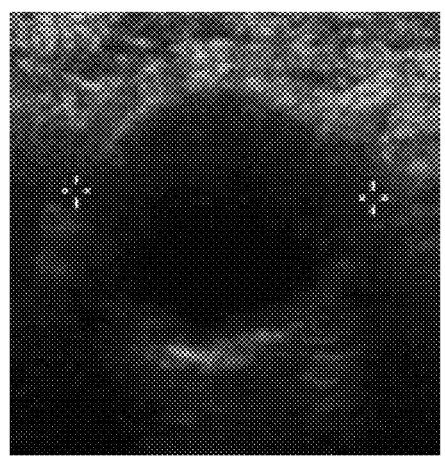
Patient: VA00186
Aneurysm size: 30.0 mm
Prediction score: 0.43
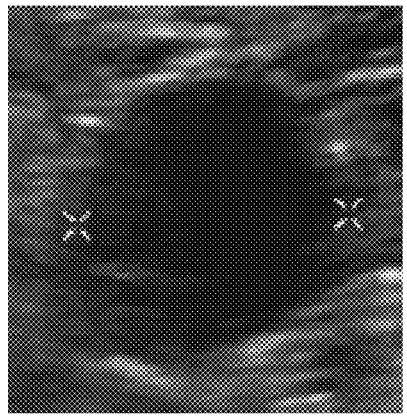
Patient: VA00264
Aneurysm size: 51.2 mm
Prediction score: 0.68
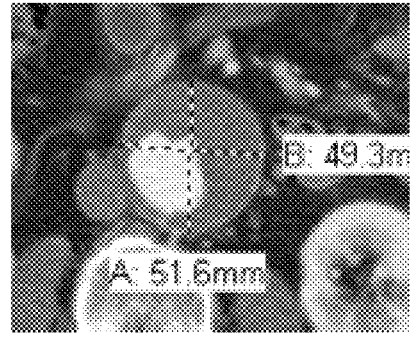

Fig. 19B

| Genome | Prediction Threshold | | | | |
|---|---|---|---|---|---|
| | 0.3 | 0.4 | 0.5 | 0.6 | 0.7 |
| True Positive Rate | 0.88 | 0.81 | 0.73 | 0.67 | 0.55 |
| True Negative Rate | 0.3 | 0.38 | 0.49 | 0.62 | 0.71 |
| False Positive Rate | 0.7 | 0.62 | 0.51 | 0.38 | 0.29 |
| False Negative Rate | 0.12 | 0.19 | 0.27 | 0.33 | 0.45 |

| EHR | Prediction Threshold | | | | |
|---|---|---|---|---|---|
| | 0.3 | 0.4 | 0.5 | 0.6 | 0.7 |
| True Positive Rate | 0.91 | 0.82 | 0.74 | 0.62 | 0.44 |
| True Negative Rate | 0.44 | 0.56 | 0.66 | 0.8 | 0.88 |
| False Positive Rate | 0.56 | 0.44 | 0.34 | 0.2 | 0.12 |
| False Negative Rate | 0.09 | 0.18 | 0.26 | 0.38 | 0.56 |

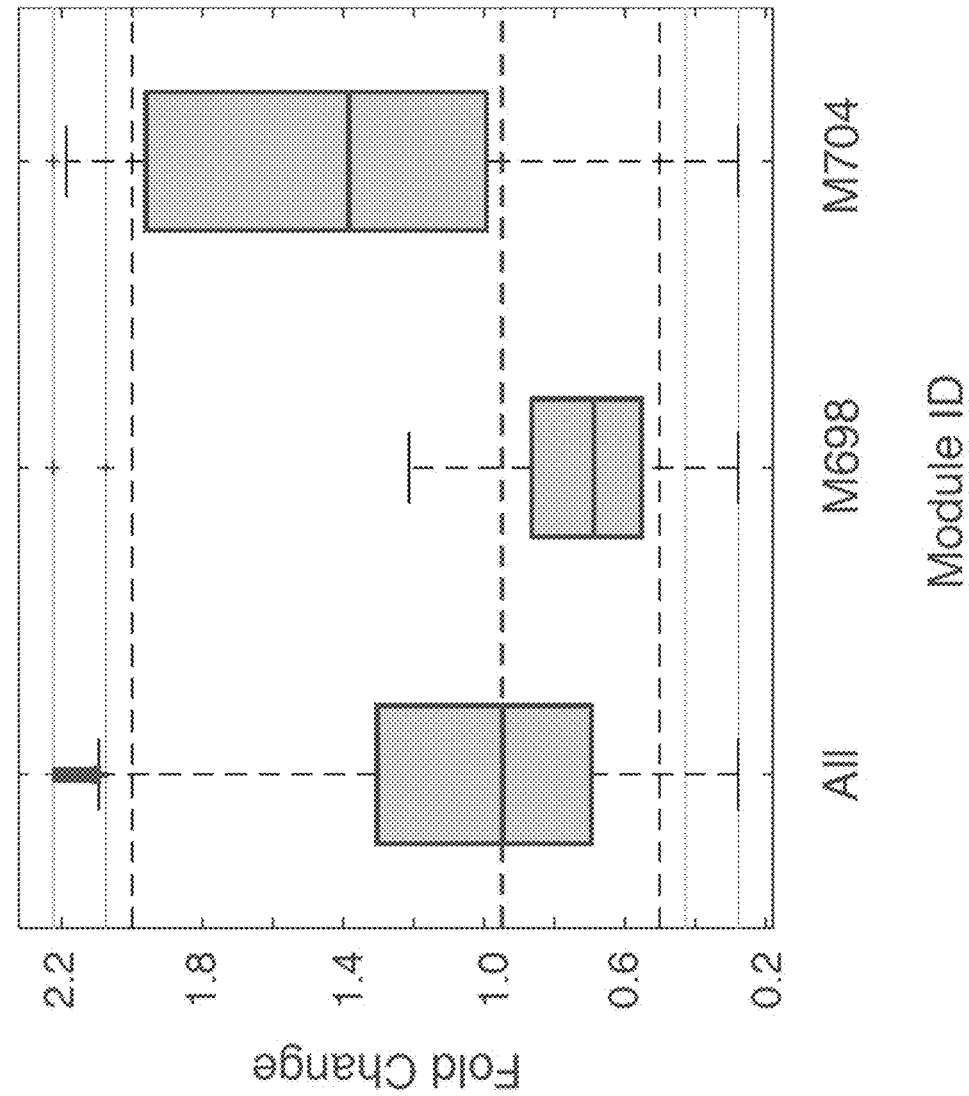

PROCESSES FOR GENETIC AND CLINICAL DATA EVALUATION AND CLASSIFICATION OF COMPLEX HUMAN TRAITS

CROSS REFERENCE TO RELATED APPLICATIONS

This application is a national stage of PCT Patent Application No. PCT/US2019/012848, entitled "Processes for Genetic and Clinical Data Evaluation and Classification of Complex Human Traits" to Li et al., filed Jan. 9, 2019, which claims priority to U.S. Provisional Application Ser. No. 62/615,304 entitled "Processes for Genetic and Clinical Data Evaluation and Classification of Complex Human Traits," to Li et al., filed Jan. 9, 2018, and U.S. Provisional Application Ser. No. 62/727,260 entitled "Processes for Genetic and Clinical Data Evaluation and Classification of Complex Human Traits," to Li et al., filed Sep. 5, 2018, each of which are herein incorporated by reference in their entireties.

STATEMENT REGARDING FEDERALLY SPONSORED RESEARCH OR DEVELOPMENT

This invention was made with Government support under contract HL083800 awarded by the National Institutes of Health. The Government has certain rights in the invention.

FIELD OF THE INVENTION

The invention is generally directed to processes for genetic and clinical data evaluation, and more specifically to methods and systems for classifying genetic and clinical data and data of individuals involving complex human traits and/or disorders and applications thereof.

BACKGROUND

A variety of traits and disorders are complex in nature. Complex traits, which include complex diseases (also referred to as multifactorial disorders), are caused by genetic, environmental, lifestyle, and clinical factors, many of which are extremely difficult to elucidate. Despite their complexity, most of these traits have a high likelihood of inheritance passed down through familial lineages. However, unlike many monogenic congenital traits (i.e., inheritable traits linked to a single gene mutation) that have a recognizable pattern of Mendelian inheritance, complex traits have an obscured pattern of inheritance.

Many complex diseases are known to have a familial connection. These diseases include abdominal aortic aneurysm, Alzheimer disease, arthritis, asthma, bipolar disorder, autism spectrum disorder, cancer, cleft lip and/or palate, coronary artery disease, Crohn's disease, dementia, depression, diabetes (type II), heart disease, heart failure, high cholesterol, hypertension, hypothyroidism, irritable bowel syndrome, obesity, osteoporosis, Parkinson disease, rhinitis (allergic and nonallergic), psoriasis, multiple sclerosis, schizophrenia, sleep apnea, spina bifida, stroke, and many more.

The genetic factor of complex diseases is likely polygenic (i.e., genetic contribution from multiple genes). To better understand the genetic factor, genome-wide association studies (GWAS) have become popular in the genetics field. A GWAS is an examination of the whole genome (or at least the entire exome) of a multitude of individuals to identify genetic variants related to various traits between various cohorts of individuals. Often, a cohort of individuals having one trait (e.g., affected patient) is compared with a cohort of individuals not having the trait (e.g., unaffected individual). The genetic variants examined include single nucleotide variants (SNVs), insertions and deletions (indels), and other polymorphisms. Statistically significant differences in a genetic variant found in a trait-containing cohort could indicate a linkage between the trait of the affected individuals and that particular variant.

Despite the popularity of GWAS studies, it has been difficult to identify and define the genetic patterns underlying complex traits. This is likely because genetic variants associated with complex traits do not singularly result in the trait, but have an influence toward the trait. In addition, many of the genetic variants involved in trait manifestation are not common (e.g., minor allele frequency (MAF)<5%), and identification of uncommon and even rare genetic variants that influence a trait has proven arduous.

SUMMARY OF THE INVENTION

Embodiments are directed towards processes that classify genetic and clinical data and data of individuals involving complex human traits and/or disorders, diagnoses, and treatments.

An embodiment is directed towards a method of treating a complex disorder. The method sequences or has sequenced genetic material of an individual that includes a set of genes. The set of genes contains a variant pattern. The method also obtains or has obtained sequencing or having sequenced genetic material of an individual that includes a set of genes, wherein the set of genes contains a variant pattern. The method also determines or has determined, utilizing the trained computational classification model, a diagnosis of the individual by entering the individual's sequenced genetic material into the trained computational classification model. The diagnosis is determined by an aggregated variant burden score of the set of genes. When the individual is determined to have a diagnosis indicating a propensity for the complex disorder, the individual is treated for the complex disorder.

In another embodiment, the computational classification model has been trained with genetic data of a first cohort of patients having the complex disorder and a cohort of patients not having the disorder.

In yet another embodiment, the set of genes were identified by the computational classification model.

In a further embodiment, the computational classification model has been trained with genetic data of a first cohort of patients having the complex disorder and a cohort of patients not having the disorder. The set of genes were identified based upon a difference in variant patterns between the first cohort of patients having the complex disorder and the first cohort of patients not having the disorder.

In still yet another embodiment, set of genes were identified based upon a difference in variant patterns between the first cohort of patients having the complex disorder and the first cohort of patients not having the disorder.

In yet a further embodiment, the genetic material of the individual is derived from a biopsy of the individual.

In an even further embodiment, the set of genes is identified by the computational classification model to be a minimal set of genes that optimally distinguish individual having the complex trait to individual not having the complex trait.

In yet an even further embodiment, the variant pattern includes rare variants as defined by their minor allele frequency.

In still yet an even further embodiment, the rare variants have a minor allele frequency selected from: less than or equal to 5% and less than or equal to 1%.

In still yet an even further embodiment, the cohort first cohort of patients having the complex disorder and the first cohort of patients lacking the disorder each include a number of individuals selected from: less than or equal to 500, less than or equal to 250, and less than or equal to 150.

In still yet an even further embodiment, the complex disorder is on a phenotypic spectrum.

In still yet an even further embodiment, the computational classification model has been trained with genetic data of at least a second cohort of patients having the complex disorder.

In still yet an even further embodiment, the first cohort of patients having the complex disorder have a more severe phenotype than the second cohort of patients having the complex disorder.

In still yet an even further embodiment, the deleteriousness of variants is an effect on the protein product the gene encodes.

In still yet an even further embodiment, the deleteriousness effect of a variant includes variants that are missense, are nonsense, and affect protein splicing.

In still yet an even further embodiment, the deleteriousness of variants is scored using a computational tool selected from: VEST3, MetaLR, and M-CAP.

In still yet an even further embodiment, the variant burden score is calculated for each gene as follows:

$$g_i = \sum_{j=1}^{n_i} s_{ij}$$

such that $n_i$ is the number of variants in gene i and $s_{ij}$ is the average deleteriousness score for each variant j.

In still yet an even further embodiment, trait-risk coefficients are computed for each gene with the set of genes, and wherein each trait-risk coefficients measure the contribution of variant burden of each gene to diagnostic status.

In still yet an even further embodiment, diagnostic status is based upon:

$$\hat{y}_n = P(y_n = 1 \mid x_n) = \sigma(w^T x_n) = \frac{1}{1 + \exp(-w^T x_n)}$$

such that an individual n has a gene trait burden profile $x_n$ and $\sigma(\bullet)$ is a sigmoid function.

In still yet an even further embodiment, the computational classification model utilizes a sparse learning technique.

In still yet an even further embodiment, the computational classification model is a penalized linear classification model.

In still yet an even further embodiment, the penalized linear classification model utilizes a logistic regression version of least absolute shrinkage and selection operator (LASSO).

In still yet an even further embodiment, a penalty term is $L_1$ calculated:

$$\min_w \mathcal{L}_2(w) = \min_w \mathcal{L}_1(w) + \lambda \|w\|_1$$

such that the $L_1$ norm induced a sparse structure, the parameter tuned the level of sparsity of the solution and can be set to user defined number.

In still yet an even further embodiment, the penalty term is utilized to identify the set of genes to distinguish individuals having a complex disorder from individuals not having the complex disorder.

In still yet an even further embodiment, the genetic material is derived the individual's DNA, and wherein the DNA is on of: genomic or exomic.

In still yet an even further embodiment, the sequencing is performed by capture sequencing.

In still yet an even further embodiment, the complex disorder has no single variant that is diagnostic.

In still yet an even further embodiment, the trained computation classification model determines a diagnosis without prior information.

In still yet an even further embodiment, the complex disorder is selected from the group consisting of: abdominal aortic aneurysm, Alzheimer disease, arthritis, asthma, bipolar disorder, autism spectrum disorder, cancer, cleft lip and/or palate, coronary artery disease, Crohn's disease, dementia, depression, diabetes, heart disease, heart failure, high cholesterol, hypertension, hypothyroidism, irritable bowel syndrome, obesity, osteoporosis, Parkinson disease, rhinitis, psoriasis, multiple sclerosis, schizophrenia, sleep apnea, spina bifida, and stroke.

In still yet an even further embodiment, the method further obtains or has obtained health record data of the individual, and the classification model has been trained with health record data of the first cohort of patients having the complex disorder and the cohort of patients lacking the disorder. The diagnosis of the individual is based upon an accumulated trait-risk coefficient for each measurement in the health record data.

In still yet an even further embodiment, the health record data includes measurements of at least one of: sex, age, weight, body fat, smoking history, drinking history, substance abuse history, blood pressure, heart rate, glucose levels, insulin levels, cholesterol levels, and triglycerides.

In still yet an even further embodiment, the treatment is prophylactic.

An embodiment is directed towards a method of treating a complex order. The method sequences or has sequenced genetic material of an individual that includes a set of genes. The set of genes contains a variant pattern. The set of genes were identified by a computational classification model to distinguish individuals having a complex disorder from individuals not having the complex disorder based upon the variant pattern in the set of genes. The computational classification model has been trained with genetic data of a first cohort of patients having the complex disorder and a cohort of patients lacking the disorder. The method also obtains has obtained health record data of the individual. The method further obtains or has obtained the classification model. The classification model has been trained with health record data of the first cohort of patients having the complex disorder and the cohort of patients lacking the disorder. The method further determines or has determined, utilizing the trained computational classification model, a diagnosis of the individual by entering the individual's sequenced genetic material and the individual's health record data into the trained computational classification model. The diagnosis of the individual is based upon an aggregated variant burden score calculated for the set of genes. Each gene's variant burden score is based upon the deleteriousness and frequency of variants within the set of genes. When the individual is determined to have a diagnosis indicating a propensity for the complex disorder, the individual is treated for the complex disorder.

In another embodiment, the genetic material of the individual is derived from a biopsy of the individual.

In yet another embodiment, the set of genes is identified by the computational classification model to be a minimal set of genes that optimally distinguish individual having the complex trait to individual not having the complex trait.

In a further embodiment, the variant pattern includes rare variants as defined by their minor allele frequency.

In still yet another embodiment, the rare variants have a minor allele frequency selected from: less than or equal to 5% and less than or equal to 1%.

In yet a further embodiment, the cohort first cohort of patients having the complex disorder and the first cohort of patients lacking the disorder each include a number of individuals selected from: less than or equal to 500, less than or equal to 250, and less than or equal to 150.

In an even further embodiment, the complex disorder is on a phenotypic spectrum.

In yet an even further embodiment, the computational classification model has been trained with genetic data of at least a second cohort of patients having the complex disorder.

In still yet an even further embodiment, the first cohort of patients having the complex disorder have a more severe phenotype than the second cohort of patients having the complex disorder.

In still yet an even further embodiment, the deleteriousness of variants is an effect on the protein product the gene encodes.

In still yet an even further embodiment, the deleteriousness effect of a variant includes variants that are missense, are nonsense, and affect protein splicing.

In still yet an even further embodiment, the deleteriousness of variants is scored using a computational tool selected from: VEST3, MetaLR, and M-CAP.

In still yet an even further embodiment, the variant burden score is calculated for each gene as follows:

$$g_i = \sum_{j=1}^{n_i} s_{ij}$$

such that $n_i$ is the number of variants in gene i and $s_{ij}$ is the average deleteriousness score for each variant j.

In still yet an even further embodiment, trait-risk coefficients are computed for each gene with the set of genes, and wherein each trait-risk coefficients measure the contribution of variant burden of each gene to diagnostic status.

In still yet an even further embodiment, diagnostic status is based upon:

$$\hat{y}_n = P(y_n = 1 \mid x_n) = \sigma(w^T x_n) = \frac{1}{1 + \exp(-w^T x_n)}$$

such that an individual n has a gene trait burden profile $x_n$ and $\sigma(\cdot)$ is a sigmoid function.

In still yet an even further embodiment, the computational classification model utilizes a sparse learning technique.

In still yet an even further embodiment, the computational classification model is a penalized linear classification model.

In still yet an even further embodiment, the penalized linear classification model utilizes a logistic regression version of least absolute shrinkage and selection operator (LASSO).

In still yet an even further embodiment, a penalty term is $L_1$ calculated:

$$\min_w \mathcal{L}_2(w) = \min_w \mathcal{L}_1(w) + \lambda \|w\|_1$$

such that the $L_1$ norm induced a sparse structure, the parameter tuned the level of sparsity of the solution and can be set to user defined number.

In still yet an even further embodiment, the penalty term is utilized to identify the set of genes to distinguish individuals having a complex disorder from individuals not having the complex disorder.

In still yet an even further embodiment, the health record data includes measurements of at least one of: sex, age, weight, body fat, smoking history, drinking history, substance abuse history, blood pressure, heart rate, glucose levels, insulin levels, cholesterol levels, and triglycerides.

In still yet an even further embodiment, the genetic material is DNA consisting of: a genome, an exome, or the set of genes.

In still yet an even further embodiment, the genetic material is DNA consisting of: an exome or the set of genes, and wherein the sequencing is performed by capture sequencing.

In still yet an even further embodiment, the complex disorder has no single variant that is diagnostic.

In still yet an even further embodiment, the trained computation classification model determines a diagnosis without prior information.

In still yet an even further embodiment, the complex disorder is selected from the group consisting of: abdominal aortic aneurysm, Alzheimer disease, arthritis, asthma, bipolar disorder, autism spectrum disorder, cancer, cleft lip and/or palate, coronary artery disease, Crohn's disease, dementia, depression, diabetes, heart disease, heart failure, high cholesterol, hypertension, hypothyroidism, irritable bowel syndrome, obesity, osteoporosis, Parkinson disease, rhinitis, psoriasis, multiple sclerosis, schizophrenia, sleep apnea, spina bifida, and stroke.

In still yet an even further embodiment, the treatment is prophylactic.

An embodiment is directed towards a method of treating abdominal aortic aneurysm. The method obtains or has obtained a trained classification model to distinguish individuals having abdominal aortic aneurysm from individuals not having abdominal aortic aneurysm based upon the variant pattern in the set of genes. The method determines or has determined, utilizing the trained computational classification model, a diagnosis of the individual by entering the individual's sequenced genetic material into the trained computational classification model. The diagnosis is determined by an aggregated variant burden score calculated for each gene within the set of genes. When the individual is determined to have a diagnosis indicating a propensity for abdominal aortic aneurysm, the individual is treated for abdominal aortic aneurysm In another embodiment, the computational classification model has been trained with genetic data of a first cohort of patients having abdominal aortic aneurysm and a cohort of patients not having abdominal aortic aneurysm.

In yet another embodiment, the set of genes were identified by the computational classification model.

In a further embodiment, the computational classification model has been trained with genetic data of a first cohort of patients having abdominal aortic aneurysm and a cohort of patients not having abdominal aortic aneurysm. The set of genes were identified based upon a difference in variant patterns between the first cohort of patients having abdominal aortic aneurysm and the cohort of patients not having abdominal aortic aneurysm.

In still yet another embodiment, each gene's variant burden score is based upon the deleteriousness and frequency of variants within the gene. In yet a further embodiment, In an even further embodiment, the genetic material of the individual is derived from a biopsy of the individual.

In yet an even further embodiment, the set of genes is identified by the computational classification model to be a minimal set of genes that optimally distinguish individual having the complex trait to individual not having the complex trait.

In still yet an even further embodiment, the set of genes includes (HNRNPCL1, HNRNPCL3, or HNRNPCL4), KCNC3, HLA-DQB2, TYRO3, PYGM, FAM205A, AIRE, NOMO1, VPS13C, FAM8A1, CACNA1B, NEB, KRTAP4-3, CNTN5, SIRPA, SLC12A3, POTEE, ZNF469, AGAP3, IGFN1, (KCNJ12 or KCNJ18), PSPH, COL5A, MYH7B, POLR2J3, HKDC1, PLEKHH1, SCRIB, KRT86, (SCGB1C1 or SCGB1C2), MYO15A, GOLGA8A, DHX34, ARSD, POTEM, FAM136A, OTOG, RFPL4AL1, SCN10A, PKP3, NBPF10, CPT1B, (LILRA6 or LILRB3), MUC2, TULP4, TPSB2, PCDH11Y, NPIPB15, HLA-DQA1, PABPC1, HLA-DQB1, MAGEC1, CYP2D6, NOTCH2, ITGAE, OR4A16, PRB4, ABCC1, and HLA-B.

In still yet an even further embodiment, the set of genes includes (HNRNPCL1, HNRNPCL3, or HNRNPCL4), KCNC3, HLA-DQB2, TYRO3, PYGM, FAM205A, AIRE, NOMO1, VPS13C, FAM8A1, CACNA1B, NEB, KRTAP4-3, CNTN5, SIRPA, SLC12A3, POTEE, ZNF469, AGAP3, IGFN1, (KCNJ12 or KCNJ18), PSPH, COL5A, MYH7B, POLR2J3, HKDC1, PLEKHH1, SCRIB, KRT86, and (SCGB1C1 or SCGB1C2).

In still yet an even further embodiment, the set of genes includes (HNRNPCL1, HNRNPCL3, or HNRNPCL4), KCNC3, HLA-DQB2, TYRO3, PYGM, FAM205A, AIRE, NOMO1, VPS13C, FAM8A1, CACNA1B, NEB, KRTAP4-3, CNTN5, SIRPA, SLC12A3, POTEE, ZNF469 AGAP3, and IGFN1.

In still yet an even further embodiment, the set of genes includes (HNRNPCL1, HNRNPCL3, or HNRNPCL4), KCNC3, HLA-DQB2, TYRO3, PYGM, FAM205A, AIRE, NOMO1, VPS13C, and FAM8A1.

In still yet an even further embodiment, the set of genes includes (HNRNPCL1, HNRNPCL3, or HNRNPCL4), KCNC3, HLA-DQB2, TYRO3, and PYGM.

In still yet an even further embodiment, the variant pattern includes rare variants as defined by their minor allele frequency.

In still yet an even further embodiment, the rare variants have a minor allele frequency selected from: less than or equal to 5% and less than or equal to 1%.

In still yet an even further embodiment, the rare variants have a minor allele frequency selected from: less than or equal to 5% and less than or equal to 1%.

In still yet an even further embodiment, the complex disorder is on a phenotypic spectrum.

In still yet an even further embodiment, the computational classification model has been trained with genetic data of at least a second cohort of patients having the complex disorder.

In still yet an even further embodiment, the first cohort of patients having the complex disorder have a more severe phenotype than the second cohort of patients having the complex disorder.

In still yet an even further embodiment, the deleteriousness of variants is an effect on the protein product the gene encodes.

In still yet an even further embodiment, the deleteriousness effect of a variant includes variants that are missense, are nonsense, and affect protein splicing.

In still yet an even further embodiment, the deleteriousness of variants is scored using a computational tool selected from: VEST3, MetaLR, and M-CAP.

In still yet an even further embodiment, the variant burden score is calculated for each gene as follows:

$$g_i = \sum_{j=1}^{n_i} s_{ij}$$

such that $n_i$ is the number of variants in gene i and $s_{ij}$ is the average deleteriousness score for each variant j.

In still yet an even further embodiment, trait-risk coefficients are computed for each gene with the set of genes, and wherein each trait-risk coefficients measure the contribution of variant burden of each gene to diagnostic status.

In still yet an even further embodiment, diagnostic status is based upon:

$$\hat{y}_n = P(y_n = 1 \mid x_n) = \sigma(w^T x_n) = \frac{1}{1 + \exp(-w^T x_n)}$$

such that an individual n has a gene trait burden profile $x_n$ and $\sigma(\cdot)$ is a sigmoid function.

In still yet an even further embodiment, the computational classification model utilizes a sparse learning technique.

In still yet an even further embodiment, the computational classification model utilizes a sparse learning technique.

In still yet an even further embodiment, the computational classification model is a penalized linear classification model.

In still yet an even further embodiment, the penalized linear classification model utilizes a logistic regression version of least absolute shrinkage and selection operator (LASSO).

In still yet an even further embodiment, a penalty term is $L_1$ calculated:

$$\min_w \mathcal{L}_2(w) = \min_w \mathcal{L}_1(w) + \lambda \|w\|_1$$

such that the $L_1$ norm induced a sparse structure, the parameter $\lambda$ tuned the level of sparsity of the solution and can be set to user defined number.

In still yet an even further embodiment, the penalty term is utilized to identify the set of genes to distinguish individuals having a complex disorder from individuals not having the complex disorder.

In still yet an even further embodiment, the genetic material is DNA consisting of: a genome, an exome, or the set of genes.

In still yet an even further embodiment, the genetic material is DNA consisting of: an exome or the set of genes, and wherein the sequencing is performed by capture sequencing.

In still yet an even further embodiment, the complex disorder has no single variant that is diagnostic.

In still yet an even further embodiment, the trained computation classification model determines a diagnosis without prior information In still yet an even further embodiment, the method further obtains or has obtained health record data of the individual, and the classification model has been trained with health record data of the first cohort of patients having the complex disorder and the cohort of patients lacking the disorder. The diagnosis of the individual is based upon an accumulated trait-risk coefficient for each measurement in the health record data.

In still yet an even further embodiment, the health record data includes measurements of at least one of: sex, age, weight, body fat, smoking history, drinking history, substance abuse history, blood pressure, heart rate, glucose levels, insulin levels, cholesterol levels, and triglycerides.

In still yet an even further embodiment, treating the individual includes administration of co-enzyme Q.

Several embodiments are directed to processes to evaluation of genetic data yielding a subset of genes that signify a trait. Accordingly, an embodiment is directed to a method for evaluating genetic data to classify a complex trait with a set of variant burdened genes. The method retrieves, using computer systems, genetic data including gene sequence data and rare variant data of at least two cohorts of individuals, wherein at least one cohort is defined by having a particular trait. The method annotates, using the computer systems, each rare variant within the rare variant data of each cohort to describe its deleteriousness effect on protein expression, its cohort association, and its frequency within a cohort. The method determines, using the computer systems, a burden of each rare variants of each gene in relation to each cohort, wherein the variant burden is a cumulative effect of deleteriousness and cohort frequency of variants in each respective gene. The method converts, using computer systems, the burden, frequency, and cohort association into a vector to yield a rare variant burden profile for each cohort. The method trains, using the computer systems, a penalized linear classification model utilizing the rare variant burden profile burden of each cohort to classify trait status of each individual in each cohort. The method classifies using the computer system, a subset of genes of the genetic data as having an increased burden of trait-related variants utilizing the trained penalized linear model and trait status of each individual. The method also produces, using the computer systems, a report of the set of genes having an increased burden of trait-related variants.

Several embodiments are directed to processes to classify an individual in relation to a trait. Accordingly, an embodiments is directed to a method for classifying an individual with a trait status. The method retrieves, using computer systems, genetic data including gene sequence data and variant data of an individual. The method retrieves, using the computer systems, a trained linear classification model, wherein the linear classification model was trained by retrieving, using computer systems, genetic data comprising gene sequence data and rare variant data of at least two cohorts of individuals, wherein at least one cohort is defined by having a particular trait; annotating, using the computer systems, each rare variant within the rare variant data of each cohort to describe its deleteriousness effect on protein expression, its cohort association, and its frequency within a cohort; determining, using the computer systems, a burden of each rare variants of each gene in relation to each cohort, wherein the variant burden is a cumulative effect of deleteriousness and cohort frequency of variants in each respective gene; converting the burden, frequency, and cohort association into a vector to yield a rare variant burden profile for each cohort using the computer systems; and training, using the computer systems, a penalized linear classification model utilizing the rare variant burden profile burden of each cohort to classify trait status of each individual in each cohort. The method enters, using the computer systems, the retrieved genetic data of the individual into the trained linear classification model. The method classifies, using the computer systems, an individual with a trait status for the particular trait utilizing the trained classification model. The method also produces, using the computer systems, a report of the trait status of the individual.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

FIG. 4 provides a process to identify a minimal set of variant burdened genes signifying a trait in accordance with an embodiment of the invention.

FIG. 5 provides a process to train a linear classification model based on historical health record data in accordance with an embodiment of the invention.

FIGS. 6A-6C each provide a process to classify the trait status of an individual in accordance with an embodiment of the invention.

FIG. 17 provides exemplary ultrasound images of aneurisms utilized in accordance with various embodiments of the invention.

FIG. 19B provides tables detailing true positive, true negative, false positive and false negative rates achieved by genome and HER models at varying prediction thresholds generated in accordance with various embodiments of the invention.

FIG. 30 provides a graph detailing altered transcription levels of genes in various HEAL identified modules in PPE mouse model of AAA generated in accordance with various embodiments of the invention.

DETAILED DESCRIPTION

Figure 1:
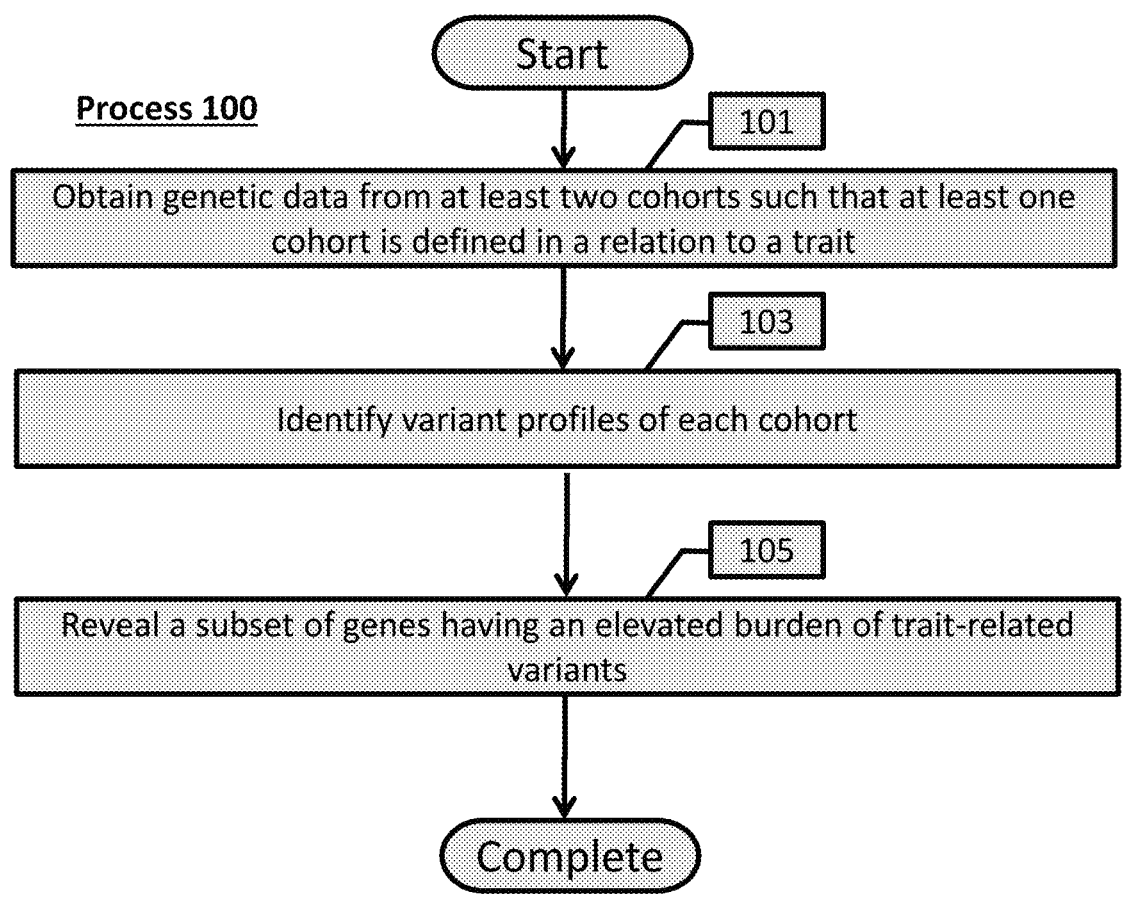
FIG. 1 provides a process to reveal a subset of genes having an elevated burden of trait-related variants in accordance with an embodiment of the invention.

Turning now to the drawings and data, a number of processes for genetic and clinical extrapolation that can be utilized in diagnostics, medicament development, and/or treatments in accordance with various embodiments of the invention are illustrated. In several embodiments, processes encompass computational assessment of genetic and/or clinical data sets to infer hidden relationships between genetic mutations, genes, molecular pathways, enzymatic interactions, and personal health histories. These hidden relationships may be undiscoverable by heuristic and/or traditional genetic methodologies. Various embodiments of the current invention, however, are capable of classifying trait and gene interconnections using an agnostic (i.e., non-assumptive), self-enhancing methodologies. Once classified, methodologies can be utilized in a variety of applications, especially in the areas of diagnostics and treatments.

Historically, the use of genome-wide association studies (GWAS) has not yielded much insight into the genetic contribution in many complex diseases. The loci discovered in GWAS have modest effects on complex disease risk or quantitative variant. This is likely due to the fact that GWASs focus on the identification of common variants (e.g., minor allele frequency (MAF)>5%), ignoring variants that are less frequent. Uncommon and rare variants, however, can be pathogenic.

Sequencing efforts provide a multitude of opportunities to decipher the roles of uncommon and rare variants in complex diseases, however, detection and subsequent analysis of these variants are considerably challenging. Geneticists will often sequence thousands to tens of thousands genomes to find uncommon and rare variants. Larger sequencing sets help improve the statistical power of classical single-variant-based association tests for uncommon and rare variants, however, larger sequencing sets are more difficult to handle and can be quite costly. Thus, it would be ideal to be able to identify uncommon and rare variants and their significance in smaller data sets.

Another common problem associated with complex disorders is that they often exhibit variant heterogeneity (i.e., trait-positive individuals each having a unique or rare collection of variants that may be trait causal). A typical GWAS approach is unable to differentiate robust and replicable trait related variants from nonconsequential variants. Thus, methods that are capable to identify and stratify trait related variants would be preferred.

Methods and embodiments of the invention described herein are capable of overcoming the problems associated with rare variant detection and classification. Various embodiments are directed to examining rare variants using a machine-learning model to directly circumvent the challenge of locus heterogeneity. In some embodiments, the machine-learning model is capable of using the variant data to classify a subset of genes across the human genome that are important for complex disease etiology. Machine-learned models, in accordance with a number embodiments, are also used to further analyze an individual's genome to predict a likelihood of disease manifestation. And in several embodiments, diagnostics and/or treatments are performed based upon a reveal of high likelihood of complex disease manifestation.

In several embodiments, classification methods and/or models described within are agnostic and do not presume any existing knowledge about the traits, individuals and/or cohorts to be examined. A number of embodiments utilize a machine-learning framework that agnostically reveals a subset of genes that classify as related to the trait in question. Many embodiments can utilize a machine-learned model to classify an individual as trait-positive or trait-null solely based on their genetic data. In some embodiments, historical health records are used to classify an individual as trait-positive or trait-null. Some embodiments utilize both genetic data and health record data to classify an individual. Trait classification, in accordance of a number of embodiments, can be used to predict clinical outcomes and/or to initiate medical intervention. Because trait classification is agnostic and completely based on genetic data and/or historical health records, human clinical determination from a licensed physician can be enhanced or even bypassed all together.

In many embodiments, methods described do not require a large number of individuals within a cohort to train a classification model and/or reveal a set of genes related to a particular trait. Unlike standard methodologies that are known and currently practiced, which require thousands to tens of thousands of individuals in both trait-positive and trait-null cohorts to identify genetic variants of consequence, various embodiments merely require a few hundred of individuals in each cohort. In a number of embodiments, the number of individuals necessary for each cohort to identify trait related variants is <500; in many embodiments, <250; and in several embodiments, <150.

Identification of Genes Burdened with Rare Variants Process Overview

A conceptual illustration of a process to reveal a subset of genes related to a particular trait in accordance with an embodiment of the invention is illustrated in FIG. 1. In some embodiments, a process is utilized to reveal a minimal subset of genes that have an elevated burden of variants that are indicative of a particular trait. Revealed subset of genes can be used in various applications downstream in accordance with a number of embodiments of the invention, including (but not limited to) classifying an individual based on their genetic data.

Process 100 begins with obtaining (101) genetic data including gene sequence data and variant data from at least two cohorts, one cohort being defined for having a particular trait and a second cohort defined for lacking that trait. In accordance with various embodiments, sequence data can be derived from a number of sources. In some instances, these sequences are obtained de novo by extracting the DNA from a biological source and sequencing it. Alternatively, genetic sequence data can be obtained from a publicly or privately available database. Many databases exist that store datasets of sequences from which a user can extract the data to perform experiments upon. In many embodiments, the genetic sequence data include complete genomes or exomes, however, any genetic data set as appropriate to the requirements of a given application could be used.

As shown in FIG. 1, sequence data to be obtained should be divided into at least two cohorts. One cohort is a collection of individuals that are defined by a particular trait. The particular trait to be examined depends on the task on hand. For example, if process 100 is used to reveal a subset of genes that are important in an etiology of a particular medical disorder, one cohort should be comprised of patients diagnosed with the disorder and another cohort should be comprised of control individuals (e.g., individuals that have not manifested the disorder). The precise definition of a cohort, however, can vary depending on the application, as would be understood by those skilled in the art.

The number of individuals within a cohort can depend on the application and trait to be examined. It should be noted however, that utilization of machine learning and variant aggregation models within process 100 can reduce the number of individuals necessary to reveal a subset of genes related to trait compared to traditional genetic studies on variants (e.g., GWAS). On the other hand, increasing the number individuals in a cohort can improve machine learning and variant aggregation models. Accordingly, in a number of embodiments, cohorts include anywhere from one hundred to five hundred individuals. In some embodiments, cohort size is greater than five hundred individuals.

Once sequence data are obtained, process 100 identifies (103) variant profiles of each cohort. In many embodiments, a variant is single nucleotide variant (SNV), insertion, or deletion. Accordingly, a profile of variants that exist all along the genetic data set can be determined for each cohort. As millions of variants will exist for each cohort, it may be preferred to trim the profile based on the functionality of the variant. For example, synonymous SNVs are unlikely to have any effect on a particular trait and thus are removed from analysis in accordance with some embodiments. In addition, variants that are known to be related to another trait (e.g., ethnicity) are removed in accordance with some embodiments.

When processes are performed to reveal subsets of genes related to a complex trait, it is likely that a cohort variant profile will include many rare variants (i.e., variants with MAF≤1%). In several classical methodologies used within the prior art, rare variants were excluded from further analysis due to the lack of statistical significance. In accordance with several embodiments as described herein, rare variants are kept in the analysis to determine their effect on trait etiology, even if the variants are statistically insignificant in standard GWAS studies. In some cases, complex traits will have variant profiles only consisting of rare variants. Accordingly, processes in accordance with several embodiments of the invention can still utilize these profiles to train a model capable of revealing a subset of genes related to the trait or classing and individual's trait status.

Process 100 reveals (105) a subset of genes having an elevated burden of trait-related variants using the variant profiles. In several embodiments, a subset of genes are revealed agnostically, without utilization of prior knowledge. In many embodiments, processes for revealing a subset of genes operate on a computational framework that utilizes machine-learning models. In some embodiments, variant profiles of each cohort are used as training data in a machine learning model that is capable of training itself to find genes related to a particular trait. Instead of examining each variant specifically, a model, in accordance with a number of embodiments of the invention, identifies genes having increased burdens of variants based on a cumulative effect of deleterious nonsynonymous variants. In many embodiments, upon training, a model reveals genes that have a greater variant burden in the trait-positive cohort. Thus, the result is a concise list of genes associated with a trait of interest. In several embodiments, the list obtained is a minimal set of genes that provides the optimal combination of genes to predict a trait.

In several embodiments, the trained classification model is utilized in various down-stream applications, including (but not limited to) classification of an individual, treatment of individual and/or development of functional models. These embodiments are described in greater detail in subsequent sections.

Trait-Related Variant Profiles

Figure 2:
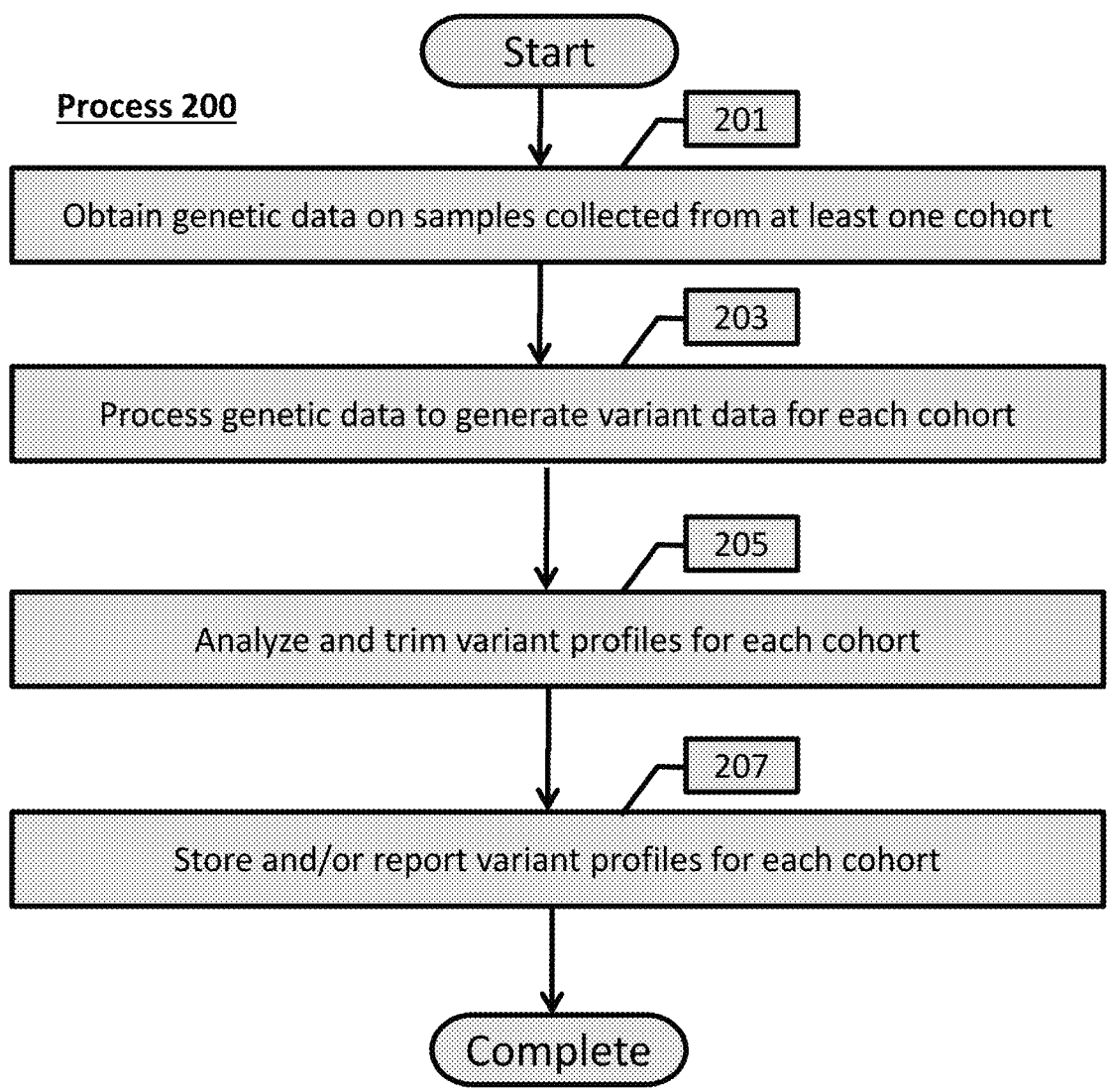
FIG. 2 provides a process to prepare and analyze a variant profile of a cohort in accordance with an embodiment of the invention.

A conceptual illustration of a process to develop variant profiles of at least one cohort utilizing computing systems is provided in FIG. 2. As shown, in a number of embodiments, the process begins by obtaining (201) genetic data from at least one cohort, which can be uploaded and stored via computer systems. In accordance with several embodiments, a cohort is a group of individuals defined by a trait that is shared among the individuals within the cohort. The appropriate definition of a cohort will depend on the trait to be examined. In accordance with several embodiments, at least one cohort is defined as trait-positive for having a trait. It should be noted, however, that some traits may be a spectrum and thus several trait-positive cohorts may be defined, ranging from mild to prominent/severe phenotypes. Accordingly, in some embodiments, multiple cohorts are defined in relation to a spectrum of a trait.

In many embodiments, genetic data to be obtained can be any sequence data that contain genetic variants. In several embodiments, genetic data are full or partial genomes; in some embodiments, genetic data are full or partial exomes. Whole genomes may be preferred when it would be beneficial to identify variants in intronic and intergenic regions in addition to exonic regions. In some embodiments, exome data, covering the coding sequences of the genome, will suffice, as these data likely include a substantial portion of the variants related to a particular trait.

In accordance with various embodiments of the invention, genetic data can be derived from a number of sources. In some embodiments, these sources include sequences derived from DNA of a biological source that are subsequently processed and sequenced. In other embodiments, sequences are obtained from a publicly or privately available database. Many databases exist that store datasets of sequences from which a user can extract the data to perform experiments upon.

In many embodiments, de novo biological samples of DNA can be used for sequencing that are each derived from a biopsy of an individual within a cohort. In particular embodiments, the DNA to be acquired can be derived from biopsies of human patients associated with a phenotype or a disease state. In some embodiments, the DNA can be derived from common research sources, such as in vitro tissue culture cell lines or research mouse models. In many embodiments involving de novo extraction, the DNA molecules are extracted, processed and sequenced according to methods commonly understood in the field.

Regardless of the source of sequencing data, in a number of embodiments, variants are identified from sequencing data that has a large amount of coverage. In some embodiments, 20×, 30×, 40×, 50×, or >50× coverage is performed. In many embodiments, more coverage reduces sequencing error.

Figure 3:
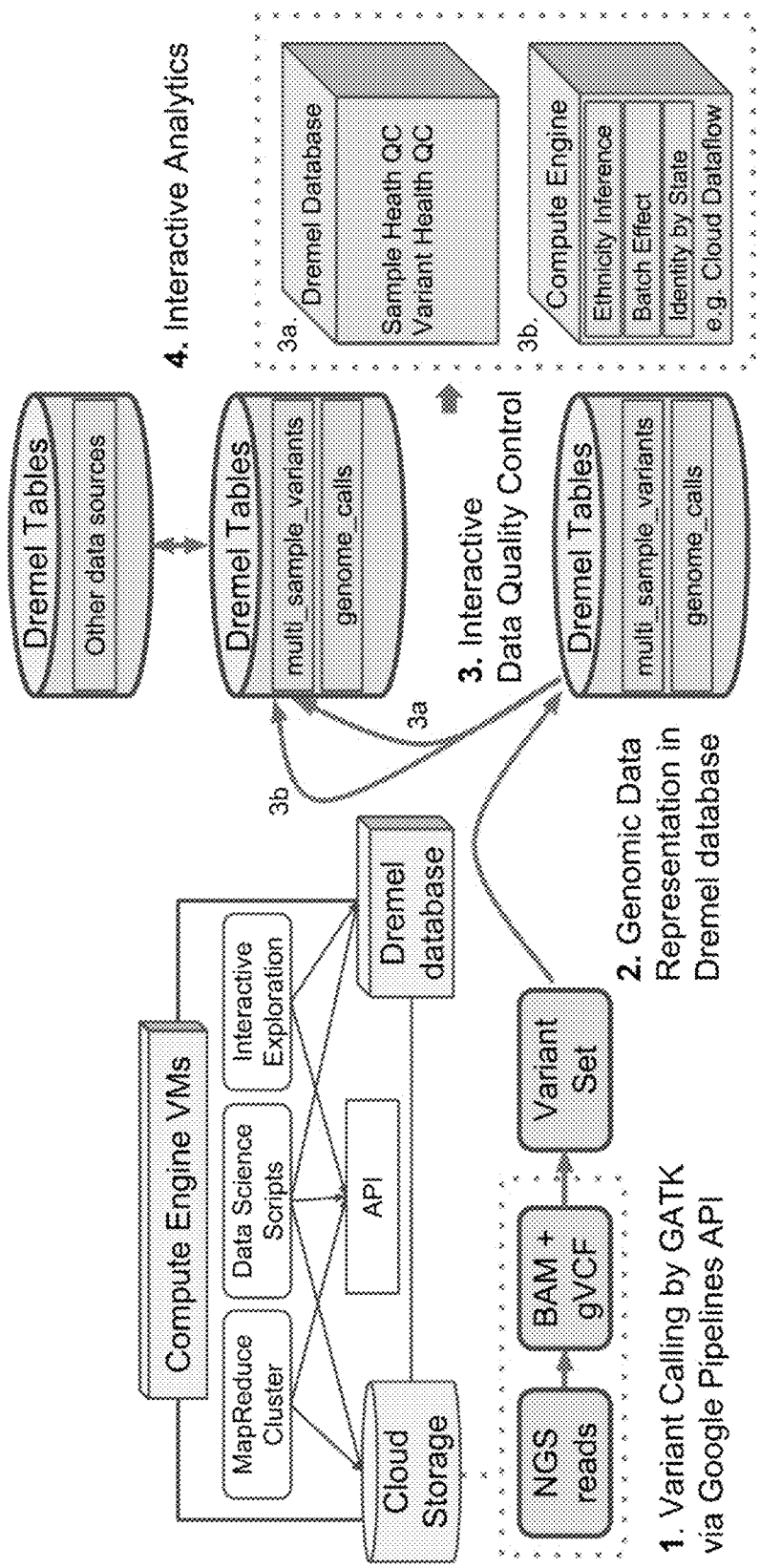
FIG. 3 provides a diagram of a process for analyzing large data sets of genetic sequences in accordance with various embodiments of the invention.

In accordance with various embodiments, genetic data are processed (203) to generate variant profiles for each cohort. Processing the sequence data can be difficult and/or time consuming when a large number of individuals are included within a cohort and a large amount of genetic data coverage is obtained for each individual. Accordingly, embodiments are directed to the use of interactive analytics tool to process large amounts of sequence data. For example, as shown in an embodiment in FIG. 3, interactive analytics can be built on Dremel to perform information compression, comprehensive quality controls and biological information retrieval. This depicted tool implements Apache Drill, Cloudera Impala, Amazon Athena, and Google BigQuery and can provide orders of magnitude faster turnaround for common genomic analysis. For an in depth description of variant processing, please see, Pan, C., et al. *Bioinformatics* 2017, 33, 3709-3715, the disclosure of which is incorporated herein by reference. It should be noted, however, that any database analytical tool capable of handling the amount of data to be analyzed, can be used in accordance with a number of embodiments.

In a number of embodiments, variant profiles are analyzed and trimmed (205) for each cohort. Various embodiments include several different analyses to trim cohort sequence data that can be performed, including (but not limited to), for example:

principal component analysis to determine batch effect among different DNA library preparations (i.e., corrections of differences in benchtop preparation)

comparing data sets between different genotype data methodologies to facilitate high concordance (e.g., deep sequencing data and SNP array data)

verifying that the sex of an individual matches the self-reported sex determining an inbreeding coefficient that infers familial relationships verifying that there is no cross contamination between samples (e.g., computing identity-by-state)

assessing missing calls for each genome assessing the distribution of singleton calls assessing the distribution of heterozygous calls performing admixture analysis to ensure a high percentage of a single ethnicity (e.g., greater than 90% of European heritage)

It should be noted that any, some, or all of these analyses could be performed in accordance with a number of various embodiments. Once analysis is performed, in a number of embodiments, cohort sequence data is trimmed by removing various genomes that do not qualify in accordance to any analysis performed. For example, if the genetic data of individual reveals a sex that does not match the self-reported sex, it may be desirable to not incorporate that genome into the cohort analysis. In an alternative example, if a genome yields an inbreeding coefficient beyond a threshold, then that genome may be removed.

In many embodiments, analysis and trimming can also be performed at the variant level, identifying confident variant calls for further analysis. Many embodiments trim sequence data by analyzing and removing variants for a number of reasons, including, for example, if they:

exist on blacklisted regions are heterozygous haplotypes (e.g., heterozygous call on chromosome X in male genomes)

identify as low quality or poor by variant analysis tools

It should be noted that any, some, or all of these analyses could be performed in accordance with a number of various embodiments.

In many embodiments, variant profiles are further analyzed and trimmed (205), often dependent on the application. For example, in some embodiments, synonymous variants are removed due to the fact that these variants are unlikely to have an effect on a trait. In more embodiments, indels are removed. In some embodiments, only variants of a particular frequency (e.g., rare variants with MAF≤1.0%) are examined and thus all other variants are excluded. In some embodiments, known and/or pre-classified variants from known various databases are removed. For example, when examining variants related to a disorder, it may be ideal to remove known variants that exist in databases of healthy individuals, as it may be reasonable to presume that these variants are not related to a disordered state.

In accordance with several embodiments, variant profiles are stored and/or reported (207). In some embodiments, these profiles may be used in many further downstream applications, including (but not limited to) in a GWAS study and in processes that identify burdened genes.

While a specific example of a process for developing variant profiles is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Depicted in FIG. 4 is a conceptual illustration of a process to identify variant burdened genes signifying a complex trait via a machine-learning framework, which can performed on various computing systems. The hierarchical process utilizes the effects of individual variants, and aggregates the effects of the variants to identify genes that are burdened by the variants. The identified set of genes further signify the biological processes associated with the complex trait. In other words, the framework is a hierarchical genetic system that identifies a set of genes that are commonly affected by rare variants, and when the set of genes are affected beyond a threshold, it results in a disruption of biological pathways that are the causation of the complex trait.

Process 400 begins with obtaining (401) at least two variant profiles derived from two cohorts. In many embodiments, at least one cohort is defined for having a particular trait (e.g., a complex trait). In some embodiments, the cohorts include trait-positive and trait-negative cohorts (e.g., affected patient and healthy control cohorts). It should be noted, however, in accordance with a number of embodiments, that some traits may be on a spectrum and thus several trait-positive cohorts may be defined, ranging from mild to prominent/severe phenotypes. The variant profiles may be obtained by any of a variety of different means.

A variant profile, in accordance with a number of embodiments, is a genetic sequence data set including (but not limited to) variants having rare frequency (e.g., MAF≤1.0%) derived from a cohort of individuals. In many embodiments, a variant profile is a collection of variant data that are descriptive of a particular trait-associated cohort. Accordingly, in many embodiments, variant profiles are derived from cohorts of individuals large enough to obtain a comprehensive collection of variant data. However, in accordance with several embodiments, it is not necessary to have cohort large enough to render the rare variant data significant as defined in a classical GWAS study. In a number of embodiments, the optimal cohort size is determined empirically, dependent on the trait to be examined. In many embodiments, cohort size is between 300 and 500 individuals. In some embodiments, the cohort size is larger than 500 individuals.

In several embodiments, each variant within the profile is annotated (403) to assign their clinical relevance. In many embodiments, each variant is annotated based on their predicted deleteriousness effect (e.g., missense, nonsense, affecting splicing) on a protein. In more embodiments, the functional consequences of the variants and the population frequency of the variants are also considered. The variants can be classified and scored, in accordance with a number of embodiments, utilizing a variety of computational tools, which include, for example, VEST3, MetaLR, and M-CAP. In a number of embodiments, multiple variant annotation tools are used, each generating a deleteriousness score, and the scores are weighted and averaged to estimate the deleteriousness of variants.

In a number of embodiments, the burden of each variant is determined considering their deleteriousness and frequency within a cohort (405). In some embodiments, variant burden is calculated for each gene i (i=1, 2, . . . , $i_{total}$) of genetic data set using the equation:

$$g_i = \sum_{j=1}^{n_1} s_{ij}, \quad \text{(Eq. No. 1)}$$

in which $n_i$ is the number of variants in gene i and $s_{ij}$ is the average deleteriousness score for each variant j and $i_{total}$ is number genes in the data set. In more embodiments, the variant burden profile is determined for each cohort, resulting in a feature vector of $i_{total}$ dimensions per sample:

$$x_n = (g_1, \ldots, g_i, \ldots, g_{17443}), \quad \text{(Eq. No. 2)}$$

where $x_n \in \mathfrak{R}^{itotal}$ and n denotes the nth sample.

In several embodiments, annotated variant profiles are incorporated into the computational framework to train (407) a classification model that can classify trait status of each individual based on a set of genes and variant patterns within the set of genes, where the set of genes are burdened by the variants within. In some embodiments, burdened is to imply that in the cumulative, the variants affect the gene to result in contribution to a complex trait. In accordance with many embodiments, a primary goal of the classification model is to identify a set of genes having increased variant burden, as determined by the deleteriousness and frequency of variants within the set of genes. Accordingly, various embodiments score each gene based on their aggregate variant burden score, comparing trait-positive and trait-negative cohorts.

Various embodiments utilize a penalized linear classification model to prevent overfitting. In some embodiments, a penalized linear classification model agnostically classifies trait status of each individual. In some embodiments, each cohort profile can be defined by pairs $\{x_n, y_n\}$'s s (n=1, . . . , $n_{total}$), wherein $x_n$ is a feature vector, which may be determined by Eq. No. 2, $n_{total}$ is the total number individual in a cohort, and $y_n$ represents the label of a cohort. In some embodiments, $y_n=1$ indicates that the nth sample is positive for a trait, otherwise it is negative.

To model the additive effect of variant burden, in accordance of many embodiments, trait-risk coefficients (e.g., w in Eqs. No. 3-5) are computed for each gene, wherein trait risk coefficients measure the contribution of variant burden of corresponding genes to trait status (e.g., trait-positive). In a number of embodiments, the trait status of an individual can be modeled as:

$$\hat{y}_n = P(y_n = 1 \mid x_n) = \sigma(w^T x_n) = \frac{1}{1 + \exp(-w^T x_n)}, \quad \text{(Eq. No. 3)}$$

where an individual n has gene trait burden profile $x_n$ and $\sigma(\cdot)$ is the sigmoid function. In many embodiments, the optimal trait risk coefficient that achieves the maximum consistency between the model probabilities and the observations for a cohort is determined using logistic regression. In more embodiments, the optimal trait coefficient w that achieves the maximum consistency between the model probabilities and the observations for the cohort is determined applying:

$$\min_w \mathcal{L}_1(w) = \min_w -\frac{1}{N}\sum_{n=1}^{N} y_n \log \hat{y}_n + (1-y_n)\log(1-\hat{y}_n), \quad \text{(Eq. No. 4)}$$

in which the optimization objective is the average cross-entropy of the sample set.

In many embodiments, classification models utilize a sparse learning technique, which may avoid potential overfitting. For example, when there a large number of features that significantly outnumber the training samples, an overfitting problem may arise. According to some embodiments, a parsimonious structure is adopted in the model, in which the minimum number of features is targeted to best explain the observations by introducing a penalty term. In some embodiments, a penalty term $L_1$ can be solved using:

$$\min_w \mathcal{L}_2(w) = \min_w \mathcal{L}_1(w) + \lambda \|w\|_1, \quad \text{(Eq. No. 5)}$$

in which the $L_1$ norm induced a sparse structure, the parameter $\lambda$ tuned the level of sparsity of the solution and can be set to user defined number. In many embodiments, the sparsity of the solution is selected by determining which sparsity achieves the best average AUROC score in cross-validation calculations. In several embodiments, a logistic regression version of least absolute shrinkage and selection operator (LASSO) is used. In some embodiments, Eq. No. 5 can be treated as the logistic regression version of LASSO.

In a number of embodiments, a set of variant burdened genes and variant patterns within the burdened genes signifying a trait is identified (409) using the classification model. In some embodiments, the set of variant burdened genes identified is the minimal number of genes that best distinguish the complex trait from null (i.e., distinguishing the trait-positive cohort from trait-negative cohort). In some embodiments, a penalty term is utilized to identify the set of variant burdened genes that signify a trait of interest based on prediction power. In some embodiments, a set of variant burdened genes that signify a trait are agnostically identified.

In several embodiments, the identity of at least one set of genes burdened by variants is reported and/or stored (411). In additional embodiments, a set of genes is used in a number of downstream applications, including (but not limited to) clinical classification of individuals (e.g., clinical diagnostics), mapping the genes into various networks, further molecular research into the trait, and identification of functional modules. In many embodiments, a trained classification model is used to classify individuals in regards to a trait.

While a specific example of a process for identifying variant burdened genes is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Clinical Data Profiles

Depicted in FIG. 5 is a conceptual illustration of a process to train a penalized linear classification model capable of classifying trait status of an individual on computing systems. In certain embodiments, the process begins with obtaining (501) historical health record data from two cohorts of individuals. In several embodiments, at least one trait-positive cohort is defined. In many embodiments, the cohorts are trait-positive and trait-negative (e.g., affected patient and healthy control cohorts).

In several embodiments, the health records include data that may be relevant to the trait, so that a classification model may learn to associate the clinical data with a particular trait. If the trait is related to health and/or disease, in accordance with many embodiments, cohort data to be obtained can include (but is not limited to) sex, age, weight, body fat, smoking history, drinking history, substance abuse history, etc. If the trait is related to cardiovascular disease and/or diabetes, in accordance with some embodiments, cohort data may include (but is not limited to) blood pressure, heart rate, glucose levels, insulin levels, cholesterol levels, triglycerides, etc. In a number of embodiments, the data to be collected can be varied and tailored to the needs of the classification model to be developed and trained.

In some embodiments, the health record measurement data are annotated (503) in relationship to a trait of interest. Accordingly, in many embodiments, individuals having health record data is assigned to a particular cohort.

In several embodiments, annotated health record data are incorporated into the computational framework to train (505) a classification model to classify trait status of each individual. In some embodiments, a penalized linear classification model to agnostically classify trait status of an individual. To model the additive effect of various measurement data, in accordance with a number of embodiments, a trait risk coefficient is calculated for each measurement, wherein the trait risk coefficient measures the contribution of that particular health measurement to trait status (e.g., trait-positive). In more embodiments, the probability of having a trait is modeled with a sigmoid function, utilizing the health record data for a sample. In many embodiments, the optimal trait risk coefficient that achieves the maximum consistency between the model probabilities and the observations for a cohort is determined using logistic regression, in which the optimization objective is the average cross-entropy of the sample set.

In many embodiments, a classification model utilizes a sparse learning technique, which may avoid potential overfitting. For example, when there are a large number of features that significantly outnumber the training samples, an overfitting problem may arise. According to some embodiments, a parsimonious structure is adopted in the model, in which the minimum number of features is targeted to best explain the observations by introducing a penalty term. In more embodiments, a logistic regression version of LASSO is used.

In numerous embodiments, a classification model is reported and/or stored (507). In additional embodiments, the classification model is used in a number of downstream applications, including (but not limited to) clinical classification of individuals and medical intervention based on the results of the classification model.

While a specific example of a process for training a penalized linear classification model is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Classification of Individuals

FIG. 6A provides a conceptual illustration of a process to classify an individual via computer systems using the individual's genetic sequence data and a trained classification model that has identified a set of genes that distinguishes a particular trait. Various embodiments utilize this process to classify an individual based on whether the individual is likely to have the particular trait. For example, in some applications, process 600 can be used to classify an individual as having a propensity for a particular disease or disorder. And in some applications, an individual can be diagnosed and/or treated utilizing various embodiments of a classification system.

As shown in FIG. 6A, in a number of embodiments, an individual's genetic data, including variant data, are obtained (601). The data, in accordance with many embodiments, is any DNA sequence data of individual that is inclusive of the set of genes identified to distinguish the particular trait to be analyzed. In some embodiments, genetic data is an individual's entire genome, a partial genome (e.g., exome), or other data that include at least a portion of an individual's sequence and variant data. In some embodiments, genetic data is sequencing data on a set of genes that distinguish the trait to be analyzed (e.g., capture sequencing). In some embodiments, sequence data are obtained by a biopsy of an individual, in which genetic material is extracted and sequenced in accordance with various protocols known in the art.

A trained classification model capable of classification of trait status is also obtained (603). In several embodiments, a trained classification model classifies an individual based on the variant pattern with a set of genes that distinguishes a particular trait. In many embodiments, a trained penalized classification model is capable of agnostically classifying trait status. In some embodiments, a trained classification model is trained as shown and described in FIG. 4, however, in accordance with more embodiments, any classification model capable of classifying an individual on trait status based on genetic sequence data may be used. In a number of embodiments, an individual's genetic sequence data are entered (605) into a classification model, wherein subsequently the individual's trait status is classified (607). In some embodiments, the individual's trait status is classified based upon a variant pattern of a set of genes that distinguishes the trait. In some embodiments, a trait-positive diagnosis is based upon an aggregate variant burden score above a threshold as determined by scoring the variant pattern of a set of genes that distinguishes the trait. In some embodiments, a variant burden score is based upon the deleteriousness and frequency of variants within the set of genes that distinguishes the trait. In some embodiments, the individual's trait status is agnostically classified. In some embodiments, the Scikit-learn process is used to implement the classification.

In several embodiments, the trait classification of the individual is reported and/or stored (609). In numerous embodiments, the classification can be used in a number of downstream applications, which may include (but is not limited to) diagnosis of individuals and determination of medical intervention.

While a specific example of a process for classifying individuals is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

FIG. 6B provides a conceptual illustration of a process to classify an individual via computer systems using a trained classification model and the historical health record data. Various embodiments utilize this process to classify an individual of having a particular trait. For example, in some applications, process 610 can be used to classify an individual as having a propensity for a particular disease or disorder. And in some applications, an individual can be diagnosed and/or treated utilizing various embodiments of a classification system.

As shown in FIG. 6B, in a number of embodiments, an individual's health record data are obtained (611). The data, in accordance with many embodiments, is any health record data to be used in a classification model (i.e., health record data used to train the classification model). In some embodiments, health record data includes include (but is not limited to) sex, age, weight, body fat, smoking history, drinking history, substance abuse history, blood pressure, heart rate, glucose levels, insulin levels, cholesterol levels, triglycerides, etc. In a number of embodiments, the data to be collected can be varied and tailored to the needs of the classification model that has been developed and trained.

A trained classification model capable of classification of trait status is also obtained (613). In several embodiments, a trained penalized classification model is capable of agnostically classifying trait status. In some embodiments, a trained classification model is trained as shown and described in FIG. 5, however, in accordance with more embodiments, any classification model capable of classifying an individual on trait status based on genetic sequence data may be used. In a number of embodiments, an individual's health record data are entered (615) into a classification model, wherein subsequently the individual's trait status is classified (617). In some embodiments, trait status is based upon by an accumulated trait-risk coefficient for each measurement in the health record data. In some embodiments, the individual's trait status is agnostically classified. In some embodiments, the Scikit-learn process is used to implement the classification.

To model the additive effect of various measurement data, in accordance with a number of embodiments, a trait risk coefficient is calculated for each measurement, wherein the trait risk coefficient measures the contribution of that particular health measurement to trait status (e.g., trait-positive)

In several embodiments, the trait classification of the individual is reported and/or stored (619). In numerous embodiments, the classification can be used in a number of downstream applications, which may include (but is not limited to) diagnosis of individuals and determination of medical intervention.

While a specific example of a process for classifying individuals is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

FIG. 6C provides a conceptual illustration of a process to classify an individual via computer systems using a trained classification model and the individual's genetic sequence and health record data. Various embodiments utilize this process to classify an individual of having a particular trait. For example, in some applications, process 620 can be used to classify an individual as having a propensity for a particular disease or disorder. And in some applications, an individual can be diagnosed and/or treated utilizing various embodiments of a classification system.

As shown in FIG. 6C, in a number of embodiments, an individual's genetic data, including variant data, and historical health record data are obtained (621). The genetic data, in accordance with many embodiments, is any DNA sequence data of individual that is inclusive of the set of genes identified to distinguish the particular trait to be analyzed. In some embodiments, genetic data is an individual's entire genome, a partial genome (e.g., exome), or other data that include at least a portion of an individual's sequence and variant data. In some embodiments, genetic data is only sequencing data on a minimal set of genes that distinguish the trait to be analyzed (e.g., capture sequencing). In some embodiments, sequence data are obtained by a biopsy of an individual, in which genetic material is extracted and sequenced in accordance with various protocols known in the art.

The historical health data, in accordance with many embodiments, is any health record data to be used in a classification model (i.e., health record data used to train the classification model). In some embodiments, health record data includes include (but is not limited to) sex, age, weight, body fat, smoking history, drinking history, substance abuse history, blood pressure, heart rate, glucose levels, insulin levels, cholesterol levels, triglycerides, etc. In a number of embodiments, the data to be collected can be varied and tailored to the needs of the classification model that has been developed and trained.

A trained classification model capable of classification of trait status is also obtained (623). In several embodiments, a trained classification model classifies an individual based in part on the variant pattern with a set of genes that distinguishes a particular trait. In several embodiments, a trained classification model is capable of agnostically classifying trait status. In some embodiments, a trained classification model is trained by combining the training methods as shown and described in FIGS. 4 and 5, however, in accordance with more embodiments, any classification model capable of classifying an individual on trait status based on genetic sequence and health record data may be used. It should be understood that genetic and health record features can be used in a singular model, combining genetic and health record data of cohorts. In a number of embodiments, an individual's genetic sequence and health record data are entered (625) into a classification model, wherein subsequently the individual's trait status is classified (627). In some embodiments, the individual's trait status is classified based upon a variant pattern of a set of genes that distinguishes the trait. In some embodiments, a trait-positive diagnosis is based upon an aggregate variant burden score above a threshold as determined by scoring the variant pattern of a set of genes that distinguishes the trait. In some embodiments, a variant burden score is based upon the deleteriousness and frequency of variants within the set of genes that distinguishes the trait. In some embodiments, trait status is based upon by an accumulated trait-risk coefficient for each measurement in the health record data. In some embodiments, the individual's trait status is agnostically classified. In some embodiments, the Scikit-learn process is used to implement the classification.

In several embodiments, the trait classification of the individual is reported and/or stored (629). In numerous embodiments, the classification can be used in a number of downstream applications, which may include (but is not limited to) diagnosis of individuals and determination of medical intervention.

While a specific example of a process for classifying individuals is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Systems of Rare Variant Extrapolations and Classifications

Figure 7:
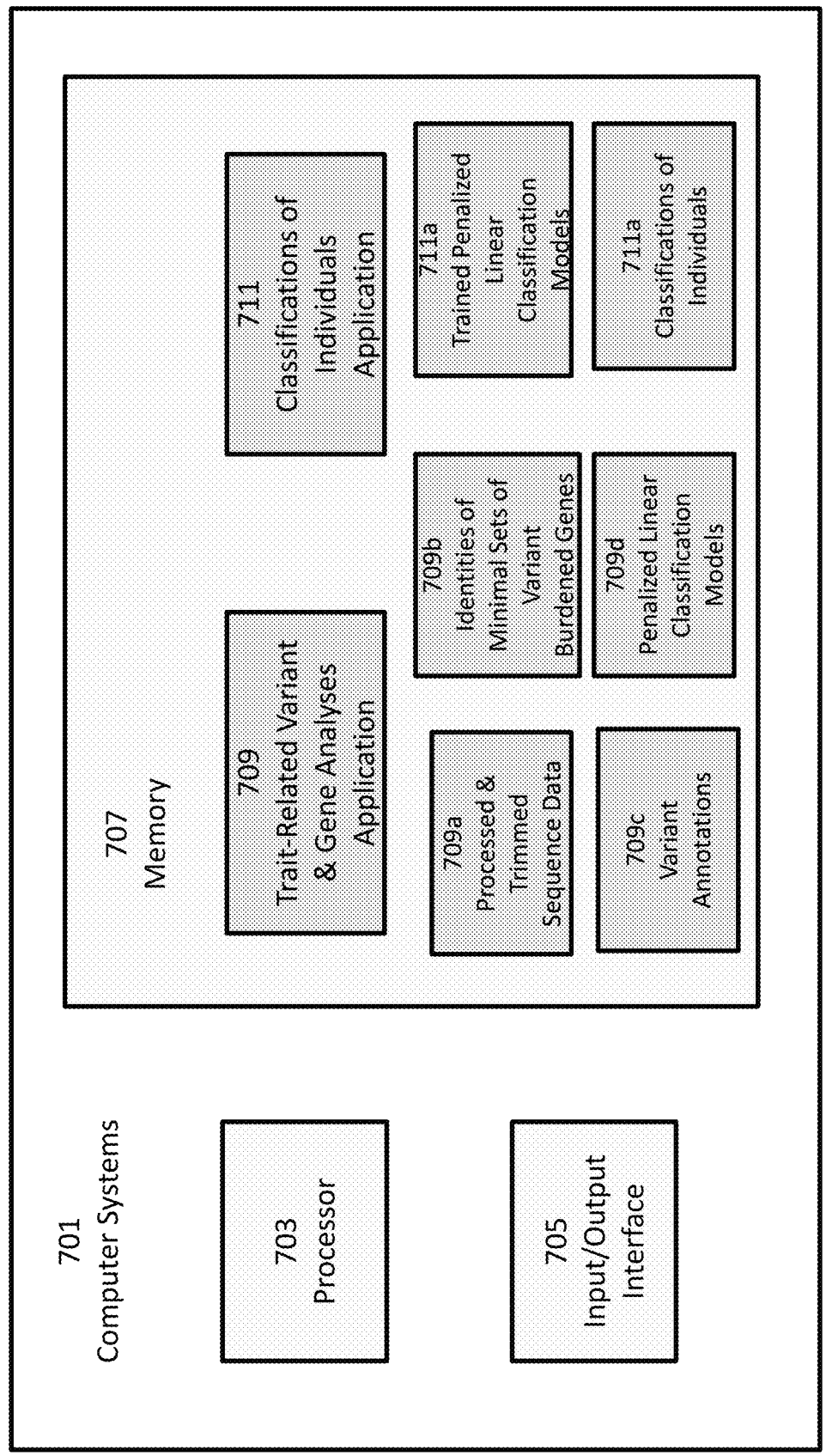
FIG. 7 provides a diagram of computer systems configured to identify minimal sets of trait-related variant burden genes and classification of individuals in accordance with various embodiments of the invention.

Turning now to FIG. 7, computer systems (701) may be implemented on computing devices in accordance with some embodiments of the invention. The computer systems (701) may include personal computers, a laptop computers, other computing devices, or any combination of devices and computers with sufficient processing power for the processes described herein. The computer systems (701) include a processor (703), which may refer to one or more devices within the computing devices that can be configured to perform computations via machine readable instructions stored within a memory (707) of the computer systems (701). The processor may include one or more microprocessors (CPUs), one or more graphics processing units (GPUs), and/or one or more digital signal processors (DSPs). According to other embodiments of the invention, the computer system may be implemented on multiple computers.

In a number of embodiments of the invention, the memory (707) may contain a trait-related variant and gene analyses application (709) and classification of an individual application (711) that performs all or a portion of various methods according to different embodiments of the invention described throughout the present application. As an example, processor (703) may perform a trait-related variant gene analyses methods similar to any of the processes described above with reference to FIGS. 2 and 4 and a classification of an individual process similar to any of the processes described above with reference to FIGS. 6A, 6B and 6C, during which memory (707) may be used to store various intermediate processing data such as processed and trimmed sequence data (709*a*), variant annotations (709*b*), identities of minimal sets of variant burdened genes (709*c*), penalized classification models (709*d*), trained penalized linear classification models (711*a*), and classifications of individuals (711*b*).

In some embodiments of the invention, computer systems (701) may include an input/output interface (705) that can be utilized to communicate with a variety of devices, including but not limited to other computing systems, a projector, and/or other display devices. As can be readily appreciated, a variety of software architectures can be utilized to implement a computer system as appropriate to the requirements of specific applications in accordance with various embodiments of the invention.

Although computer systems and processes for variant analyses and performing actions based thereon are described above with respect to FIG. 7, any of a variety of devices and processes for data associated with variant analyses as appropriate to the requirements of a specific application can be utilized in accordance with many embodiments of the invention.

Diagnostics and Treatments of Complex Diseases

Various embodiments are directed to development of treatments related to classification of individuals based on their genetic and/or health record data. As described herein, an individual may be classified as having a particular trait status in relation to a disease. In some embodiments, an individual is classified as having a disorder or having a high propensity for a disorder. Based on their trait classification, individuals can be treated with various medications, dietary supplements, dietary alterations, and physical exercise regimens.

Diagnostic Methods

A number of embodiments are directed towards diagnosing individuals using trained classification models. In some embodiments, a trained classification model has been trained using genetic data of trait-positive cohorts (e.g., having a medical disorder). In some embodiments, a trained classification model has been trained using health record data of trait-positive cohorts. And in some embodiments, a trained classification model has been trained using genetic and health record data of trait-positive cohorts.

In a number of embodiments, diagnostics can be performed as follows:
a) obtain genetic and/or health record data of the individual to be diagnosed
b) obtain a trained classification model that classifies disorder status
c) enter genetic and/or health record data of the individual into the trained classification model
d) diagnose the individual based on the classification result.

Diagnoses, in accordance with various embodiments, can be performed as portrayed and described in any one of FIG. 6A, 6B, or 6C.

Many embodiments of diagnostics improve on traditional diagnostic methods, especially in cases of complex disorders. Because the genetic contribution to complex disorders is often obscured by the fact several genes and/or variants are combined to yield the disorder, traditional genetic tests of examining a single gene, variant, and/or locus have been unavailable. As described herein, however, in some embodiments, a diagnosis is performed for a complex disease utilizing variant and health data aggregating techniques, such as those described in FIGS. 6A, 6B, and 6C. In some embodiments, diagnoses are performed for disorders in which no single variant is diagnostic. In some embodiments, diagnoses are performed for disorders having a multigene contribution. Various embodiments are directed to diagnoses of complex (i.e., multifactorial) disorders, including (but not limited to) abdominal aortic aneurysm, Alzheimer disease, arthritis, asthma, bipolar disorder, autism spectrum disorder, cancer, cleft lip and/or palate, coronary artery disease, Crohn's disease, dementia, depression, diabetes (type II), heart disease, heart failure, high cholesterol, hypertension, hypothyroidism, irritable bowel syndrome, obesity, osteoporosis, Parkinson disease, rhinitis (allergic and nonallergic), psoriasis, multiple sclerosis, schizophrenia, sleep apnea, spina bifida, and stroke.

Diagnostic Kits

Embodiments are directed towards gene sequencing kits to be utilized within various methods as described herein. As described, various methods can classify an individual for a complex trait by examining the variant pattern with a set of genes. Accordingly, a number of embodiments are directed towards gene sequencing kits that cover a set of genes identified to distinguish a particular trait. In some instances, the set of genes identified are identified by a classification model, such as one described in FIG. 4.

A number of targeted gene sequencing protocols are known in the art, including (but not limited to) partial exome sequencing, primer-directed sequencing, and capture sequencing. Generally, targeted sequencing involves selection step either by hybridization and/or amplification of the target sequences prior to sequencing. Therefore, embodiments are directed to kits that target genes that are identified to distinguish a particular trait.

The number of genes to include in a gene sequencing kit can vary, depending on the genes identified for a particular trait and the classification model to be used. In some embodiments, the genes to be sequenced are identified by a classification model, such as the classification model described in FIG. 4. In various embodiments, the number of genes in a kit are approximately, 10, 20, 30, 40, 50, 60, 70, 80, 90, 100, 150, or 200 genes. In one example, as described in the exemplary embodiments, a minimal set of 60 genes were identified to distinguish abdominal aortic aneurysm and thus embodiments are directed to sequencing kits of the 60 genes identified. It should be understood that precise number and list of genes can vary, as the classification model can be updated with new data or recreated with a different data set.

Medications and Supplements

Several embodiments are directed to the use of medications and/or dietary supplements to treat an individual based on their trait disorder classification. In some embodiments, medications and/or dietary supplements are administered in a therapeutically effective amount as part of a course of treatment. As used in this context, to "treat" means to ameliorate at least one symptom of the disorder to be treated or to provide a beneficial physiological effect.

A therapeutically effective amount can be an amount sufficient to prevent reduce, ameliorate or eliminate symptoms of diseases or pathological conditions susceptible to such treatment, such as, for example, diabetes, heart disease, or other diseases that are complex. In some embodiments, a therapeutically effective amount is an amount sufficient to reduce the symptoms of a complex disorder.

Dosage, toxicity and therapeutic efficacy of the compounds can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to other tissue and organs and, thereby, reduce side effects.

Data obtained from cell culture assays or animal studies can be used in formulating a range of dosage for use in humans. If the pharmaceutical is provided systemically, the dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration or within the local environment to be treated in a range that includes the $IC_{50}$ (i.e., the concentration of the test compound that achieves a half-maximal inhibition of neoplastic growth) as determined in cell culture. Such information can be used to more accurately determine useful doses in humans. Levels in plasma may be measured, for example, by liquid chromatography coupled to mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result.

A number of medications and treatments are known for several complex disorders. Accordingly, embodiments are directed toward treating an individual with a known medication and/or treatment when diagnosed with a complex disorder as described herein. Various embodiments are directed to treatments of complex (i.e., multifactorial) disorders, including (but not limited to) abdominal aortic aneurysm, Alzheimer disease, arthritis, asthma, autism spectrum disorder, bipolar disorder, cancer, cleft lip and/or palate, coronary artery disease, Crohn's disease, dementia, depression, diabetes (type II), heart disease, heart failure, high cholesterol, hypertension, hypothyroidism, irritable bowel syndrome, obesity, osteoporosis, Parkinson disease, rhinitis (allergic and nonallergic), psoriasis, multiple sclerosis, schizophrenia, sleep apnea, spina bifida, and stroke.

Once diagnosed for having a risk of abdominal aortic aneurysm, regular screening and medical monitoring, especially imaging (e.g., ultrasound, CT, or MRI), should be performed to keep watch for any potential any formation or worsening of an aneurysm. Keeping blood pressure and cholesterol in check is important to prevent formation and/or worsening of aneurysm. Accordingly, reducing stress and/or taking medications to reduce hypertension (e.g., diuretics, beta blockers, ACE inhibitors, angiotensin II receptor blockers, and calcium channel blockers) and to enhance cholesterol ratios (e.g., statins, bile acid sequestrates, cholesterol absorption inhibitors, PCSK9 inhibitors, and fibrates) are good treatments. Supplements can also be taken, including (but not limited to) co-enzyme Q, red yeast rice extract, niacin, soluble fiber, and omega-3-fatty acids. Individuals at risk for developing AAA should also reduce tobacco products, eat a healthy diet (avoiding saturated fat, trans fat, and salt), and get regular exercise. In some instances, aneurysms will need to be repaired and thus surgery can be performed.

Once diagnosed for having a risk of Alzheimer's disease, neurological and neuropsychological tests can be performed to check mental status. Imaging (e.g., MRI, CT, and PET) can be performed to check for abnormalities in structure or function. A number of supplements may help brain health and may be prophylactic, including (but not limited to) omega-3 fatty acids, curcumin, ginkgo, and vitamin E. Exercise, diet, and social support can help promote good cognitive health. Medications for Alzheimer's include (but are not limited to) cholinesterase inhibitors and memantine.

Once diagnosed for having a risk of arthritis, laboratory tests on various bodily fluids can be performed to determine the type of arthritis. Imaging (e.g., X-rays, CT, MRI, and ultrasound) can be utilize to detect problems in various joints. Physical therapy may help relieve some complications associated with arthritis. Medications for arthritis include (but are not limited to) analgesics, nonsteroidal anti-inflammatory drugs (NSAIDs), counterirritants, disease-modifying antirheumatic drugs, biologic response modifiers, and corticosteroids. Heat pads, ice packs, acupuncture, glucosamine, yoga, and massage are examples of various home/alternative remedies available.

Once diagnosed for having a risk of asthma, tests can be performed to determine lung function. A chest X-ray of CT scan can be performed to determine any structural abnormalities. Medications for asthma include (but are not limited to) inhaled corticosteroids, leukotriene modifiers, long-acting beta agonists, short-acting beta agonists, theophylline, and ipratropium. In some instances, allergy medications may help asthma and thus allergy shots and/or omalizumab can be administered. Regular exercise and maintaining a healthy wait may help reduce asthma symptoms.

Once diagnosed for having a risk of autism spectrum disorder, medical monitoring (e.g., regular check-ups) can be performed to look for signs of developmental delays. Various treatments include behavioral, communication, and educational therapies, each of which strive to improve a diagnosed individual's social and cognitive skills.

Once diagnosed for having a risk of bipolar disorder, a psychiatric assessment can be performed to determine the feelings and behavior patterns. Psychotherapies and medications are available to treat bipolar disorder. Psychotherapies include (but not limited to) interpersonal and social rhythm therapy (IPSRT), cognitive behavioral therapy (CBT), and psychoeducation. Medications include (but not limited to) mood stabilizers, antipsychotics, antidepressants, and anti-anxiety medications. Some lifestyle changes can help manage some cycles of behavior that may worsen the condition, including (but not limited to) limiting drugs and alcohol, forming healthy relationships with positive influence, and getting regular physical activity.

Once diagnosed for having a risk of cancer, physical exams, laboratory tests and imaging (e.g., CT, MRI, PET) can be performed to determine if cancerous tissue is present. A biopsy can be extracted to confirm a growth is cancerous. Various treatments can be performed, including (but not limited to) adjuvant treatment, palliative treatment, surgery, chemotherapy, radiation therapy, immunotherapy, hormone therapy, and targeted drug therapy. Exercise and a healthy diet can help an individual mitigate cancer onset and progression.

Once diagnosed for having a risk of cleft lip or palate, ultrasound can be performed in utero to determine whether a fetus is developing a cleft lip or palate. Typical treatment is surgery to repair the cleft tissue.

Once diagnosed for having a risk of coronary artery disease, an electrocardiogram and/or echogram can be performed to determine a heart's performance. A stress test can be performed to determine the ability of the heart to respond to physical activity. A heart scan can determine whether calcium deposits. Patients having risk of coronary artery disease would benefit greatly from a few lifestyle changes, including (but not limited to) reduce tobacco use, eat healthy foods, exercise regularly, lose excess weight, and reduce stress. Various medications can also be administered, including (but not limited to) cholesterol-modifying medications, aspirin, beta clockers, calcium channel blockers, ranolazine, nitroglycerin, ACE inhibitors and angiotensin II receptor blockers. Angioplasty and coronary artery bypass can be performed when more aggressive treatment is necessary.

Once diagnosed for having a risk of Crohn's disease, a combination of tests and procedures can be performed to confirm the diagnosis, including (but not limited to) blood tests and various visual procedures such as a colonoscopy, CT scan, MRI, capsule endoscopy and balloon-assisted enteroscopy. Treatments for Crohn's disease includes corticosteroids, oral 5-aminosliclates, azathioprine, mercaptopurine, infliximab, adalimumab, certolizumab pegol, methotrexate, natalizumab and vedlizumab. A special diet may help suppress some inflammation of the bowel.

Once diagnosed for having a risk of dementia, further analysis of mental function can be performed to gauge memory, language skills, ability to focus, ability to reason, and visual perception. These analyses can be performed utilizing cognitive and neuropsychological tests. Brain scan (e.g., CT, MRI, and PET) and laboratory tests can be performed to determine if physiological complications exist. Medications for dementia include cholinesterase inhibitors and memantine.

Once diagnosed for having a risk of diabetes, a number of tests can be performed to determine an individual's glucose levels and regulation, including (but not limited to) glycated hemoglobin A1C test, fasting blood sugar levels, and oral glucose tolerance test. Routine visits may be performed to get a long-term regulatory look at glucose regulation. In addition, a glucose monitor can be utilized to continuously monitor glucose levels. Diabetes can be managed by various options, including (but not limited to) healthy eating, regular exercise, medication, and insulin therapy. Medications for diabetes include (but are not limited to) metformin, sulfonylureas, meglitinides, thiazolidinediones, DPP-4 inhibitors, SGLT inhibitors, and insulin.

Once diagnosed for having a risk of heart disease, various tests can be performed to determine heart function, including (but not limited to) electrocardiogram, Holter monitoring, echocardiogram, stress test, and cardiac catheterization. Lifestyle changes can dramatically improve heart disease, including (but not limited to) limiting tobacco products, controlling blood pressure, keeping cholesterol in check, keeping blood glucose levels in a good range, physical activities, eating healthy, maintaining a healthy weight, managing stress, and coping with depression. A number of medications can be provided, as dependent on the type heart of disease.

Once diagnosed for having a risk of heart failure, various tests can be performed to confirm the diagnosis, including (but not limited to) physical exams, blood tests, chest X-rays, electrocardiogram, stress test, imaging (e.g., CT and MRI), coronary angiogram, and myocardial biopsy. Medications for heart failure include (but are not limited to) ACE inhibitors, angiotensin II receptor blockers, beta blockers, diuretics, aldosterone antagonists, inotropes, and digoxin. Surgical procedures may be necessary, and include (but are not limited to) coronary bypass surgery and heart valve repair/replacement.

Once diagnosed for having a risk of high cholesterol, blood tests can be performed to measure total cholesterol, LDL cholesterol, HDL cholesterol, and triglycerides. Medications to manage cholesterol levels include (but are not limited to) statins, bile-acid-binding resins, cholesterol absorption inhibitors, and fibrates. Supplements can also be taken, including (but not limited to) co-enzyme Q, red yeast rice extract, niacin, soluble fiber, and omega-3-fatty acids. Individuals at risk for high cholesterol should also reduce tobacco products, eat a healthy diet (avoiding saturated fat, trans fat, and salt), and get regular exercise.

Once diagnosed for having a risk of hypertension, blood pressure levels can be monitored periodically (even at home). Elevated blood pressure and hypertension benefit from lifestyle changes including, eating healthy, reducing sodium intake, regular physical activity, maintaining a proper rate, and limiting alcohol intake. Medications for hypertension include (but are not limited to) ACE inhibitors, angiotensin II receptor blockers, calcium channel blockers, alpha blockers, beta blockers, aldosterone antagonists, renin inhibitors, vasodilators, and central-acting agents.

Once diagnosed for having a risk of hypothyroidism, blood tests can be performed to measure the level of TSH and thyroid hormone thyroxine. Medications for hypothyroidism includes (but is not limited to) synthetic thyroid hormone levothyroxine, which may be taken with supplements such as iron, aluminum hydroxide, and calcium to help absorption.

Once diagnosed for having a risk of irritable bowel syndrome (IBS), physical exams can be performed to confirm IBS including determining type of IBS. These exams include (but are not limited to) flexible sigmoidoscopy, colonoscopy, X-ray, and CT scan. A proper diet can be utilized to manage symptoms, including (but not limited to) high fiber fluids, plenty of fluids, and avoiding the following: high-gas foods, gluten, and FODMAPs. Medications for IBS include (but are not limited to) alosetron, eluxadoline, rifaximin, lubiprostone, linaclotide, fiber supplements, laxatives, anti-diarrheal medications, anticholinergic medications, antidepressants, and pain medications.

Once diagnosed for having a risk of obesity, a physiological test to determine body-mass index (BMI) may be performed. Obesity can be managed by various lifestyle remedies including (but not limited to) healthy diet, physical activity, and limiting tobacco products. If obesity is severe, various surgeries can be performed, including (but not limited to) gastric bypass surgery, laparoscopic adjustable gastric banding, biliopancreatic diversion with duodenal switch, and gastric sleeve.

Once diagnosed for having a risk of osteoporosis, bone density can be measured and routinely monitored using X-rays and other devices, as known in the art. Medications for osteoporosis include (but are not limited to) bisphosphonates, estrogen (and estrogen mimics), denosumab, and teriparatide. To reduce the risk of osteoporosis development, individuals can make various lifestyle changes, including (but not limited to) limiting tobacco use, limiting alcohol intake, and taking measures to prevent falls.

Once diagnosed for having a risk of Parkinson's disease, a single-photon emission computerized tomography (SPECT) scan can image dopamine transporter activity in the brain, which can be monitored over time. Medications for Parkinson's includes (but are not limited to) carbidopa-levodopa, dopamine agonists, MAO B inhibitors, COMT inhibitors, anticholinergics and amantadine.

Once diagnosed for having a risk of rhinitis, various tests can be performed to determine if the rhinitis is due to allergies, including (but not limited to) skin tests looking for allergic reaction, blood tests to measure responses to allergies (e.g., IgE levels). Medications for rhinitis include (but are not limited to) saline nasal sprays, corticosteroid nasal sprays, antihistamines, anticholinergic nasal sprays, and decongestants.

Once diagnosed for having a risk of psoriasis, routine physical exams of the skin, scalp and nails can be performed to look for signs of inflammation. A number of topical treatments can be performed for psoriasis, including (but not limited to) topical corticosteroid, vitamin D analogues, anthralin, topical retinoids, calcineurin inhibitors, salicylic acid, coal tar, and moisturizers. A number of phototherapies can also be performed, including (but not limited to) exposure to sunlight, UVB phototherapy, Goeckerman therapy, excimer laser, and psoralen plus ultraviolet A therapy. Medications for psoriasis include (but are not limited to) retinoids, methotrexate, cyclosporine, and biologics that reduce immune-mediated inflammation (e.g., entanercept, infliximab, adalimumab).

Once diagnosed for having a risk of multiple sclerosis (MS), various tests can be performed overtime to monitor symptoms of MS, including (but not limited to) blood tests, lumbar puncture, MRI and evoked potential tests. A number treatments can help treat acute MS symptoms and to mitigate MS progression, including (but not limited to) corticosteroids, plasma exchange, ocrelixumab, beta interferons, glatiramer acetate, dimethyl fumarate, fingolimod, teriflunomide, natalizumab, alemtuzumab, and mitoxantrone. Physical therapy and muscle relaxants also help mitigate (or prevent) MS symptoms.

Once diagnosed for having a risk of schizophrenia, a physical exam and/or psychiatric evaluation may be performed to determine if symptoms of schizophrenia are apparent. Various antipsychotics may be administered, including (but not limited to) aripiprazole, asenapine, brexpiprazole, cariprazine, clozapine, iloperidone, lurasidone, olanzapine, paliperidone, quetiapine, risperidone, and ziprasidone. Individual with risk of schizophrenia may also benefit from various psychosocial interventions, normalizing thought patterns, improving communication skills, and improving the ability to participate in daily activities.

Once diagnosed for having a risk of sleep apnea, an evaluation that monitors an individual's sleep may be performed, including (but not limited to) nocturnal polysomnography, measurements of heart rate, blood oxygen levels, airflow, and breathing patterns. Sleep apnea therapy may include the use of a continuous positive airway pressure (CPAP) device. A number of lifestyle changes have also been shown to mitigate complications associated with sleep apnea, including (but not limited to) losing excess weight, physical activity, mitigating alcohol consumption, and sleeping on side or abdomen.

Once diagnosed for having a risk of spina bifida, prenatal screening tests can be performed and routinely monitored determine if a fetus is developing spina bifida. Blood tests that can be performed include (but are not limited to) maternal serum alpha-fetoprotein test and measurement AFP levels. Routine ultrasound can be performed to screen for spina bifida. Various treatments include (but are not limited to) prenatal surgery to repair the baby's spinal cord and post-birth surgery to put the meninges back in place and close the opening of the vertebrae.

Once diagnosed for having a risk of stroke, routine monitoring can be performed to determine coronary health status, including (but not limited to) blood clotting tests, imaging (e.g., CT and MRI) to look for potential clots, carotid ultrasound, cerebral angiogram, and echocardiogram. Various procedures that can be performed include (but are not limited to) carotid endarterectomy and angioplasty. Patients having risk of stroke would benefit greatly from a few lifestyle changes, including (but not limited to) reduce of tobacco use, eat healthy foods, exercise regularly, lose excess weight, and reduce stress. Various medications can also be administered, including (but not limited to) cholesterol-modifying medications, aspirin, beta clockers, calcium channel blockers, ranolazine, nitroglycerin, ACE inhibitors and angiotensin II receptor blockers.

Exemplary Embodiments

Bioinformatic and biological data support the methods and systems of classification of rare variant data, clinical data and applications thereof. In the ensuing sections, exemplary computational methods and exemplary applications related to rare variant classifications are provided. Exemplary methods and applications can also be found in the publication "Decoding the Genomics of Abdominal Aortic Aneurysm" of J. Li, et al., *Cell* 2018, 174, 1361-1372, the disclosure of which is herein incorporated by reference.

Decoding the Genomics of Abdominal Aortic Aneurysm

Given the fact that many complex diseases have a strong genetic component (Manolio, T. A., et al. *Nature* 2009, 461, 747-753, the disclosure of which is incorporated herein by reference), one long-standing question in the field has been whether a clinical test consisting of a simple genome scan can be developed. Despite obvious feasibility for monogenic diseases, effective approaches have been generally lacking for complex diseases. For example, genome-wide association studies (GWAS) typically yield weak signals and require a large sample size (McCarthy, M. I., et al. *Nat. Rev. Genet.* 2008, 9, 356-369, the disclosure of which is incorporated herein by reference), making them impractical for clinical use. The mission of the Million Veteran Program (MVP) is to bio-bank a large number of disease genomes from military veterans along with associated electronic health records (EHRs), lifestyle surveys, and military exposures (Gaziano, J. M., et al. J. Clin. Epidemiol. 2016, 70, 224-223, the disclosure of which is incorporated herein by reference). This data-driven strategy is expected to re-shape the field's understanding of human diseases at the molecular level, and will ultimately foster the development of integrated frameworks for individualized disease diagnosis and treatment.

In this example, the focus is on decoding the genome of abdominal aortic aneurysm (AAA). AAA is a common, severe, and complex disease that ranks as the tenth leading cause of death in western countries and affects 5-9% of the population aged at 65 years old and above (Thompson, R. W. et al. *Ann. N.Y. Acad. Sci.* 2006, 1085, 59-73; Brangsch, J. et al. *Trends Mol. Med.* 2017, 23, 150-164; the disclosures of which is incorporated herein by reference). The disease is hallmarked by irreversible dilation of the infrarenal aorta to a diameter of ≥30 millimeters (mm), and is accompanied by chronic inflammation, vascular smooth muscle cell apoptosis, extracellular matrix degradation, and luminal thrombosis (Aggarwal, S., et al. *Exp. Clin. Cariol.* 2011, 16, 11-15; Nordon, I. M., et al. *Nat. Rev. Cardiol.* 2011, 8, 92-102; the disclosures of which are incorporated herein by reference). AAA is typically asymptotic as it grows, and clinical diagnosis is usually made at the late stage. Rupture of aorta, the most common complication, has a mortality rate of 90% (Pearce, W. H., et al. *Circulation* 2008, 118, 2860-2863, the disclosure of which is incorporated herein by reference).

While there are the many risk factors for AAA development, the genetic component is substantial with an estimated heritability of 70% (Wahlgren, C. M, et al. *J. Vasc. Surg.* 2010, 51, 3-7, the disclosure of which is incorporated herein by reference). This high rate of heritability suggests that there is a strong genetic influence in AAA etiology.

Figure 8:
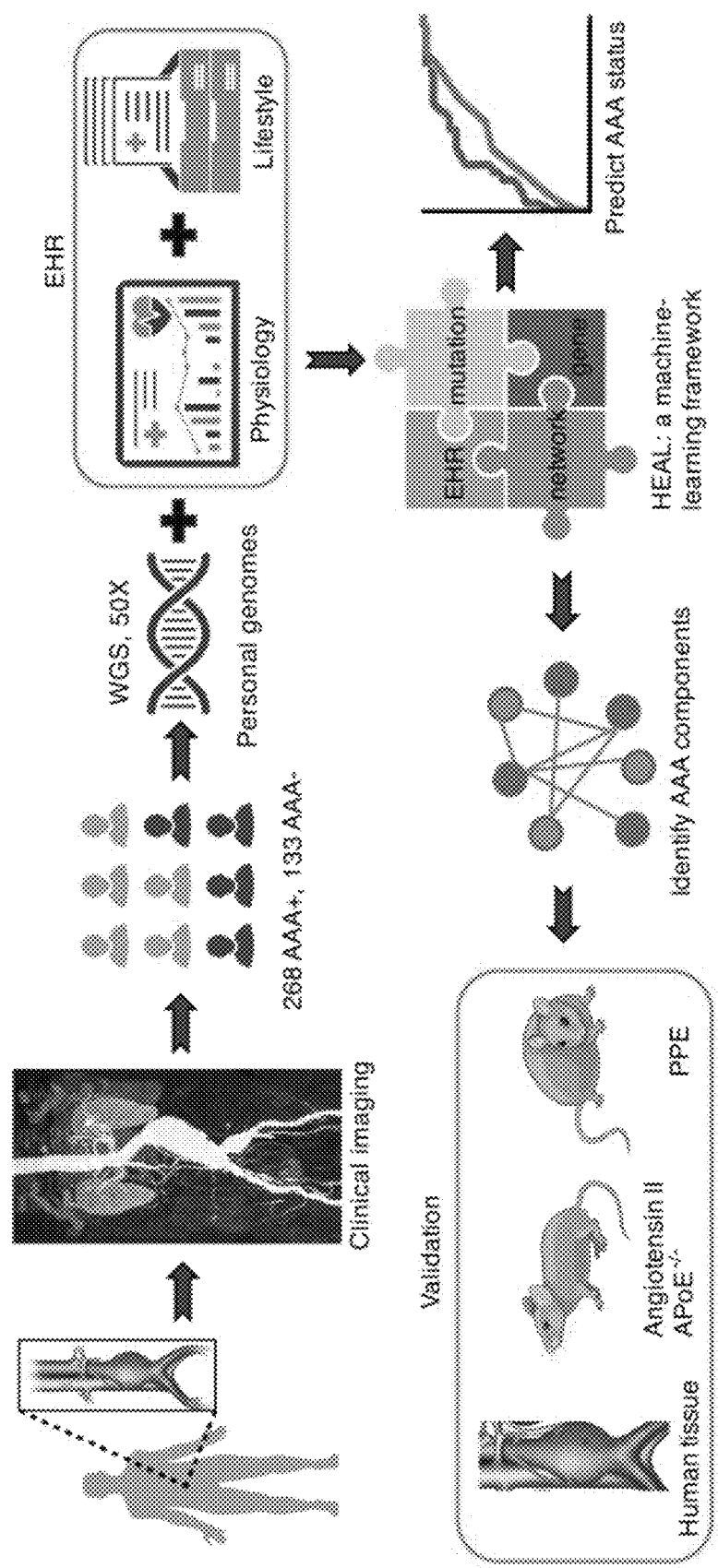
FIG. 8 provides a diagram of a process to predict Abdominal Aortic Aneurism (AAA) utilizing patient cohort genetic and health record data that is incorporated into a computational platform Hierarchical Estimate from Agnostic Learning (HEAL) in accordance with various embodiments of the invention.

AAA exhibits significant mutational heterogeneity (Hinterseher, I., Tromp, G., and Kuivaniemi, H. *Ann. Vasc. Surg.* 2011, 25, 388-412; and Bown, M. J. *Ann. R. Coll. Surg. Engl.* 2014, 96, 405-414; the disclosures of which are incorporated herein by reference), and thus typical GWAS approaches have not yet identified robust and replicable at-risk loci (Bradley, D. T., et al. *Eur. J. Vac. Enovasc. Surg.* 2016, 51, 64-75, the disclosure of which is incorporated herein by reference). Over the past decades, many research groups have extensively studied this disease using human tissues and mouse models; however, the genetic underpinnings of AAA have not been sufficient to guide the early screening in clinical practice. In this example, a genome sequencing pipeline has obtained a comprehensive view of the genetic variant landscape underlying this disease (FIG. 8). An entirely new platform system HEAL (Hierarchical Estimate from Agnostic Learning) was built. HEAL was constructed using machine learning and network analysis techniques, where effects of individual mutations, aggregated mutational burden on genes and ablated biological pathways were hierarchically modeled. It also integrates personal genomes with electronic health record (EHR) data to derive insights into disease etiology, clinical prognosis and potential interventions. Such a data-driven strategy is agnostic by nature, not presuming any existing knowledge nor requiring a large number of samples. With rigorous tests and extensive experimental validation, data is provided that shows that HEAL not only identified disease-associated components of AAA by aggregated learning from population genomes, but also accurately predicted disease status purely from personal genomes (FIG. 8). When combined with electronic health records, the predictive power of HEAL is further boosted, reaching a level similar to or better than many existing clinical screening tests. Overall, this computational platform has significantly improved the understanding of the molecular etiology of AAA, and more importantly, provides a proof-of-principle for developing a general analytical framework for clinical diagnosis of complex disease from personal genomes. The analytical framework presented in this study can be readily extended to studying other heritable complex diseases.

Whole Genome Sequencing for AAA Samples

Figure 9:
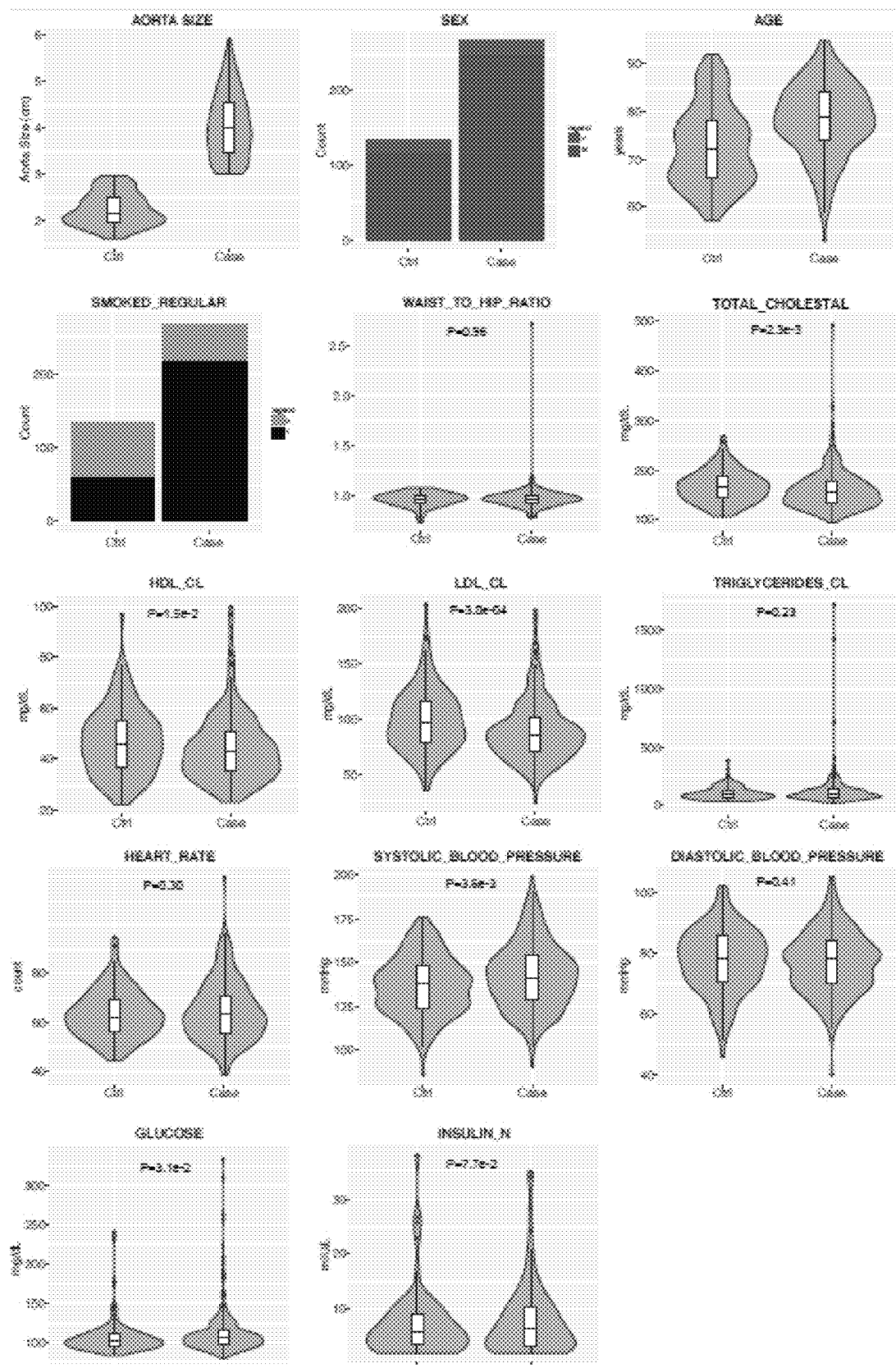
FIG. 9 provides a distribution graph of abdominal aortic diameters, along with other phenotypes, of AAA patients and controls, utilized in accordance with various embodiments of the invention.

Individuals with an abdominal aortic diameter ≥30 mm were considered AAA positive (Moxon, J. V., et al., *Curr. Probl. Cardiol.* 2010, 35, 512-548, the disclosure of which is incorporated herein by reference) and those less than 30 mm were considered negative. Based on these criteria, 313 AAA-positive cases and 161 controls enrolled in the clinical practice at VA Palo Alto Healthcare System, Stanford University and Kaiser Permanente (Myers, J. M., et al. *J. Aging Phys. Act.* 2014, 22, 87-95; and Betz, H. H., et al., *J. Phys. Act. Health* 2015, 12, 376-381; the disclosures of which are incorporated herein by reference). Their AAA status was confirmed by re-visiting their medical history and by re-examining their ultrasound or CT scans for abdominal aortic diameters (See FIG. 9).

The study protocols were approved by the IRB committee at Stanford University. A total of 474 study subjects, all self-reported as Europeans, were recruited and consented in written form through three local hospitals: VAPAHCS, Stanford Hospitals and Clinics, and Kaiser Permanente. Study IDs were given to each subject for de-identification purpose, which were used throughout this research project.

Compared with previous genetic studies, the availability of electronic health records (EHRs) in the examples described herein enabled integration of this information into disease genome analysis as described in detail below. Information contained in EHRs included individuals' various physiological measurements upon their last clinical visit before the initiation of this project as well as smoking history.

Whole-genome sequencing was performed on whole blood samples collected from study participants to an average genome coverage of 50×, resulting in 48 terabytes of aligned reads in compressed BAM format. Specifically, blood was drawn in a 10 ml Vacutainer collection tube (BD, Franklin Lakes, NJ) containing EDTA as the anticoagulant. Buffy coat was collected and transferred immediately into −80° C. freezer. DNA was extracted using Epicentre MasterPure DNA purification kit (cat #MCD85201) and the manufacturer's protocol was followed. DNA concentration was measured by Nano Drop and Qubit fluorimeter and stored under −20° C. till use.

DNA was sent to Illumina, Inc. (San Diego, CA) for whole genome sequencing. Sequencing library preparation followed standard Illumina protocol, with the median insert size of 250 bp. Sequencing was then performed using the 101 base-pair pair-end reversible terminator massively parallel sequencing on the HiSeq 2000 instrument (Bentley, D. R., et al., *Nature* 2008, 456, 53-59, the disclosure of which is incorporated herein by reference).

To process the massive amount of sequencing data and perform rigorous quality control and validation, a columnar database-based analytical pipeline on Google Cloud Platform to perform rigorous quality control and validation (See, Pan, C., et al. 2017, cited supra), flowing the best practiced guideline by Genome Analysis Toolkit (GATK) (McKenna, A., et al., *Genome Res.* 2010, 20, 1297-1303, the disclosure of which is incorporated herein by reference). Briefly, reads were aligned using BWA-MEM v-0.7.10 (Li, H. and Durbin, R., *Bioinformatics* 2009, 25, 1754-1760, the disclosure of which is incorporated herein by reference) to decoy human reference genome hs37d5. PCR duplicates were identified by Picard tools v-1.117. Local realignment around INDELs was performed by GATK v3.3 (referred to as GATK in the following description), in which realignment targets were first generated by RealignerTargetCreator and then the actual local realignment by Indelrealigner. Subsequently, base qualities were recalibrated by the Printreads function in GATK by observing the behavior of those bases reported in dbSNP137. Single nucleotide variation (SNV), indels and reference bases were called by the HaplotypeCaller in GATK. Variant quality score recalibration (VQSR) (DePristo, M. A., et al., *Nat Genet.* 2011, 43, 491-498, the disclosure of which is incorporated herein by reference) was performed by VariantRecalibrator in GATK with the following annotations: quality by depth, mapping quality rank sum, read position rank sum, Fisher strand, coverage, and haplotype score. The training datasets for SNVs were HapMap3 (International HapMap Consortium, *Nature* 2005, 437, 1299-1320, the disclosure of which is incorporated herein by reference), 1000 Genomes Phase I genotypes presented in Omni2.5 array (1000 Genomes Project Consortium, et al., *Nature* 2012 491, 56-65, the disclosure of which is incorporated herein by reference) and dbSNP135 (Sherry S. T., et al., *Nucleic Acids Res.* 2001, 29, 308-311, the disclosure of which is incorporated herein by reference); and the following training dataset for indels was a curated set of indels cataloged by Mills and Devine (Mills R. E., et al., *Genome Res.* 2011, 21, 830-839, the disclosure of which is incorporated herein by reference).

Figure 10:
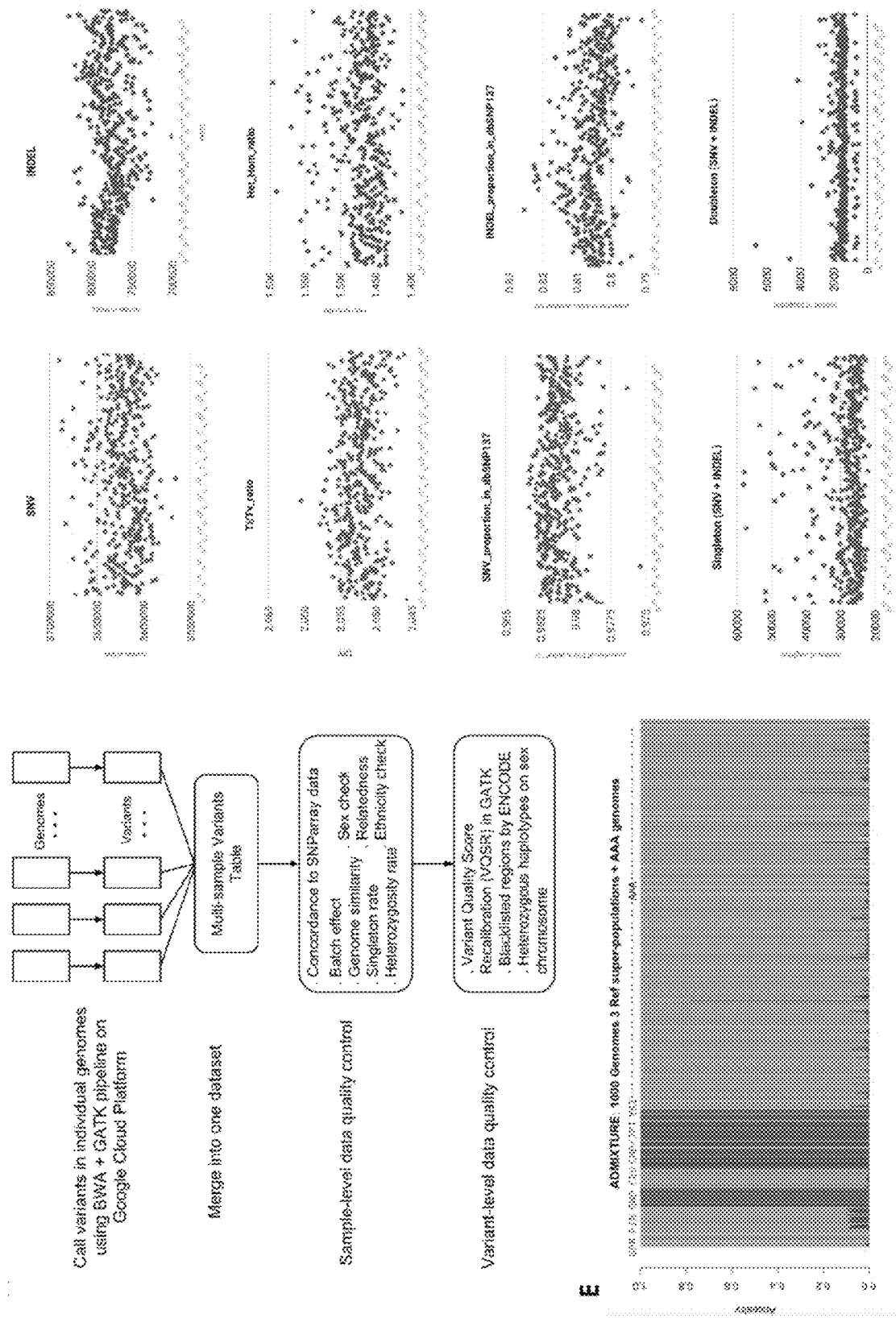
FIG. 10 provides illustrations and charts of variant quality control in accordance with a number of embodiments of the invention.

The resulting genome-wide variant profiles were subsequently subjected to numerous quality control (QC) checks on the Google Cloud Platform, including population admixture analysis, which retained 268 cases and 133 controls for further analysis with an admixture component for Caucasians greater than 90% (FIG. 10). On the sample level, (1) principal component analysis was performed among all samples and found no batch effect among the different DNA library preparations; (2) the genotypes between sequencing data and SNP array data were compared, revealing that all genomes had high concordance; (3) the sex was inferred based on heterozygous counts on chromosome X and 6 samples were tagged that did not have matching self-reported sex; (4) inbreeding coefficient was computed to infer family relationship, and 6 genomes were tagged that resided more than 3 standard deviation from the mean; (5) identify-by-state was computed as a proxy for genome similarity and found no cross-contamination; (6) missing calls for each genome were assessed, revealing that all genomes had minimal missing calls when considering all called positions; (7) the distribution of singleton calls in every genome was assessed and 2 genomes were tagged that resided more than 3 standard deviations from the mean; (8) the distribution of heterozygous calls was assessed in every genome and 5 genomes were tagged that resided more than 3 standard deviation from the mean; and (9) ADMIXTURE analysis was performed referencing 50 European genomes, 50 East Asian genomes, and 50 African genomes from the 1000 Genomes Phase 3 Project and 69 genomes were tagged with <90% European ancestry. Subsequently, all tagged genomes were removed from the downstream analysis. A summary of the sample-level QC was provided in the Table 1.

TABLE 1

Genomes Removed Based on Quality Control Analysis

| Failure Reason | Count (w/overlap) |
|---|---|
| heterozygosity_rate | 5 |
| inbreeding_coefficient | 6 |
| Admixture | 69 |
| private_variants | 2 |
| Gender_ambiguity | 6 |
| Total | n = 73 |

For these retained samples, confident variant calls were identified, including 23,750,363 single nucleotide variations (SNVs). Short insertion and deletions (INDELs) were excluded from this analysis due to their relatively lower confidence compared with SNVs (Zook, J. M., et al. *Nat. Biotechnol.* 2014, 32, 246-251, the disclosure of which is incorporated herein by reference). Variants were tagged and removed from down stream analysis if they (1) existed on blacklisted regions, as gathered by the ENCODE consortium, (2) were heterozygous haplotypes, (i.e., heterozygous call on chromosome X in male genomes, and (3) identified other than "PASS", such as "low quality", "tranche99.0-99.5", by VQSR in GATK.

GWAS was performed first to model AAA dichotomous outcomes with ethnic disparities corrected by population admixture analysis. Standard GWAS analysis was performed based on PLINK (version 1.07) (Purcell, S., et al., *Am. J. Hum. Genet.* 2007 81, 559-575). In particular, the thresholds were set as follows: missing rate per person=0.1; allele frequency 0.01; missing rate per SNV=0.1, and Hardy-Weinberg Equilibrium=0.001. Use of these thresholds revealed 8,412,717 SNVs for further GWAS analysis. The genomic inflation factor (based on median chi-squared) and the mean chi-squared statistic after GWAS were 1.04875 and 1.00209, respectively.

Figure 11:
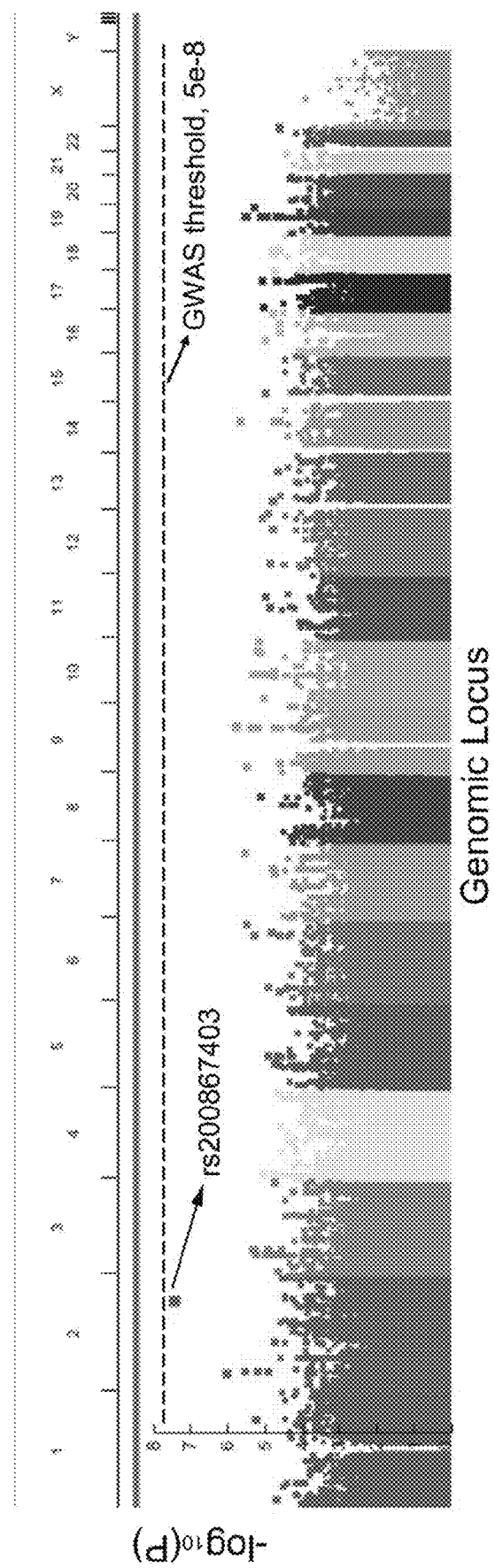
FIG. 11 provides a chart of variant significance p-value of all genomic loci in the AAA cohort, demonstrating no significant variants, generate in accordance with various embodiments of the invention.

No genomic locus reached statistical significance at the threshold at $5e^{-8}$ across the human genome (FIG. 11). A lack of GWAS signal for many complex human diseases is typically attributed to two possible scenarios: (1) locus heterogeneity (Visscher, A., et al. *Am. J. Hum. Genet.* 2012, 90, 7-24, the disclosure of which is incorporated herein by reference), where different subsets of study participants usually carry distinct sets of pathogenic mutations. In this scenario, a large sample size (e.g. at least thousands of samples) is usually required, where at-risk loci could be proportionally enriched in cases relative to controls so as to reach statistical significance. (2) rare variants, which cannot be effectively captured by GWAS that is designed for common variants. To capture effects from rare variants, GWA usually require an exceptionally large sample size (e.g., ~50,000 samples required for a variant with minor allele frequency at 1%) (Lee, S., et al. *Am. J. Hum. Genet.* 2014, 95, 5-23, the disclosure of which is incorporated herein by reference). Several improved association methods aggregated rare variants in a given genomic region (e.g. gene locus) (Lee, S., et al. 2014, cited supra); however, the issue of locus heterogeneity still persists. Therefore, association tests at individual loci are not amenable to diseases that are heterogeneous in nature.

The current example is designed to overcome the challenges often present in GWAS. Rare variants have been thought to have a larger effect than appreciated (See, Cirulli, E. T. and Goldstein, D. B. *Nat. Rev. Genet.* 2010, 11, 415-425; and Auer, P. L. and Lettre, G. *Genome Med.* 2015, 7, 16; the disclosures of which are incorporated herein by reference). Accordingly, rare variants in AAA were examined and incorporated into a constructed a machine-learning model to directly circumvent the challenge of locus heterogeneity that hinder classic models based on statistical tests at each individual locus. For a well-defined clinical phenotype, the seemingly heterogeneous mutations may converge onto a common set of pathways (Li, J., et al. *Cell Syst.* 2015, 1, 361-374; and Li, J., et al. *Mol. Syst. Biol.* 2014, 10, 774; the disclosures of which are incorporated herein by reference). In other words, common sets of mutations (e.g., SNVs) are not prevalent in AAA-positive cohort (i.e., the typical GWAS framework), but rather a common set of gene functions that are more likely to have variants among the AAA-positive cohort (i.e., common ablated pathways). In this "mutational convergence" framework, the task of GWAS for identifying a handful of significant mutations out of millions of SNVs is thus reduced to finding a subset of genes from ~20,000 human genes, whose variant pattern can distinguish the AAA-positive cohort from controls. In practice, by reducing the search space from millions of mutations down to 20,000 genes, the sample size requirement is greatly lowered. Therefore, in this example, a minimal subset of genes across the genome was sought. Furthermore, the combinatorial patterns of rare variants within these genes may be useful to classify individuals on their likelihood of developing AAA.

HEAL: An Agonistic System for Disease Genome Analysis

Figure 12:
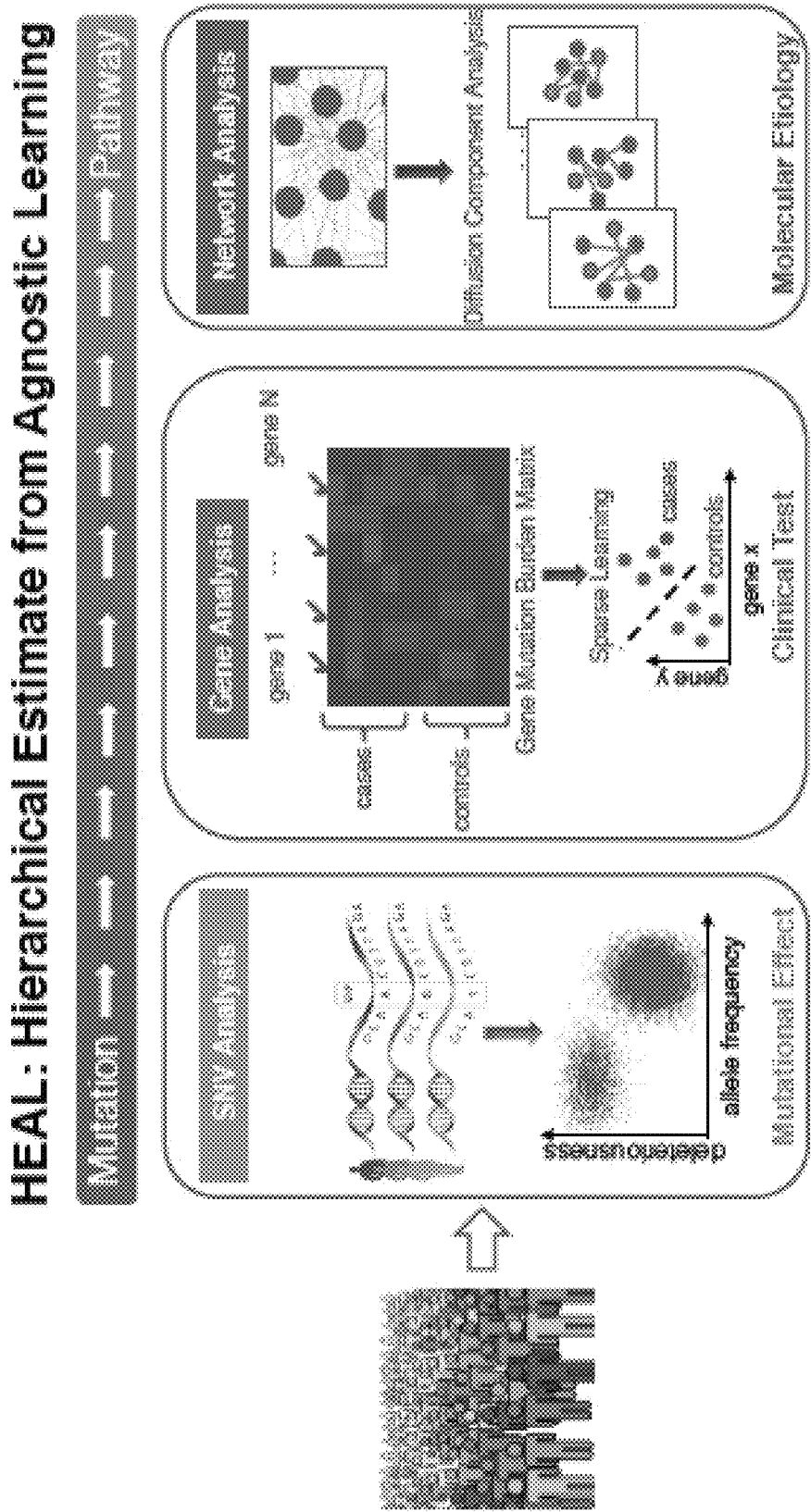
FIG. 12 provides an over view of HEAL in accordance with various embodiments of the invention.

Computational platform HEAL was developed to identify AAA-associated genetic components. The overall design of HEAL is shown in FIG. 12. At the individual SNV level, the platform first examines the potential clinical relevance of each individual mutation by annotating its functional consequences, and population frequency as well as predicted deleteriousness. To overcome mutational heterogeneity, HEAL constructs a machine-learning framework to agnostically identify a subset of genes detected to have an elevated burden for variants in the AAA-positive cohort relative to controls. HEAL utilizes this pattern of variants and genes to predict clinical outcomes of individuals. To gain further insights into disease etiology, HEAL then mapped the identified genes onto biological networks to reveal a complete picture of the molecular pathways in a given disease. As hierarchically modeled, these HEAL frameworks analyze consequences at the mutation level, predict disease outcome at the gene level, and unravel disease etiology at the network level (FIG. 12). In addition, HEAL can be further expanded to incorporate personal EHRs to complement genomic investigations In this example, HEAL was implemented to directly identify genes showing aberrant load of rare variants in AAA-positive cohort (the gene-based model in FIG. 12). Among millions of SNVs identified in this cohort, only 66,047 rare nonsynonymous mutations (missense, nonsense and those affecting splice sites) were considered. These 66,047 mutations were not present in the 1000 Genome Project, as subjects within this project were presumably healthy (Sudmant, P. H., et al. Nature 2015, 526, 75-81, the disclosure of which is incorporated herein by reference). The mutational burden was quantified for each gene, based on the cumulative effects of deleterious nonsynonymous mutations. The mutational burden was computed for each individual in the AAA-positive cohort and controls. HEAL then represented each of the 401 study participants (268 AAA-positive and 133 controls, FIG. 12) with the mutational burden for each human gene in the genome.

To estimate the mutation burden per gene based on the rare SNVs screened, the deleteriousness per nonsynonymous SNV were profiled according to three state-of-the-art annotation tools, including VEST3 (Carter, H., et al. BMC Genomics 2013, 14, 1-16, the disclosure of which is incorporated herein by reference), MetaLR (Dong, C., et al. Hum. Mol. Genet. 2015, 24, 2125-2137, the disclosure of which is incorporated herein by reference) and M-CAP (Jagadeesh, K., et al. Nat. Genet. 2016, 48, 1581-1586, the disclosure of which is incorporated herein by reference). The average prediction scores were then adopted to estimate the deleteriousness of individual SNVs. The cumulative effects of those nonsynonymous SNVs per gene were also considered. In particular, for each gene i (i=1, . . . , 17 443), its mutation burden was calculated as $$g_i = \sum_{j=1}^{n_i} s_{ij}, \quad \text{(Eq. No. 1)}$$

in which $n_i$ is the number of rare SNVs in gene i and $s_{ij}$ is the average deleteriousness score for SNV j. Note that Eq. No. 1 not only considers the deleteriousness of individual SNVs (i.e., $s_{ij}$), but takes the mutation frequency (i.e., $n_i$) into account. The profiling procedure was performed for cases and controls separately, resulting in a feature vector of 17,443 dimensions per sample, i.e., $$x_n = (g_1, \ldots, g_i, \ldots, g_{17443}), \quad \text{(Eq. No. 2)}$$

where $x_n \in \mathfrak{R}^{17443}$ and n denotes the nth sample. After screening for rare SNVs and estimating mutation burdens for individual genes, cohorts can be profiled by pairs $\{x_n, y_n\}$'s (n=1, . . . , 401), in which $x_n$ is given by Eq. (2), and $y_n$ represents the label of "case" or "control", i.e., $y_n=1$ indicates that the nth sample is "case", otherwise it is "control".

Figure 13:
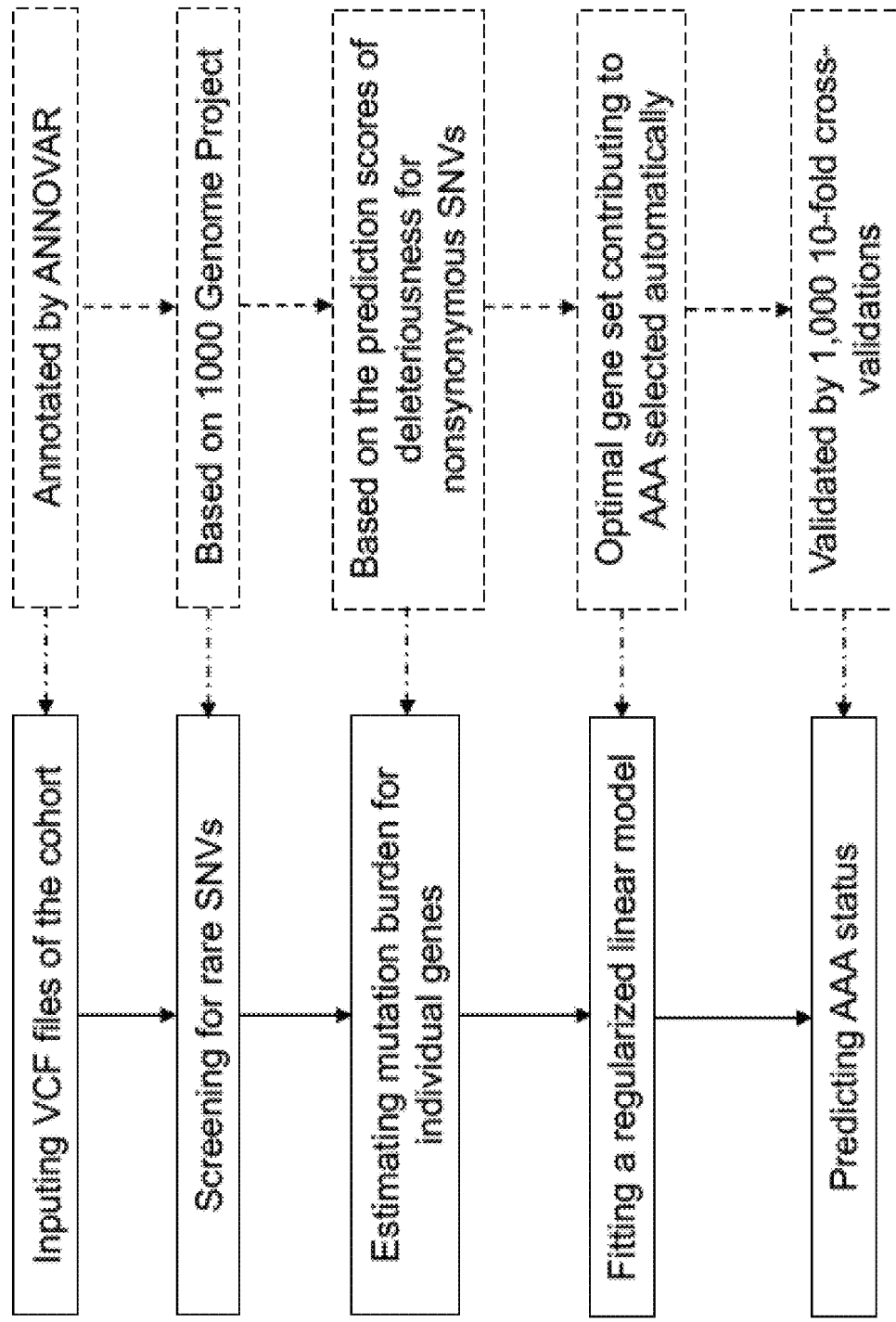
FIG. 13 provides a flowchart of predicting AAA status in accordance with several embodiments of the invention.

A penalized linear classification model was trained to classify the AAA status for each individual, where the penalty term of the classification model served to identify the minimal set of the most distinguishing features (i.e. genes with aberrant mutational burden in cases) for AAA classification (FIG. 13). It is important to note that this sparse learning technique effectively avoids potential overfitting in model construction, which is further evidenced by cross-validation procedures provided below (See, Tibshirani, R. Journal of the Royal Statistical Society: Series B (Statistical Methodology) 2011, 73, 273-282, the disclosure of which is incorporated herein by reference).

To model the additive effect of gene mutation burden on disease risk coefficients $w_i$'s, were introduced to individual genes $g_i$'s, which measures the contribution of mutation burden of corresponding genes to the AAA status. Specifically, given the gene mutation burden profile $x_n$ for the sample n, its probability of being AAA can be modeled as $$\hat{y}_n = P(y_n = 1 \mid x_n) = \sigma(w^T x_n) = \frac{1}{1 + \exp(-w^T x_n)}, \quad \text{(Eq. No. 3)}$$

where $\sigma(\bullet)$ is the sigmoid function. The optimal coefficient w that achieves the maximum consistency between the model probabilities and the observations for the cohort is determined. Indeed, the following logistic regression problem is solved, $$\min_w \mathcal{L}_1(w) = \min_w -\frac{1}{N}\sum_{n=1}^{N} y_n \log \hat{y}_n + (1-y_n)\log(1-\hat{y}_n), \quad \text{(Eq. No. 4)}$$

in which the optimization objective is the average cross-entropy of the sample set.

The main challenge here is that there are a large number (about ten thousands) of features while only a relatively small number (hundreds) of training samples, which would easily lead to the overfitting problem. Accordingly, a parsimonious/sparse structure was adopted in the solution, in which the minimum number of genes/features were targeted to best explain the observations by introducing a penalty term ($L_1$) into Eq. No. 4, i.e., $$\min_w \mathcal{L}_2(w) = \min_w \mathcal{L}_1(w) + \lambda \|w\|_1, \quad \text{(Eq. No. 5)}$$

in which the $L_1$ norm induced a sparse structure, the parameter $\lambda$ tuned the level of sparsity of the solution and was set to 1.5 in this study (See, Bishop, C. M., PATTERN RECOGNITION AND MACHINE LEARNING. Springer-Verlag, New York, 2006, the disclosure of which is incorporated herein by reference). In fact, Problem (5) can be treated as the logistic regression version of LASSO, a popular sparse linear regression model in statistics (Tibshirani, R., J. Royal Statistical Society: Series B (Statistical Methodology) 2011, 73, 273-282, the disclosure of which is incorporated herein by reference). Based on the optimal $\hat{w}$ for Eq. No. 5 and Eq. No. 3, the AAA risk can be predicted or estimated from a personal genome. In this example, the Scikit-learn process was used to implement the method and solve Eq. No. 5 (Pedregosa, F., et al., *J. Mach. Learn. Res.* 2011, 12, 2825-2830, the disclosure of which is incorporated herein by reference).

Figure 14:
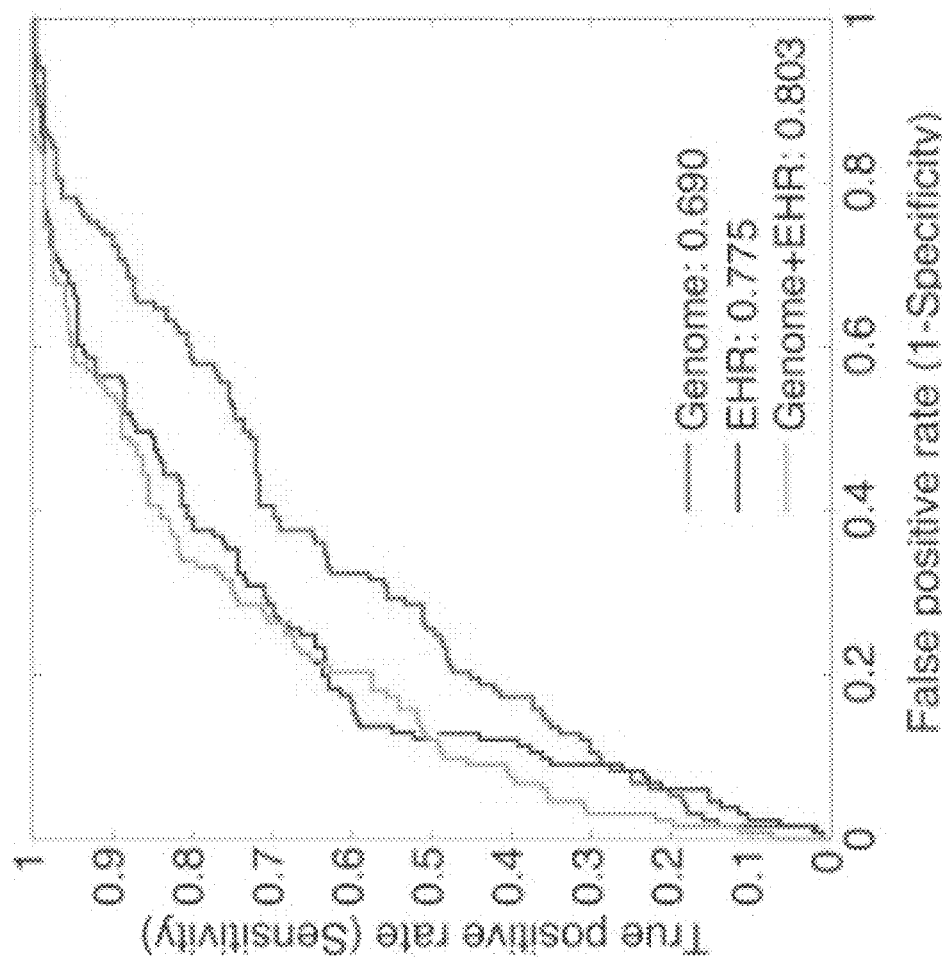
FIG. 14 provides a graph demonstrating the sensitivity and specificity of various trained classification model generated in accordance with a number of embodiments of the invention.
Figure 15:
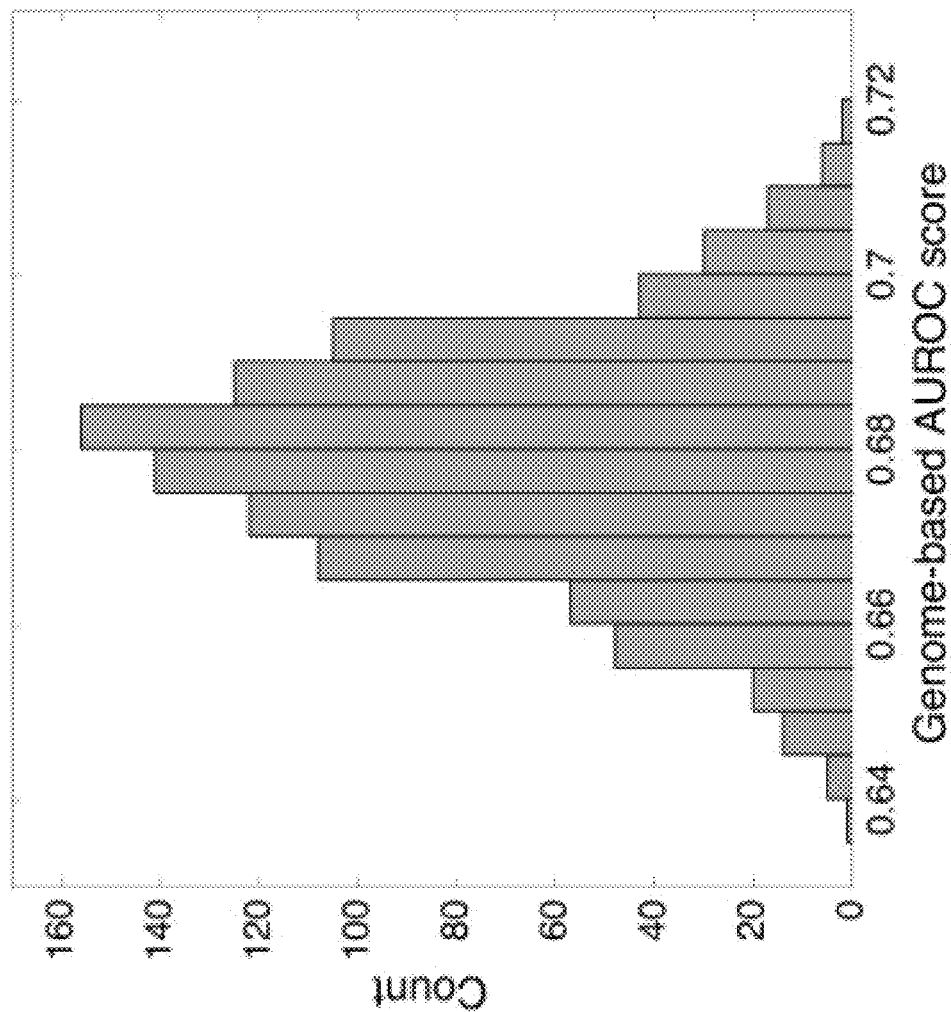
FIG. 15 provides a graph detailing distribution of AUROC scores over 1000 simulations of a genome-based model generated in accordance with various embodiments of the invention.

HEAL revealed a minimal set of 60 genes (Table 2) whose mutational burden best distinguished the AAA-positive cohort from controls. Note that the entire learning process in HEAL was purely agnostic, only guided by the classification accuracy, resulting in a final model that was trained based on the whole cohort, yielding coefficients of individual genes for downstream analysis. Therefore, without injecting any prior knowledge, the revealed genetic components reflect the natural organization of the genetic components underlying AAA. Ten-fold cross-validation was performed 1,000 times to eliminate potential randomness in splitting training and testing samples, where each study participant was blindly tested 1,000 times using different combinations of training samples of the same size (excluding the test subjects when training). Averaging these blind test scores over the 1,000 simulations demonstrated the predictability of AAA status based on the 60 selected genes with an AUROC=0.69 (Area under receiver operating characteristic curve, FIG. 14) and the distribution of AUROCs for the 1,000 iterated cross-validations is shown in FIG. 15.

The study participants' EHRs were also closely examined including their personal lifestyle surveys and lifestyle-associated physiological measurements during their last clinical visit before the initiation of this project. These included sex, age, status as a regular smoker, heart rate, waist-to-hip ratio, insulin level, fasting glucose level, lipid profiles, and several other factors. We constructed a similar machine learning model and found that the EHR information could effectively distinguish AAA patients from non-AAA individuals with an AUROC of 0.775, higher than the genome-based model at AUROC=0.69 (FIG. 2A and Table S4). It is important to note that the higher AUROC from EHRs was expected given known associations with AAA of these physiological and lifestyle elements (Golledge, J., et al., *Health in Men Study* 2007, 116, 2275-2279; Hobbs S. D., et al., *Euro. J. Vasc. Endovasc. Surg.* 2003, 26, 618-622; Stackelberg, O., et al. *J. Am. Heart Assoc.* 2017, 6, e004725; the disclosures of which are each incorporated herein by reference). However, the prediction achieved by the genome-based model was remarkable, especially given the unclear molecular and genetic basis of this complex disease.

Figure 16:
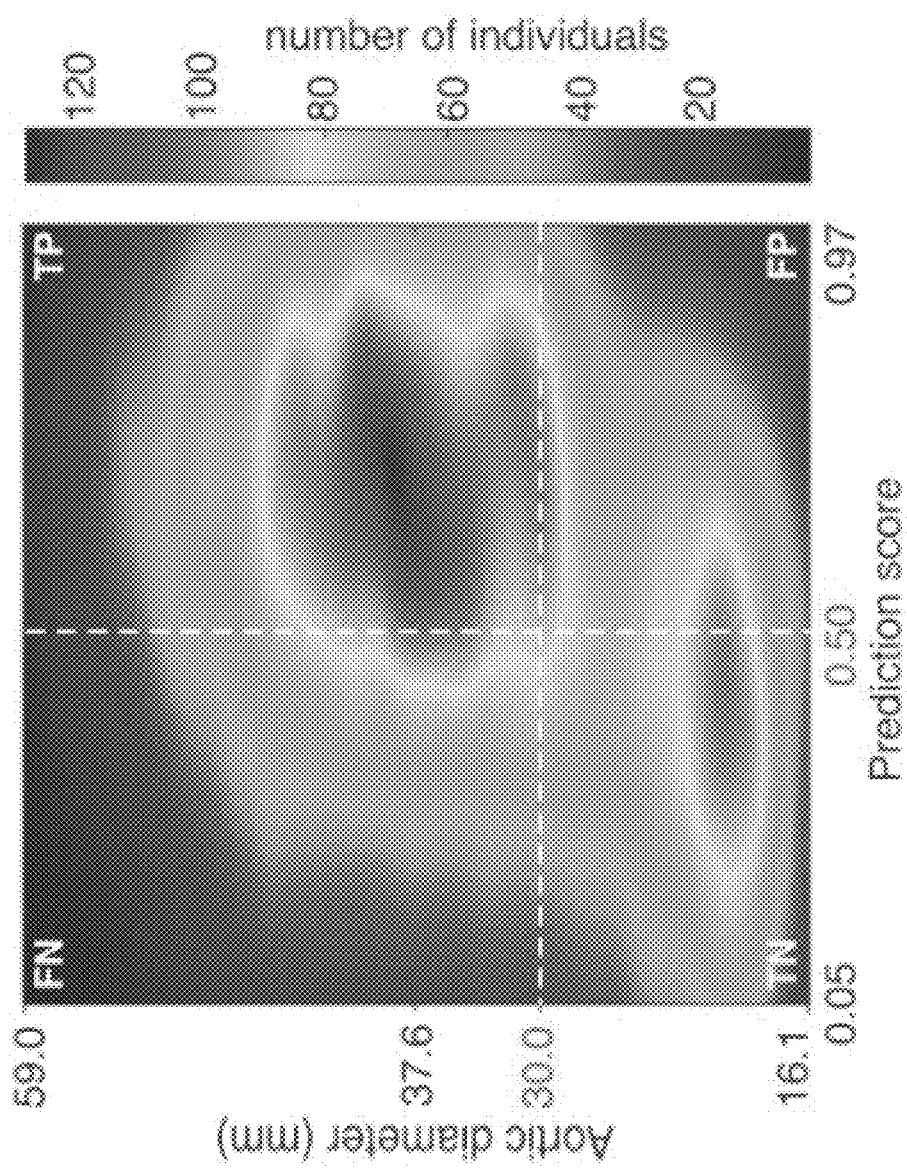
FIG. 16 provides a graph detailing the correlation between aneurism size and predicted score generated in accordance with various embodiments of the invention.

Integrating the EHR information with the genome-wide genetic prediction generated a significant increase in the predictive power to AUROC=0.80 (FIG. 14 and Table S4), demonstrating the complementarity of personal genomes and individual lifestyles in predicting disease outcomes. This performance increase over the EHR-based model was significant, as determined by the 1,000 iterated cross-validations (P<1e-3). The resulting true positives (TP), true negatives (TN), false positives (FP) and false negatives (FN) in the integrated model are illustrated in FIG. 16, where prediction scores for each individual was averaged over the 1,000 cross-validations thresholded at 0.5 for predicted AAA outcomes.

Individual cases were also examined with the integrated model, as exemplified by FIG. 17: a study participant that received a low AAA prediction score (0.16) indeed had a small abdominal aortic diameter (20.1 mm) from ultrasound scan (FIG. 17, top left panel), whereas another individual with a highly dilated abdominal aorta (51.2 mm) from a CT (computed tomography) scan was scored highly by HEAL (prediction score 0.68, FIG. 17, bottom right panel). Notably, two individuals with marginally significant abdominal aortic diameters (31.2 and 30.0 mm in FIG. 17 top right and bottom left panels, respectively, from ultrasound scans) were also scored with marginal AAA probabilities by HEAL (prediction scores of 0.55 and 0.43 in FIG. 17 top right and bottom left panels, respectively), demonstrating that the clinical definition of AAA had indeed been learned by HEAL. Taken together, the genome-based model in HEAL identifies the genome baseline for an individual to develop AAA, and the combined genomics and EHR model in HEAL more accurately predicted the risk, representing a post-probability incorporating genomics, lifestyle and physiological factors and their interactions.

A Clinically Applicable Test for AAA Integrating Personal Genomes with EHR Data

Figure 18:
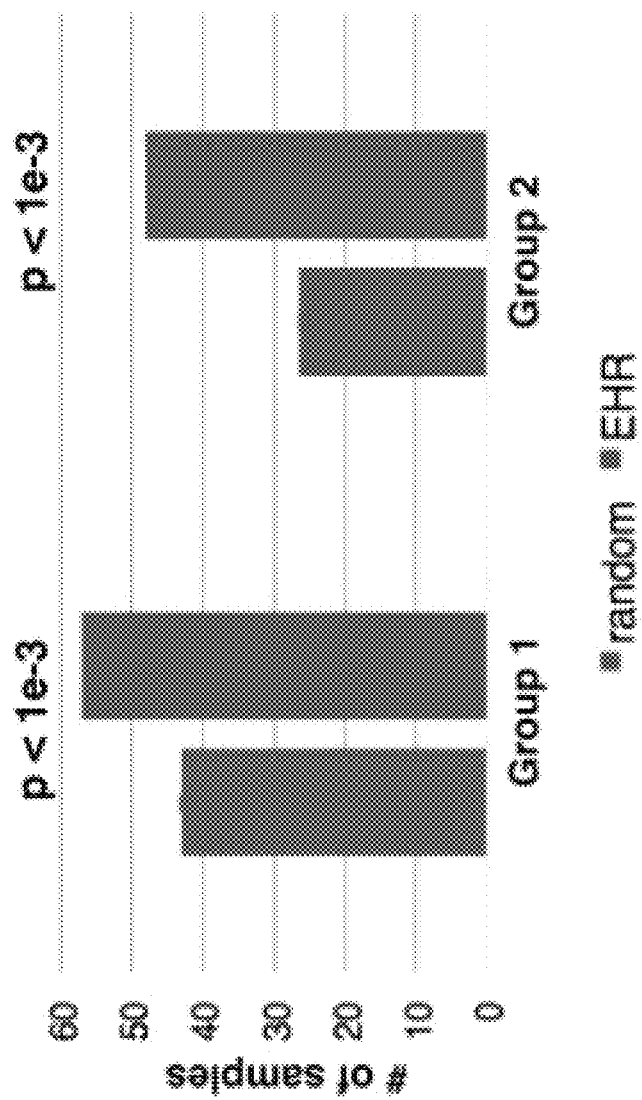
FIG. 18 provides graphs detailing tests for complementarity between genome and health record based models generated in accordance with various embodiments of the invention.

Because both genome- and EHR-based models predicted AAA status, it was explored whether the two models predicted AAA from different mechanisms or from a convergent base (i.e., some EHR phenotypes could be captured by the genome-based model trained for AAA). The same analysis was performed as described above, where each EHR phenotype was regressed (for continuous traits) or classified (for dichotomous traits) using the variants in the genes best predicting AAA, but there was little correlation between the genetic and phenotypic variances ($R^2<0.1$). This observation indicated a direct mapping from personal genomes to AAA status, not through other EHR traits. Because combining EHR and genome information increased prediction accuracy, it was hypothesized that false predictions from personal genomes could be captured by EHR-based predictions. Therefore, false positives and false negatives were identified from personal genome predictions to determine how many of them were correctly captured by the EHR-based predictions. To determine statistical significance, the AAA labels for EHR predictions were randomly permuted 1,000 times and it was observed that the false negatives from genome prediction were indeed enriched for the true positive predictions in the EHR model ($P<1e^{-3}$, Group 1, FIG. 18), and the enrichment was also evident for the genome false positives in the EHR true negatives ($P<1e^{-3}$, Group 2, FIG. 18).

Figure 19A:
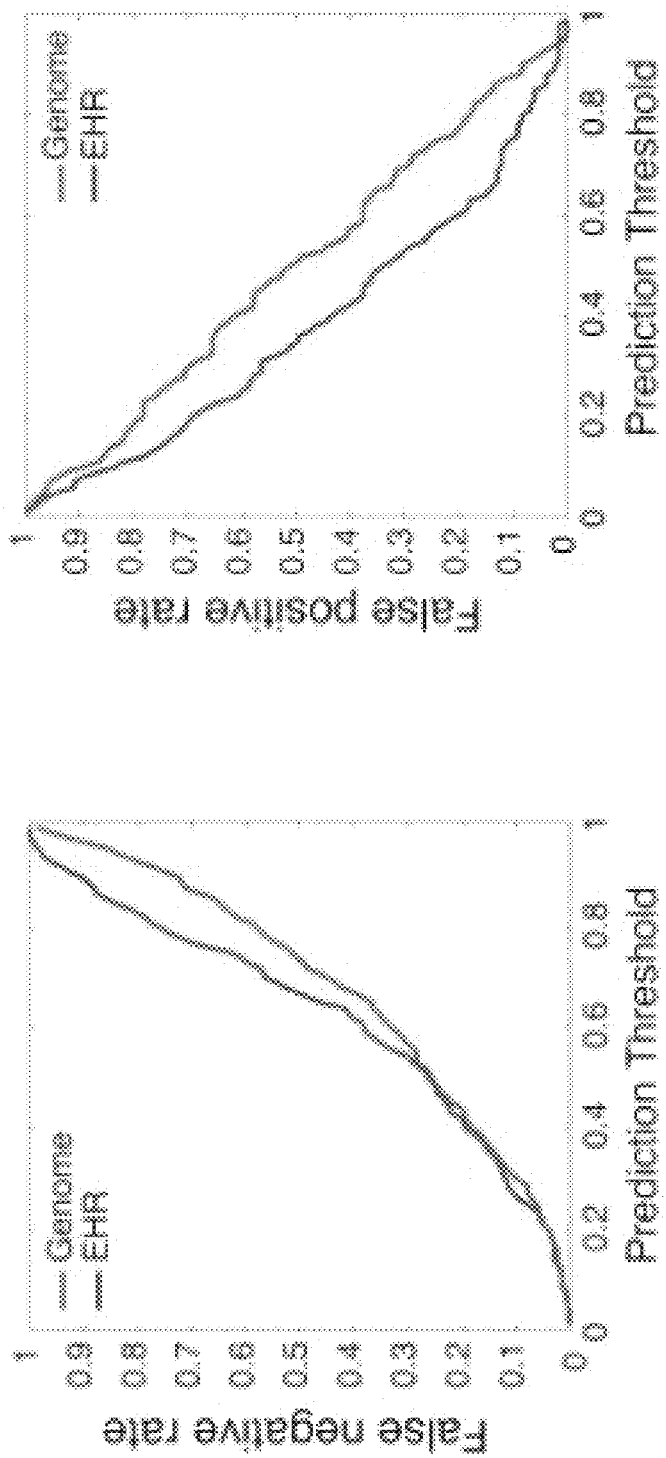
FIG. 19A provides graphs detailing comparisons of false negative rate and false positive rate between genome and health record based models generated in accordance with various embodiments of the invention.

The false positive and false negative rates achieved by the genome- and EHR-based models were next examined, which could guide clinical practice. Interestingly, the genome-based model had an overall comparable or lower false negative rate (the ability to capture real patients) than the EHR model across all possible prediction thresholds (FIG. 19A, left panel), but with a relatively higher false positive rate (FIG. 19A, right panel). The corresponding true positive, true negative, false positive and false negative rates at each prediction threshold are displayed in FIG. 19B. In practice, the choice of a prediction threshold should be based on the clinical demand by trading-off the false positive and negative rates. Beyond the analytical comparison, from a clinical perspective, it is important to note that the EHR information reflects the current status of an individual, whose value is limited for disease assessment at very early stage. However, the genome-based model will allow an early assessment of this disease for personal genome baselines, which is critical given the irreversible progression of the disease, and such an early assessment tool is lacking and strongly desired in clinical practice. Given its low false negative rate and relatively higher false positive rate, the genome-based model has the potential to be deployed as an early screening tool for AAA, and the false positive calls can be easily complemented by the inexpensive and non-invasive ultrasound follow-ups.

Figure 20:
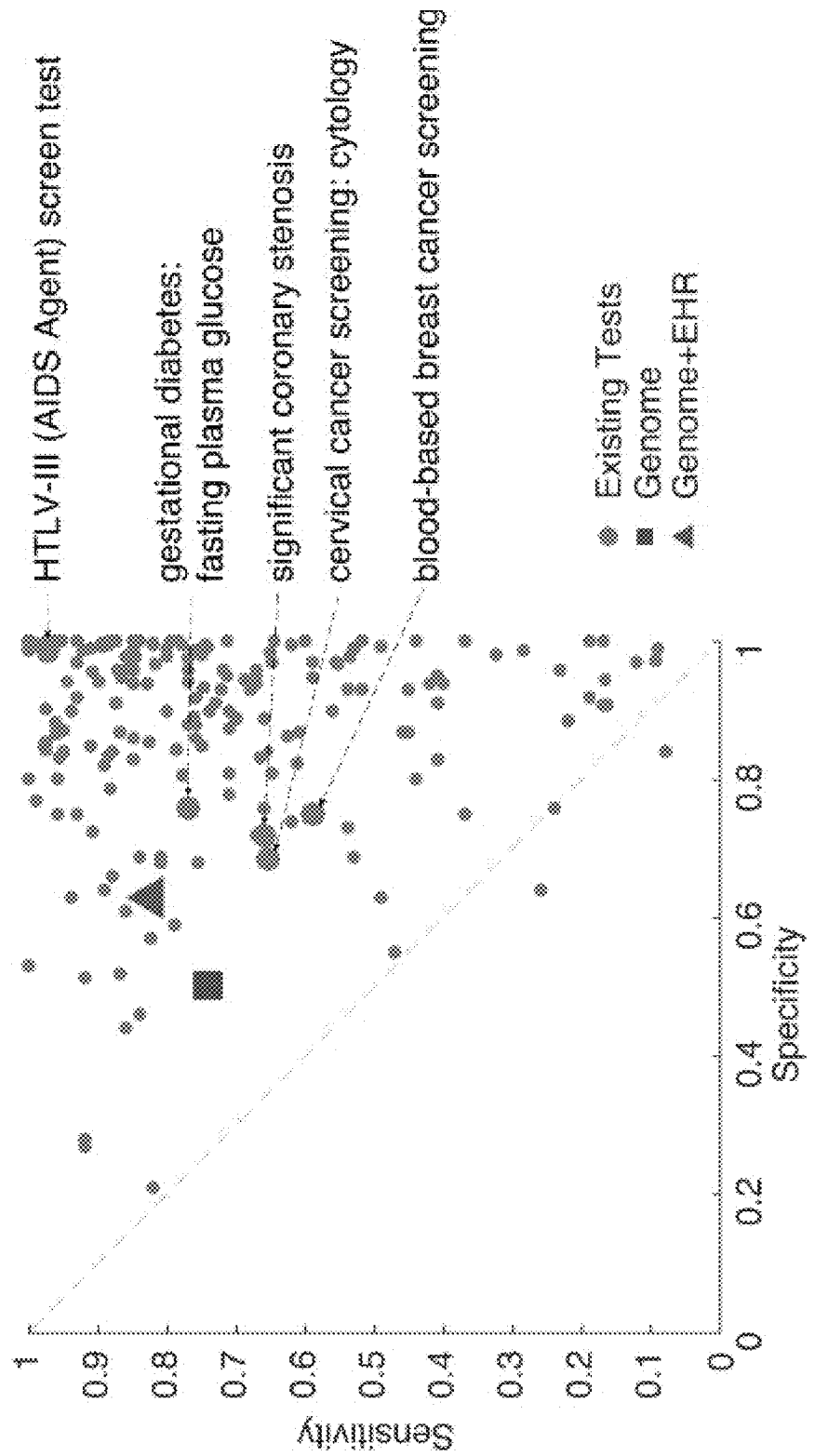
FIG. 20 provides a graph detailing the performance of HEAL as compared to existing clinical tests generated in accordance with various embodiments of the invention.

To demonstrate the predictive strength and clinical utility of HEAL, 1,000 sets of blind testing using the 10-fold cross-validation procedure were performed (as described above). It was then determined that the mean sensitivity (SN) and specificity (SP) of the genome-based model and the integrated model by aggregating genome and EHR information. Both models have achieved at the same level or better than many of the widely used clinical screening tests for different diseases (FIG. 20) (See, Maxim, L. D., Niebo, R and Utell, M. J., *Inhal. Toxicol.* 2014, 26, 811-828, the disclosure of which is incorporated herein by reference), including gestational diabetes, significant coronary stenosis, and cytology-based cervical cancer screening, indicating that the currently described platform has clinical applicability.

Interplay Between Personal Genomes and Lifestyles

Figure 21:
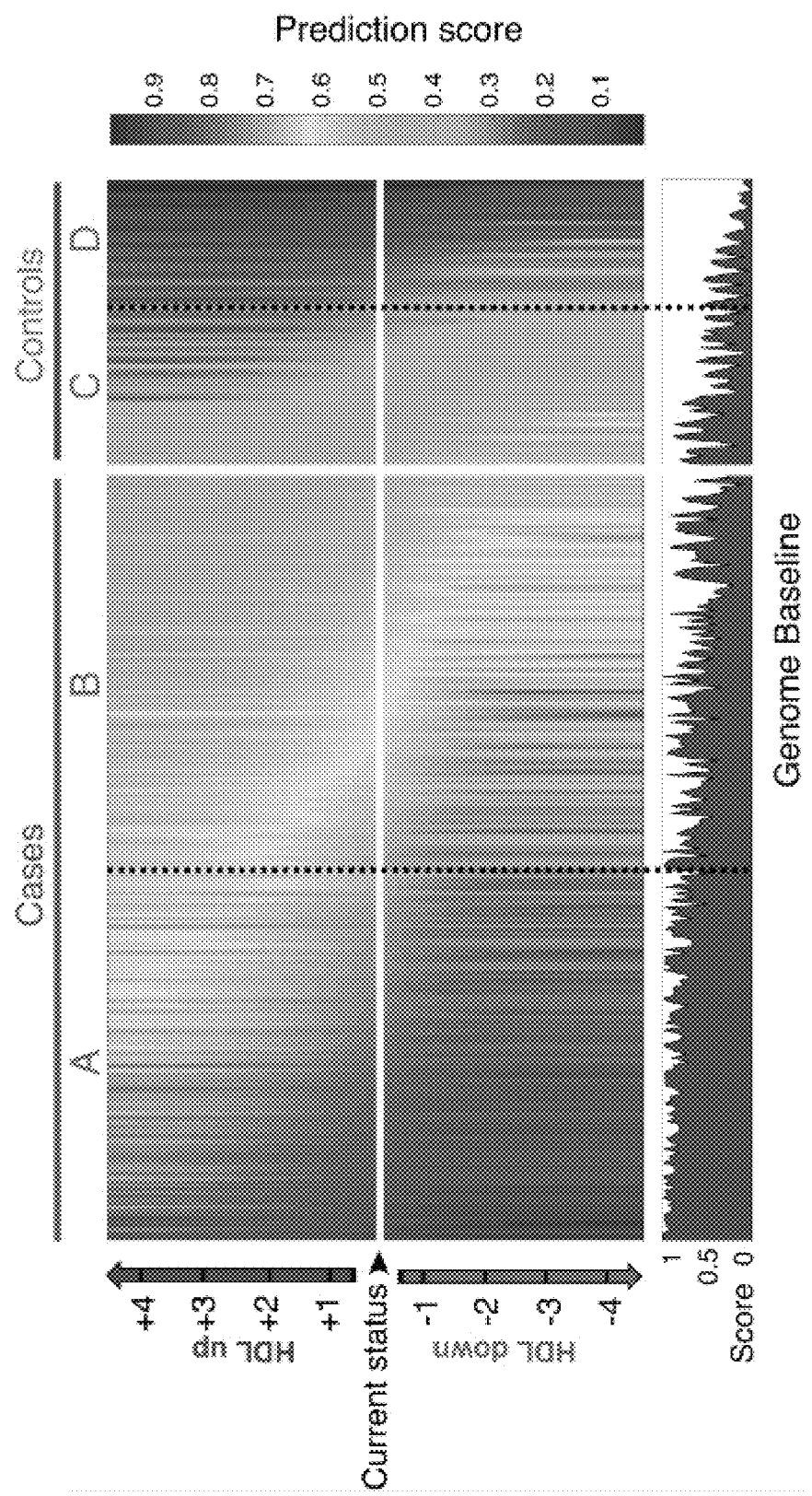
FIG. 21 provides a graph detailing the prediction of developing AAA by varying blood cholesterol levels generated in accordance with various embodiments of the invention.

For each individual, HEAL accurately predicted his/her AAA risk using personal genomes and EHR data. On the other hand, for the same individual with newly adopted lifestyles resulting in physiological changes (e.g. from a high-cholesterol diet to a low-cholesterol diet), HEAL can immediately update his/her AAA risk upon corresponding changes, condition on the person's genome baseline. This allows one to investigate the interplay between personal genomes and lifestyles underlying disease predisposition. Among many factors, plasma high-density lipoprotein (HDL) cholesterol level was used for the purpose of proof-of-principle given the unequivocal association between high HDL level and low AAA occurrence (See Torsney, E., et al., *Arterioscler. Thromb. Vasc. Biol.* 2012, 32, 2678-2686). A simulation study was performed on the AAA-positive cohort, in which participant's plasma HDL level was decreased and/or increased in silico, followed by a re-estimate of the associated AAA risk by HEAL condition on one's personal genome. For each individual, their current AAA risk was derived from the integrated model by aggregating personal genomes and EHRs; then step-wise increased or decreased their HDL levels from their HER-recorded values. FIG. 21 displays the risk profiles of individuals upon altering their plasm HDL levels. Overall, the HDL level was negatively correlated with AAA risk as scored by HEAL. However, for a subset of individuals (Group A and D), their AAA status (AAA positive for Group A and negative for Group D) was largely invariant upon HDL changes, corresponding to their extremely high or low genome baselines (prediction scores from the genome-based model, bottom panel, FIG. 21). In contrast, for most individuals, their AAA risk was sensitive to HDL changes: for those cases, an HDL increase could bring the predicted AAA risk down to the prediction threshold (risk score at 0.5, Group B), whereas for controls, an HDL reduction could result in a positive AAA prediction above the prediction score threshold of 0.5 (Group C). Taken together, these analyses highlight the importance of personalized health management by integrating one's genome baseline and lifestyle/physiological parameters, and demonstrate the applicability of HEAL as an effective tool for this purpose.

Identifying the Molecular Basis of AAA

Figure 22:
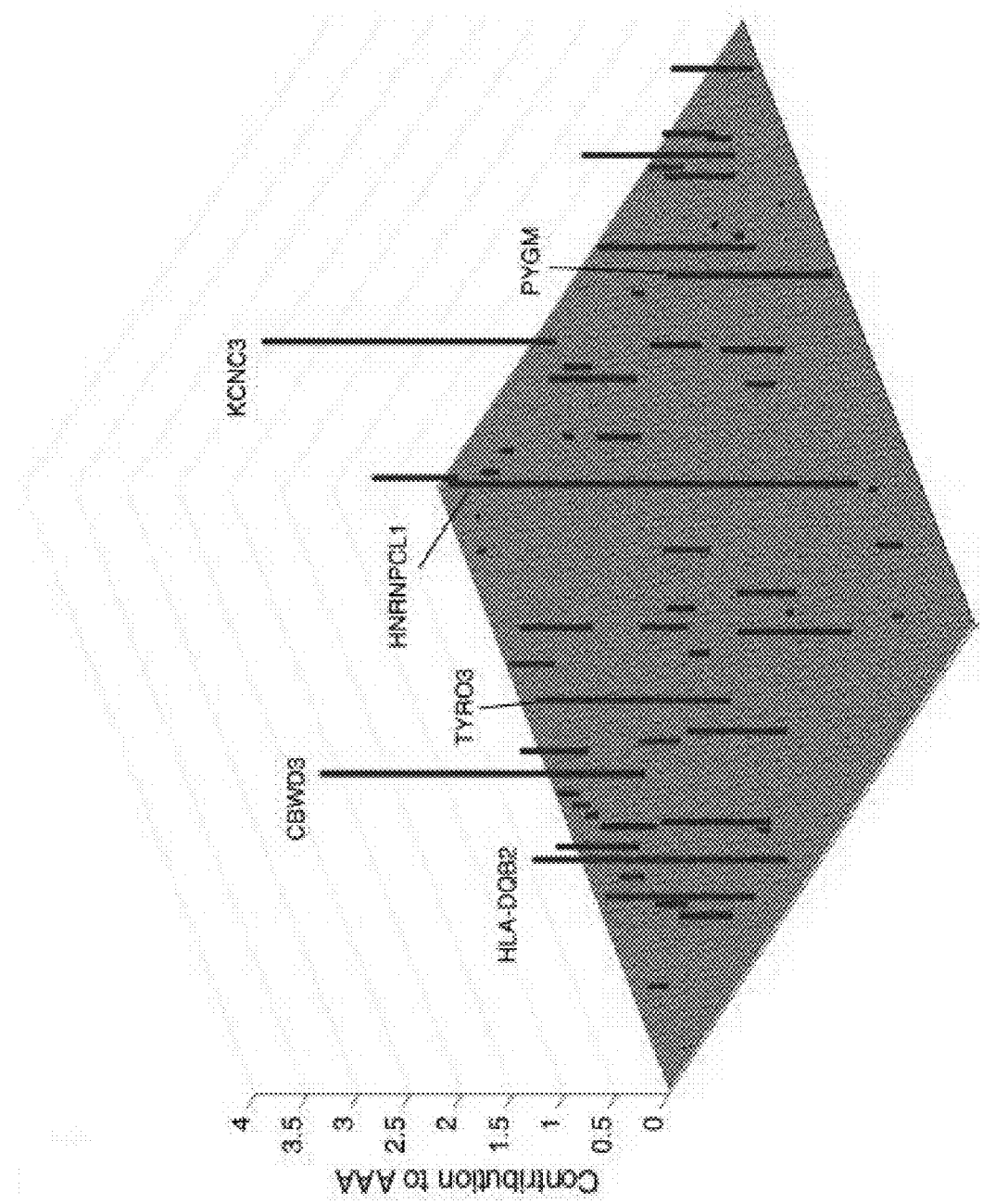
FIG. 22 provides a graph detailing the sixty genes identified by HEAL to be highly mutated in AAA patients compared to controls generated in accordance with various embodiments of the invention.
Figure 23:
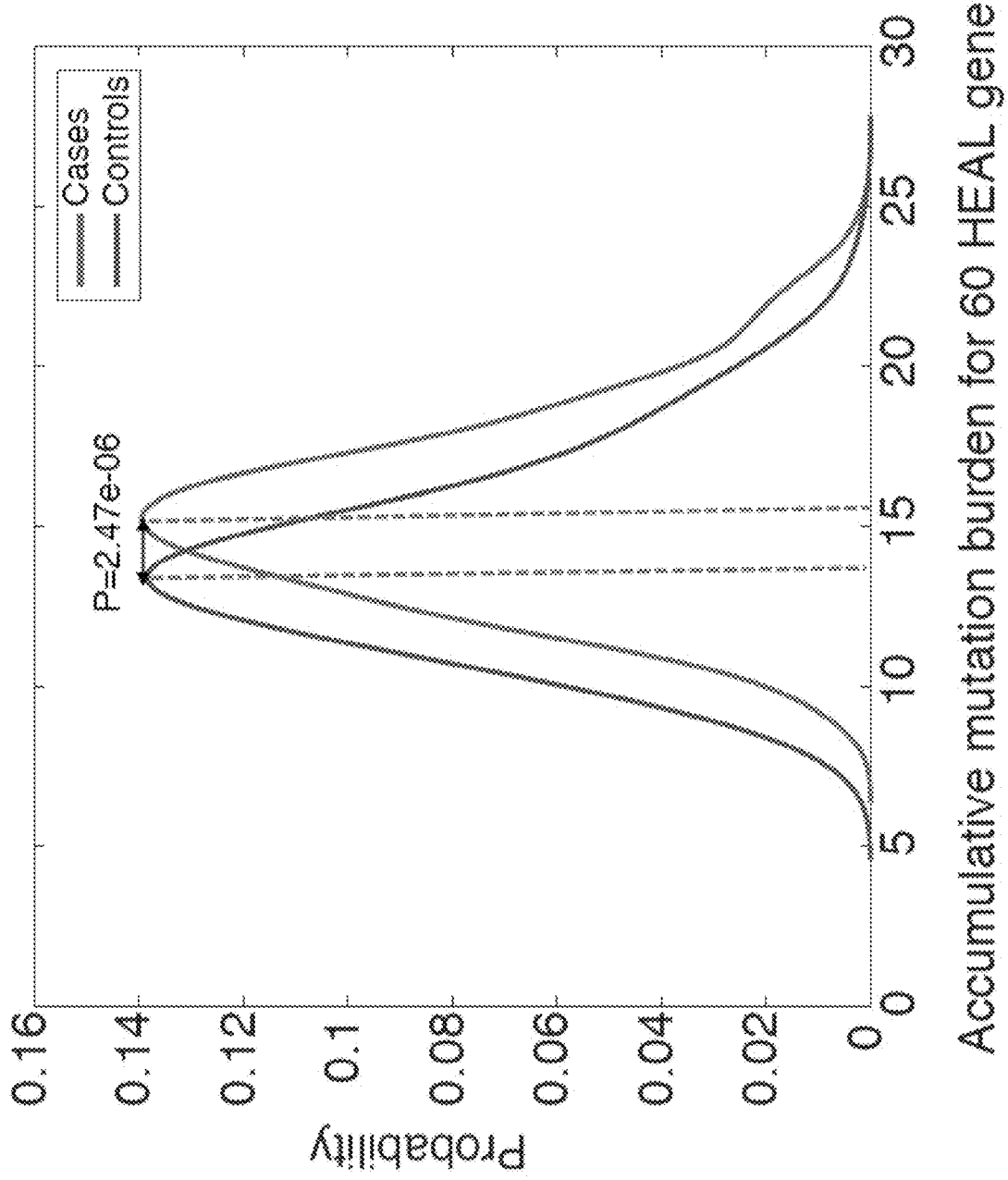
FIG. 23 provides a graph detailing accumulative mutation burden for 60 gene identified by HEAL generated in accordance with various embodiments of the invention.

HEAL agnostically identifies at-risk loci for the disease simultaneously with the prediction of disease risk. In the current example, HEAL agnostically and automatically selected 60 genes with a high accuracy of prediction (FIG. 22). Close examination of the 60 machine-identified genes confirmed their increased mutational burden for deleterious rare variants in cases relative to controls (FIG. 23; $p=2.47e^{-6}$). It was then examined whether these machine-identified genes could help reveal unbiased sources of molecular etiology in this disease. The 60 HEAL genes (Table 2) displayed an overall enrichment for immune-related functions, such as interferon-gamma-mediated signaling (FDR=0.07), MHC class II receptor activity (FDR=1.6e-4), and T cell co-stimulation (FDR=0.07), which is consistent with the known significant immunological/inflammatory components of AAA pathophysiology (Kuivaniemi, H., Platsoucas, C. D. and Tilson, M. D., *Circulation* 2008, 117, 242-252, the disclosure of which is incorporated herein by reference).

Figure 24:
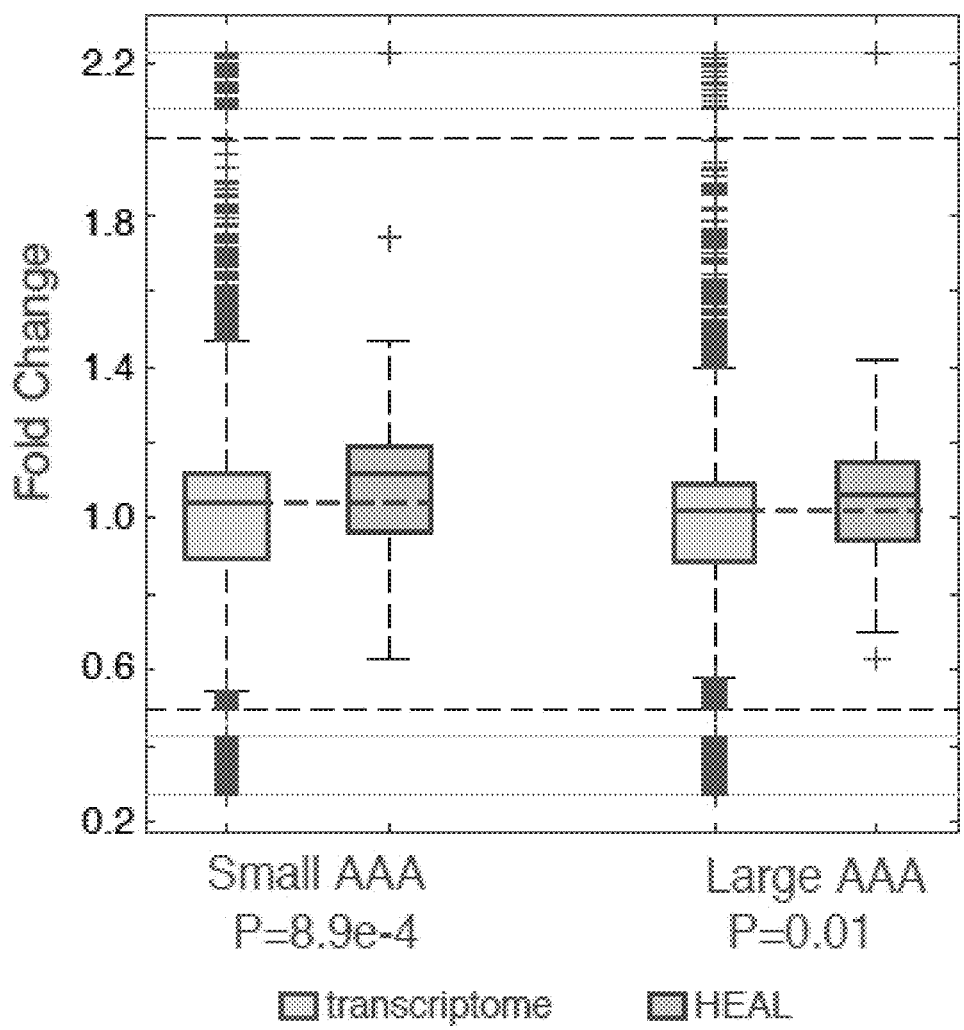
FIG. 24 provides a graph detailing the fold change of expression of the transcriptome and the sixty genes identified by HEAL in patients having small AAA and patients having large AAA generated in accordance with various embodiments of the invention.

To better understand the molecular function of the identified genes, their gene expression in human aortic specimens was compared. Tissue samples were obtained from 20 patients with small AAAs (30-55 mm), 29 patients with large AAAs (>55 mm), and 10 control aortic specimens (Biros, E., et al. *Ocotarget* 2015, 6, 12984-12996, the disclosure of which is incorporated herein by reference). The fold change for each human gene was computed and compared between small and large AAAs, relative to control subjects. Interestingly, the 60 HEAL genes displayed an overall significant up-regulation in both small AAA (FIG. 24, $P=8.90e^{-4}$, Wilcoxon rank-sum test), and large AAA specimens (FIG. 24, $P=1.9e^{-2}$, Wilcoxon rank-sum test). This comparison suggests a potential mechanism in AAA, where genetic alterations converge onto a common set of pathways, either by mutations or by altered gene expression.

To determine their functional context, the 60 HEAL genes were mapped onto the high-quality human protein-protein interaction (PPI) network, encompassing 16,083 proteins and 217,695 experimentally derived, non-redundant pair-wise interactions that were experimentally derived (Chatr-Aryamontri, A. *Nucleic Acid Res.* 2017, 45, D369-D379, the disclosure of which is incorporated herein by reference). The high quality of these protein interactions has been previously validated in an independent study (Li, J., et al. 2014, cited supra). The shortest path distances (SPD) on the network were computed for any pair of the HEAL genes as a proxy for their functional similarities. It was observed that the 60 genes did not exhibit reduced SPDs relative to any randomly selected protein pairs on the network. This observation suggests that the 60 HEAL genes are not topologically clustered, but are likely distributed across several biological pathways underlying the disease. Therefore, multiple functional modules likely contribute to AAA, rather than only a few tightly clustered functional components, which is consistent with published pathway data (Spin, J. M., et al., *Phsiol. Genomics* 2011, 43, 993-1003, the disclosure of which is incorporated herein by reference).

Functional Modules in AAA

The 60 HEAL genes were seeded into the protein interaction network, and devised a new framework to identify proteins tightly clustered with these HEAL genes as topological modules. Diffusion component analysis was performed (Cho, H., Berger, B. and Peng, J. *Cell Syst.* 2016, 3, 540-548, the disclosure of which is incorporated herein by reference) on the network, where the low-dimensional representation of each node was derived to best characterize the topological feature of each protein. Clustering proteins in low dimensional space defines topological modules on the protein interaction network, thereby identifying proteins with similar biological functions in each module.

Figure 25:
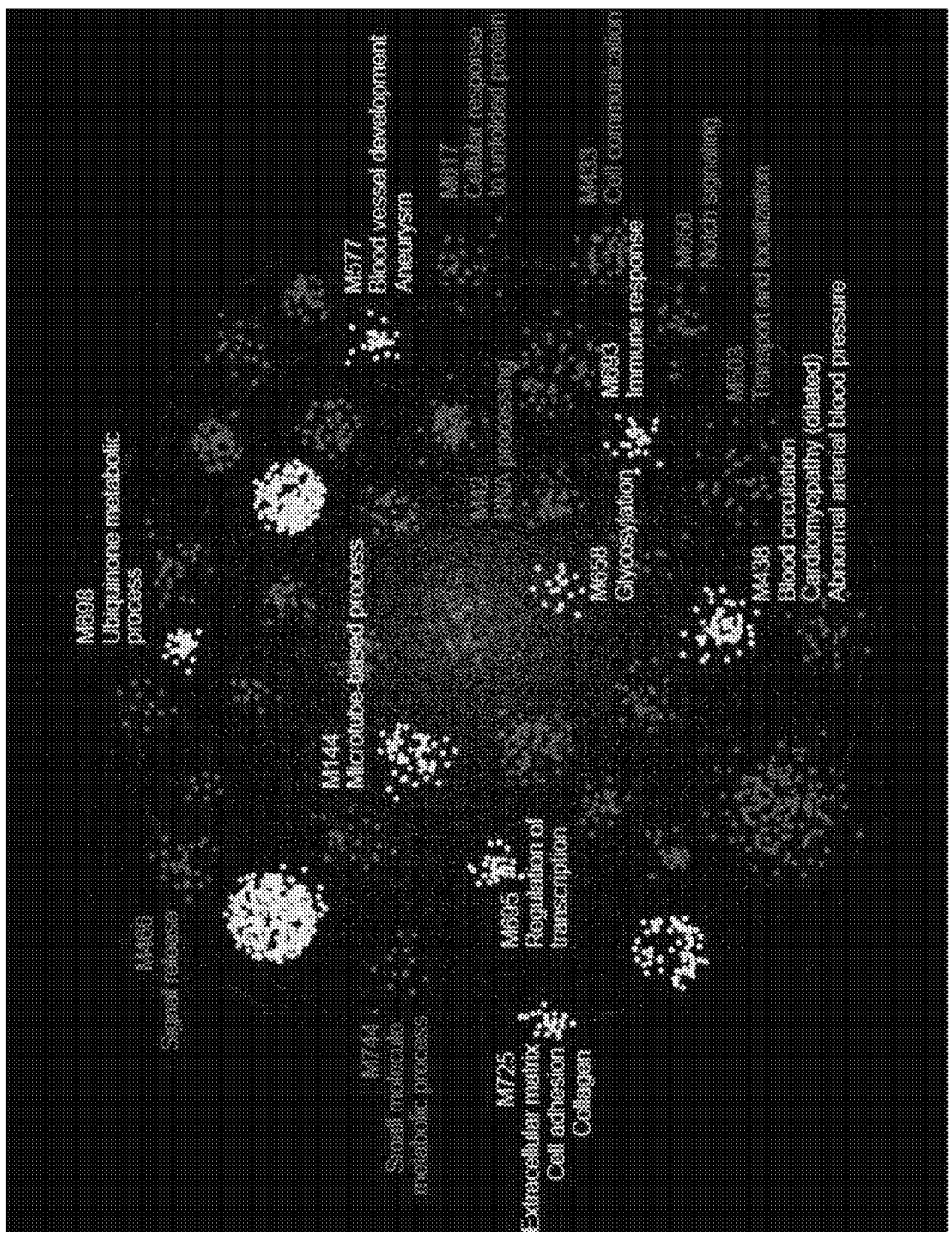
FIG. 25 provides a chart detailing the clustering of topological modules encompassing the sixty genes identified by HEAL generated in accordance with various embodiments of the invention.

First, for individual genes in PPI, their low-dimensional representations that profiled their topological characteristics in the PPI were discovered. These representations were derived depending on the diffusion component analysis (DCA), a recently developed method to embed node in a network into a low-dimensional feature space (Cho, H., Berger, B. and Peng, J., 2016, cited surpa). DCA has achieved the state-of-the-art performance in several tasks, like gene function prediction, gene ontology reconstruction and genetic interaction, demonstrating that the topological features of genes in the PPI determine their functions to some extent. Here, a 500-dimensional feature vector was generated for each gene. Then the k-means were clustered (with cosine distance) to assemble genes with similar topological features into the same cluster, dissecting the whole PPI into separate subnetworks/modules, where genes in the same cluster play a similar functional role. To determine the final cluster number, 20 candidate cluster numbers from 50 to 1,000 with step size 50 were tested, and the Silhouette index was used to measure the clustering quality. The final cluster number 750 achieved the best Silhouette value (s=0.1895). Furthermore, the 60 HEAL genes were mapped to the PPI, and all the genes belonging to one of the clusters involving at least one HEAL gene were extracted to construct the HEAL modules. Forty tightly clustered topological modules encompassing the 60 HEAL genes were identified (FIG. 25). The sizes of the 40 modules were uneven (FIG. 25). Gene ontology confirmed the functional coherence of the proteins in each module (FIG. 25), such as significant enrichment for blood vessel development in module M577 (FDR=2.3e-8) and blood circulation in module M438 (FDR=4.8e-3).

Figure 26:
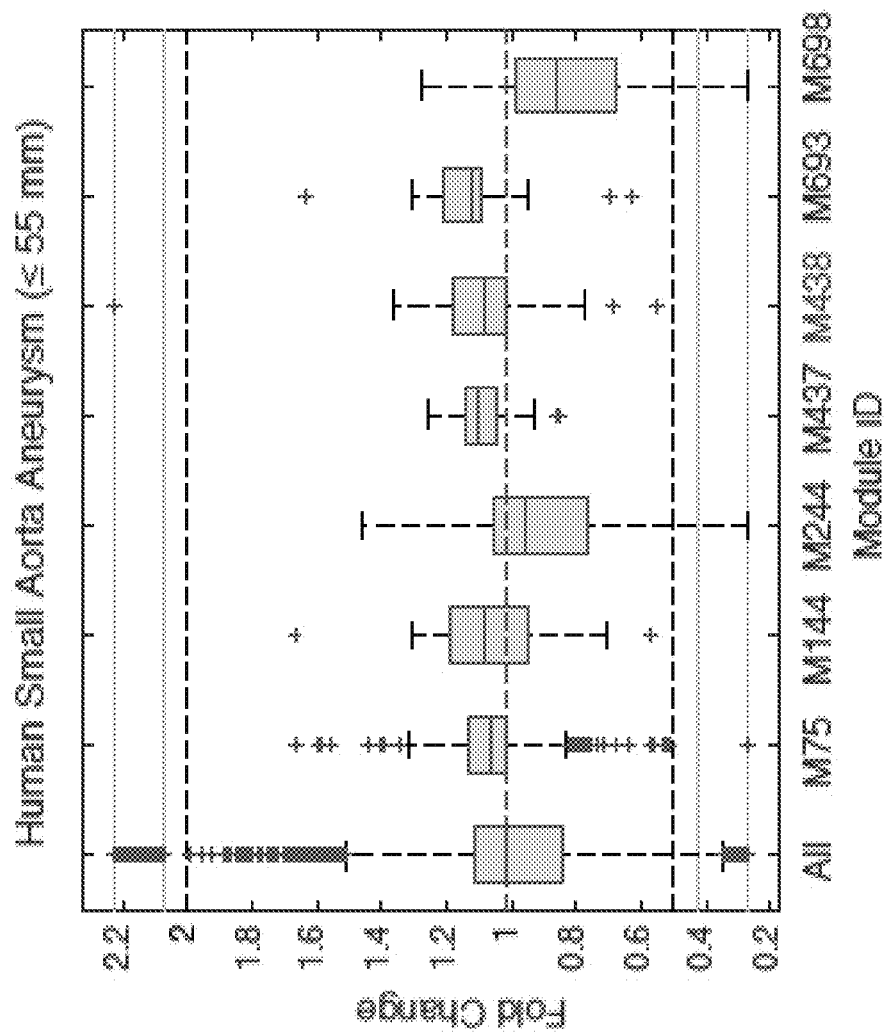
FIG. 26 provides the expression of various gene modules that are dysregulated in human AAA samples generated in accordance with various embodiments of the invention.
Figure 27:
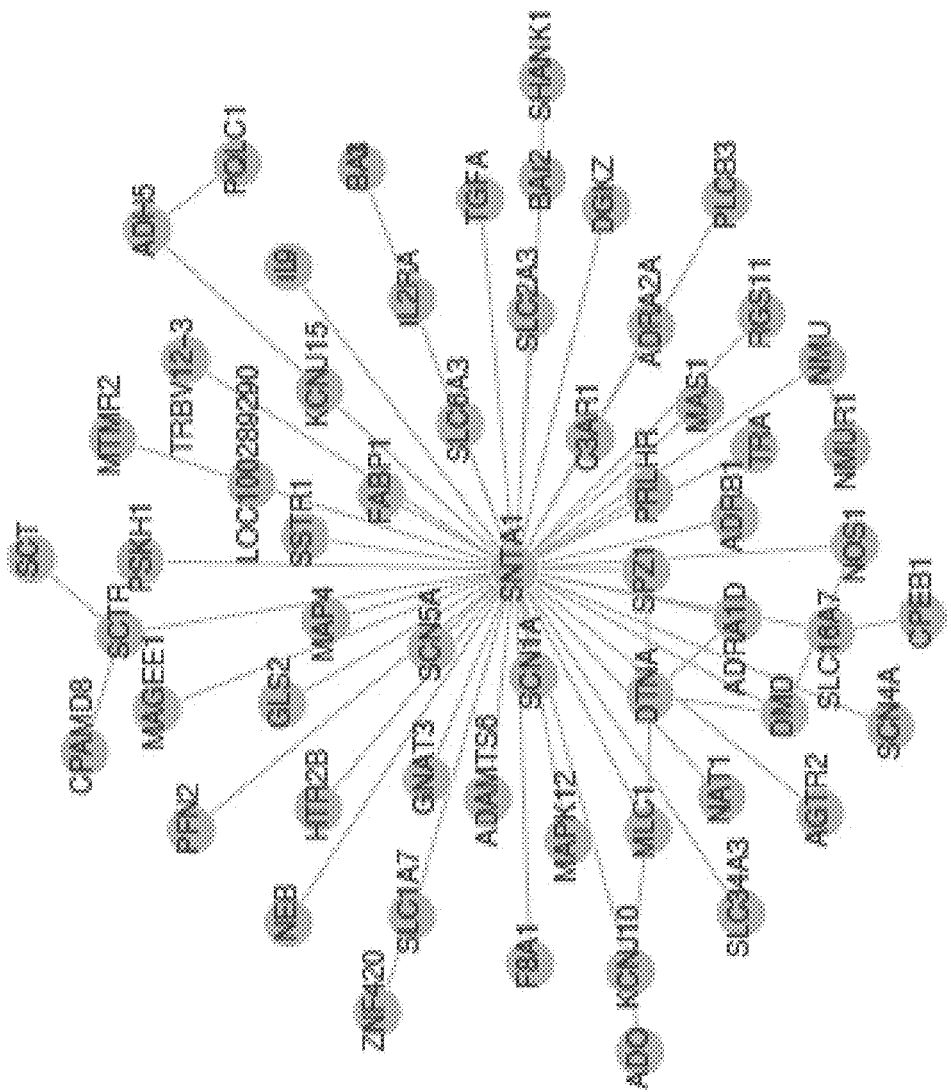
FIG. 27 provides an illustration demonstrating the gene relationships in the M438 gene module (blood circulation, blood pressure, cardiomyopathy) generated in accordance with various embodiments of the invention.

To interrogate the pathogenic roles of the modules in AAA, their expression was examined in human AAA tissue samples (Biros, E., et al., 2015, cited supra) as described above (FIG. 26). Interestingly, in either small or large AAA cohorts, the same set of seven modules exhibited significant dysregulation, including the up-regulation of module M438 (regulation of blood circulation) (FIG. 27, FDR=1.2e$^{-3}$ for small AAA and FDR=2.7e$^{-3}$ for larger AAA). It was noted that module M438 was strongly associated with abnormal systemic arterial blood pressure and dilated cardiomyopathy phenotypes according to OMIM annotations (FDRs<0.05).

Figure 28:
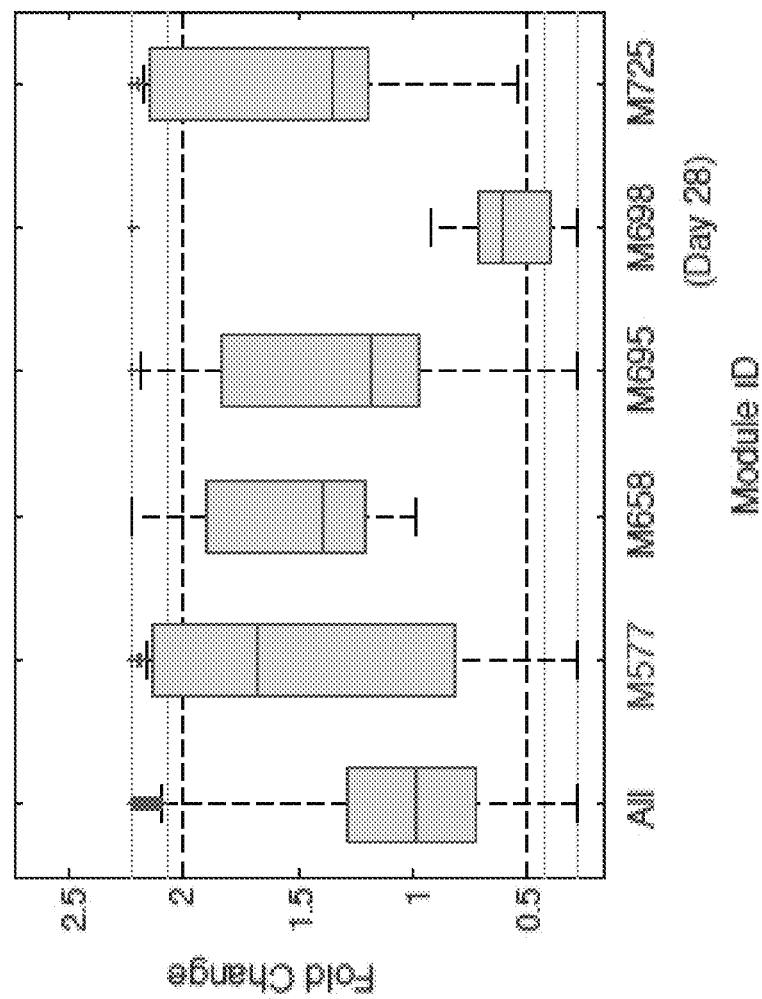
FIG. 28 provides the expression of various gene modules that are dysregulated in aortic samples of mouse models that develop AAA generated in accordance with various embodiments of the invention.
Figure 29:
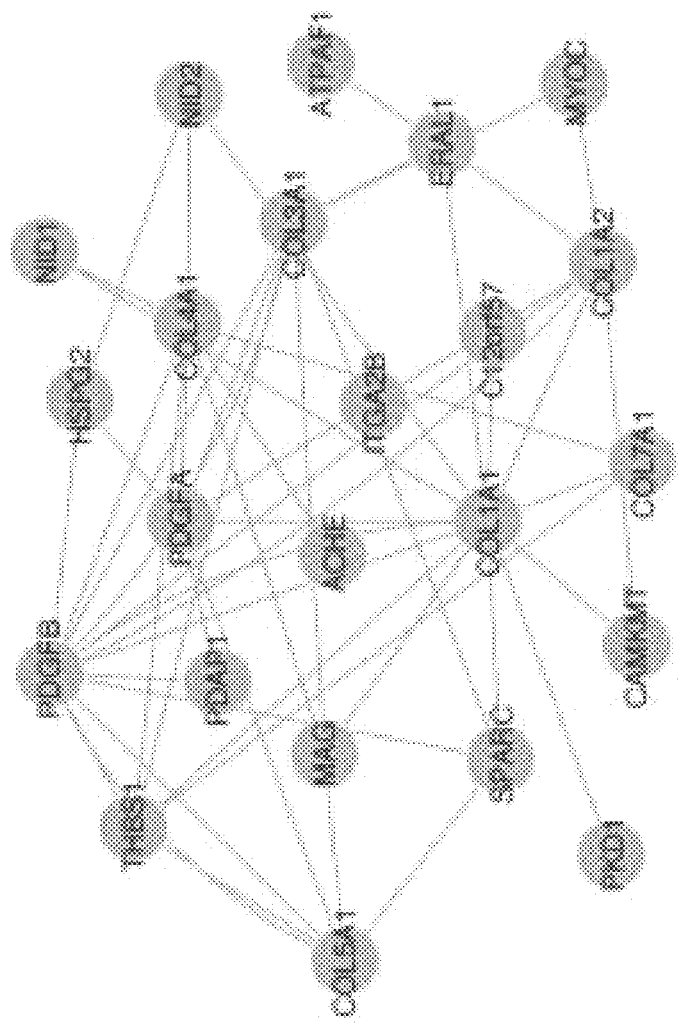
FIG. 29 provides an illustration demonstrating the gene relationships in the M577 gene module (aneurysm) generated in accordance with various embodiments of the invention.

It was next examined whether the identified modules might be involved in AAA development in murine models. In one well-established model, angiotensin II (AngII) is infused via implantable pumps into apolipoprotein E-deficient (ApoE$^{-/-}$) mice, which then develop suprarenal AAAs, exhibiting predictable resultant histopathology which shares many features with human disease (Daugherty, A., Manning, M. W., and Cassis, L. A., *J. Clin. Invest.* 2000, 105, 1605-1612, the disclosure of which is incorporated herein by reference). The whole genome microarray-based transcriptional profiling of aortic tissue from the AngII/ApoE$^{-/-}$ model, over a 28-day time course, was previously published (Spin, J. M., et al., 2011, cited supra). These studies suggested (based on pathway analysis), that Day 7 represents a critical period in AAA development in this model, which is followed by progressively less differential gene regulation over time (Spin, J. M., et al. 2011, cited supra). One-to-one unambiguous mouse orthologs of the 60 modular genes noted above were considered. In addition, five modules exhibiting significant expression alterations in developing AAA phenotypes at Day 7 in the murine model (FIG. 28), including significant up-regulation of module M577 (FDR=0.05, Wilcoxon rank-sum test) and module M725 (FDR=4.6e$^{-3}$, Wilcoxon rank-sum test) for the collagen metabolic process (FDR=0.01, Wilcoxon rank-sum test). For module M577, the corresponding mouse mutants showed aneurysm phenotypes according to Mouse Genome Informatics (FDR=1.96e-6, MGI:MP0003279, FIG. 29), whereas for the role of module M725 in collagen-associated function, its involvement in AAA was previously established (Menashi, S., et al., *J. Vasc. Surg.* 1987, 6, 578-582, the disclosure of which is incorporated herein by reference). Unsurprisingly, by Day 28, only module M698 for quinone biosynthetic process remained significant (FDR<0.05, Wilcoxon rank-sum test).

Another established murine AAA model that mimics many human AAA features involves localized infusion of porcine pancreatic elastase (PPE) into the infrarenal aorta of 10-week old C57BL/6 mice. Previous studies have found that PPE-induced aortic AAA size also differs significantly in size from those of sham (saline-infused) animals by Day 7, and that transcriptional profiling at that time point identifies numerous up- and down-regulated genes (Maedefessel, L., et al., *Nat. Commun.* 2014, 31, 5214, the disclosure of which is incorporated herein by reference). With the same procedures described above, module M698 and M704 showed significance in the PPE data (FIG. 30, FDR<0.1, Wilcoxon rank-sum test), where M698 for quinone biosynthesis consistently showed significance as seen in human tissues and the ANG II model, and module M704 for cell-cell communication (FDR=1.8e-2) was specific to the PPE model. Taken together, these comparisons involving human tissues and mouse models collectively demonstrate the pervasive involvement of the HEAL modules in AAA. It should be noted that the human samples described above likely represent end-stage disease while the animal model studies illustrate the dynamic nature of disease progression, highlighting the evolving involvement of multiple modular genes and pathways over time.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

TABLE 2

Minimal Gene Set Related to AAA as Determined by HEAL

| | |
|---|---|
| 1 | HNRNPCL1, HNRNPCL3, HNRNPCL4 |
| 2 | CBWD3 |
| 3 | KCNC3 |
| 4 | HLA-DQB2 |
| 5 | TYRO3 |
| 6 | PYGM |
| 7 | FAM205A |
| 8 | AIRE |
| 9 | NOMO1 |
| 10 | VPS13C |
| 11 | FAM8A1 |
| 12 | CACNA1B |
| 13 | NEB |
| 14 | KRTAP4-3 |
| 15 | CNTN5 |
| 16 | SIRPA |
| 17 | SLC12A3 |
| 18 | POTEE |
| 19 | ZNF469 |
| 20 | AGAP3 |
| 21 | IGFN1 |
| 22 | KCNJ12, KCNJ18 |
| 23 | PSPH |
| 24 | COL5A1 |
| 25 | MYH7B |
| 26 | POLR2J3 |
| 27 | HKDC1 |
| 28 | PLEKHH1 |

TABLE 2-continued

Minimal Gene Set Related to AAA as Determined by HEAL

| 29 | SCRIB |
| 30 | KRT86 |
| 31 | SCGB1C1, SCGB1C2 |
| 32 | MYO15A |
| 33 | GOLGA8A |
| 34 | DHX34 |
| 35 | ARSD |
| 36 | POTEM |
| 37 | FAM136A |
| 38 | OTOG |
| 39 | RFPL4AL1 |
| 40 | SCN10A |
| 41 | PKP3 |
| 42 | NBPF10 |
| 43 | CPT1B |
| 44 | LILRA6, LILRB3 |
| 45 | MUC21 |
| 46 | TULP4 |
| 47 | TPSB2 |
| 48 | PCDH11Y |
| 49 | NPIPB15 |
| 50 | HLA-DQA1 |
| 51 | PABPC1 |
| 52 | HLA-DQB1 |
| 53 | MAGEC1 |
| 54 | CYP2D6 |
| 55 | NOTCH2 |
| 56 | ITGAE |
| 57 | OR4A16 |
| 58 | PRB4 |
| 59 | ABCC1 |
| 60 | HLA-B |

What is claimed is:

1. A method of performing targeted sequencing of an individual's genetic material to determine if the individual has a propensity for a complex disorder, comprising:
   obtaining a first variant profile and a second variant profile, wherein the first variant profile is derived from sequencing data of a first cohort of patients having a complex disorder and the second variant profile is derived from sequencing data from a second cohort of patients not having the complex disorder;
   assigning each variant within the first variant profile and each variant within the second variant profile a predicted deleteriousness effect;
   determining a burden of each variant within the first variant profile and each variant within the second variant profile based on the predicted deleteriousness effect and its frequency within its cohort;
   for each variant profile, determining an aggregated variant burden for each gene of a human genome, wherein the aggregated variant burden is an aggregation of burdens of the variants in the gene;
   training a classification model with the first variant profile and the second variant profile to distinguish individuals having a complex disorder from individuals not having the complex disorder utilizing an aggregated variant burden for each gene in a subset of genes of the set of genes as features, wherein each gene of the subset of genes has an elevated aggregated variant burden within individuals having the complex disorder, wherein the subset of genes is a minimum set of genes learned by the classification model to solve a logistic regression problem having an optimization objective that is an average cross-entropy of the subset of genes;
   identifying the subset of genes, using the trained classification model, that are able to distinguish individuals having a complex disorder from individuals not having the complex disorder based upon the aggregated variant burden the subset of genes;
   synthesizing a set of nucleic acid oligomers consisting of sequences that hybridize to sequences of the subset of genes;
   obtaining genetic material of an individual;
   performing capture hybridization or amplification targeting regions of the genetic material to prepare a sequencing library utilizing the set of nucleic acid oligomers, wherein the regions consist of loci of the identified subset of genes; and
   performing targeted sequencing utilizing the sequencing library to yield a targeted sequencing result of genes identified to be burdened within the complex disorder.

2. The method of claim 1, wherein identifying the set of genes is based upon a difference in variant patterns between the first cohort of patients having the complex disorder and the second cohort of patients not having the disorder.

3. The method of claim 1, wherein the genetic material of the individual is derived from a biopsy of the individual.

4. The method of claim 1, wherein the variant pattern includes rare variants as defined by their minor allele frequency.

5. The method of claim 4, wherein the rare variants have a minor allele frequency selected from: less than or equal to 5% and less than or equal to 1%.

6. The method of claim 1, wherein the deleteriousness of variants is an effect on the protein product the gene encodes.

7. The method of claim 1, wherein the aggregated variant burden for each gene is calculated as follows:

$$g_i = \sum_{j=1}^{n_i} s_{ij}$$

wherein $n_i$ is the number of variants in gene i and $s_{ij}$ is the average deleteriousness score for each variant j.

8. The method of claim 1, wherein trait-risk coefficients are computed for each gene with the subset of genes, and wherein each trait-risk coefficients measure the contribution of the aggregated variant burden of each gene to diagnostic status.

9. The method of claim 1, further comprising:
   determining, utilizing the trained classification model, a diagnosis of the individual by entering the individual's targeted sequencing result into the trained classification model, wherein the diagnosis is determined by an aggregation score of an aggregated variant burden for each gene of the subset of genes, wherein the diagnosis indicates a propensity for the complex disorder; and
   administering a treatment to the individual for the complex disorder.

10. The method of claim 1, wherein the classification model utilizes a sparse learning technique.

11. The method of claim 1, wherein the classification model is a penalized linear classification model.

12. The method of claim 11, wherein the penalized linear classification model utilizes a logistic regression version of least absolute shrinkage and selection operator (LASSO).

13. The method of claim 11, wherein a penalty term is $L_1$ calculated:

$$\min_w \mathcal{L}_2(w) = \min_w \mathcal{L}_1(w) + \lambda \|w\|_1$$

wherein the $L_1$ norm induced a sparse structure, the parameter $\lambda$ tuned the level of sparsity of the solution and can be set to user defined number.

14. The method of claim 13, wherein identifying the set of genes to distinguish individuals having a complex disorder from individuals not having the complex disorder comprises using the penalty term.

15. The method of claim 1, wherein the complex disorder is selected from the group consisting of: abdominal aortic aneurysm, Alzheimer disease, arthritis, asthma, bipolar disorder, autism spectrum disorder, cancer, cleft lip and/or palate, coronary artery disease, Crohn's disease, dementia, depression, diabetes, heart disease, heart failure, high cholesterol, hypertension, hypothyroidism, irritable bowel syndrome, obesity, osteoporosis, Parkinson disease, rhinitis, psoriasis, multiple sclerosis, schizophrenia, sleep apnea, spina bifida, and stroke.

16. The method of claim 1, wherein the complex disorder has no single variant that is diagnostic.

17. The method of claim 9, wherein diagnostic status is based upon:

$$\hat{y}_n = P(y_n = 1 \mid x_n) = \sigma(w^T x_n) = \frac{1}{1 + \exp(-w^T x_n)}$$

wherein an individual n has a gene trait burden profile $x_n$ and $\sigma(\cdot)$ is a sigmoid function.

18. The method of claim 9, wherein the complex disorder is abdominal aortic aneurysm and the step of administering a treatment to the individual comprises:

administering one or more of the following: a diuretic, a beta blocker, an ACE inhibitor, an angiotensin II receptor blocker, a calcium channel blocker, a statin, a bile acid sequestrates, a cholesterol absorption inhibitor, a PCSK9 inhibitor, or a fibrate.

19. The method of claim 1, wherein the complex disorder has a heritability of 70% or greater.

* * * * *